United States Patent
Gaeta et al.

(10) Patent No.: US 7,585,875 B2
(45) Date of Patent: Sep. 8, 2009

(54) SUBSTITUTED PYRAZOLO[1,5-A]PYRIDINE COMPOUNDS AND THEIR METHODS OF USE

(75) Inventors: Federico C. A. Gaeta, Mountain View, CA (US); Matthew Gross, Vallejo, CA (US); Kirk W. Johnson, Moraga, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 11/810,885

(22) Filed: Jun. 6, 2007

(65) Prior Publication Data

US 2008/0070912 A1 Mar. 20, 2008

Related U.S. Application Data

(60) Provisional application No. 60/811,604, filed on Jun. 6, 2006.

(51) Int. Cl.
*A61K 31/44* (2006.01)
(52) U.S. Cl. ........................................ 514/300; 514/866
(58) Field of Classification Search .................. None
See application file for complete search history.

(56) References Cited

U.S. PATENT DOCUMENTS

| | | | |
|---|---|---|---|
| 3,850,941 | A | 11/1974 | Irikura et al. |
| 4,097,483 | A | 6/1978 | Irikura et al. |
| 4,925,849 | A | 5/1990 | Shiokawa et al. |
| 2005/0187203 | A1 | 8/2005 | Jost-Price et al. |
| 2005/0192261 | A1 | 9/2005 | Jost-Price et al. |
| 2005/0240021 | A1 | 10/2005 | Campbell et al. |
| 2006/0004003 | A1 | 1/2006 | Abe et al. |

FOREIGN PATENT DOCUMENTS

| | | |
|---|---|---|
| EP | 0 379 979 A1 | 8/1990 |
| EP | 0 516 941 A1 | 12/1992 |
| WO | WO-00/24742 A1 | 5/2000 |
| WO | WO-00/26216 A1 | 5/2000 |
| WO | WO-00/52008 A1 | 9/2000 |
| WO | WO-02/18382 A1 | 3/2002 |
| WO | WO-03/045950 A1 | 6/2003 |
| WO | WO-2004/074290 A1 | 9/2004 |
| WO | WO-2006/063048 A2 | 6/2006 |

OTHER PUBLICATIONS

Avigen, Inc., The International Search Report and Written Opinion for PCT application PCT/US2007/013456 Search report dated Nov. 22, 2007, 23 pages (2007).

Fujimoto, T., et al., "Ibudilast, A Phosphodiesterase Inhibitor, Ameliorates Experimental Autoimmune Encephalomyelitis in Dark August Rats", *Journal of Neuroimmunology*, 95:35-42 (1999).

Mizuno et al., "Neuroprotective Role of Phosphodiesterase Inhibitor Ibudilast on Neuronal Cell Death Induced by Activated Microglia", *Neuropharmacology*, 46:404-411 (2004).

Momo, K., et al., "Effects of the New Antiplatelet Agent 2-Methyl-3-(1, 4, 5, 6-tetrahydronicotinoyl)pyrazolo[1, 5-a]pyridine on Platelet Aggregation and Thrombosis in Experimental Animals", *Arzneimittelforschung/Drug Res.*, 42(1):32-39 (1992).

Park, H., "The Effect of Ibudilast on Diabetic Peripheral Neuropathy", *Japanese Pharmacaology and Therapeutics*, 23(6):133-140 (English Abstract Translation) (1995).

*Primary Examiner*—Frederick Krass
*Assistant Examiner*—Marcos Sznaidman
(74) *Attorney, Agent, or Firm*—Susan T. Evans; King & Spalding LLP

(57) ABSTRACT

The present invention is directed to substituted pyrazolo[1,5-a]pyridines and related methods for their synthesis and use.

9 Claims, 2 Drawing Sheets

SUBSTITUTED PYRAZOLO[1,5-A]PYRIDINE COMPOUNDS AND THEIR METHODS OF USE

CROSS REFERENCE TO RELATED APPLICATIONS

This application claims the benefit of priority to U.S. Provisional Application No. 60/811,604, filed Jun. 6, 2006, the content of which hereby expressly incorporated herein by reference in its entirety.

FIELD

The present invention relates generally to substituted pyrazolo[1,5-a]pyridine compounds and compositions thereof, as well as methods for making and using such compounds, among others.

BACKGROUND

Ibudilast (3-isobutyryl-2-isopropylpyrazolo[1,5-a]pyridine) is a small molecule drug that has been used for many years in Japan and Korea for the treatment of bronchial asthma as well as for treatment of cerebrovascular disorders such as post-stroke dizziness. It is sold in these countries under the tradename, Ketas®. Marketed indications for ibudilast in Japan include its use as a vasodilator, for treating allergy, eye tissue regeneration, ocular disease, and treatment of allergic ophthalmic disease (Thompson Current Drug Reports). Its use in the treatment of both chronic brain infarction (ClinicalTrials.gov) and multiple sclerosis (News-.Medical.Net; Pharmaceutical News, 2 Aug. 2005) is currently being explored in separate, ongoing clinical trials.

The mechanisms of action of ibudilast have been widely explored. Its role as a non-selective inhibitor of cyclic nucleotide phosphodiesterase (PDE) has been described (Fujimoto, T., et al., *J. of Neuroimmunology*, 95 (1999) 35-92). Additionally, ibudilast has been reported to act as an LTD4 antagonist, an anti-inflammatory, a PAF antagonist, and a vasodilatatory agent (Thompson Current Drug Reports). Ibudilast is also thought to exert a neuroprotective role in the central nervous system of mammals, presumably via suppression of the activation of glial cells (Mizuno et al. (2004) *Neuropharmacology* 46: 404-411). New uses for ibudilast continue to be explored.

An analog of ibudilast, KC-764 (2-methyl-3-(1,4,5,6-tetrahydronicotinoyl)pyrazolo(1,5-a)pyridine, developed by Kyorin Pharmaceutical Co., has been reported to possess antiplatelet and antithrombotic activity (Momo, K., et al., *Arzneimittelforschung*, 1992, January 42(1), 32-9). KC-764 possesses a chemical structure that differs from ibudilast in the substituents at the 2- and 3-ring positions. Interestingly, its reported therapeutic use, primarily as an antiplatelet agent, differs significantly from that of the parent compound, ibudilast.

The applicants have surprisingly discovered that certain compounds belonging to the substituted pyrazolo[1,5-a]pyridine family are useful in the treatment of conditions such as neuropathic pain. Additionally, such compounds are useful for treating one or more of the following: inflammatory conditions, opiate withdrawal and taxol-induced neuropathy, as well as for antiviral therapy, among others. The shortcomings of current therapeutic approaches in each of these areas are well-known. It is believed that the compounds described herein provide one or more advantages over currently existing therapies.

SUMMARY

The present invention is generally directed to substituted pyrazolo[1,5-a]pyridine compounds. The compounds of the invention are particularly useful in the treatment of conditions such as neuropathic pain and migraine, among others.

In one aspect, provided herein are 2,3,6-substituted pyrazolo[1,5-a]pyridine compounds having the following structure:

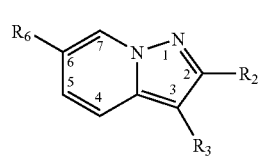

I

The compounds of the invention possess one or more substituents as described in greater detail below at one or more of ring positions 2, 3, and 6. That is to say, a compound of the invention may possess a single substituent at position 2, a single substituent at position 3, or a single substituent at position 6. Alternatively, a compound of the invention may be 2,3-disubstituted, 2,6-disubstituted, or 3,6-disubstituted. Further, a compound of the invention may be 2,3,6-trisubstituted.

In one particular embodiment, a compound in accordance with structure I is di-substituted at ring positions 2 and 3.

Referring to structure I above, each of $R_2$, $R_3$ and $R_6$ generally corresponds to the following, where:

$R_2$ is independently H or an organic radical selected from the group consisting of alkyl, substituted alkyl, aryl, substituted aryl, alkenyl, substituted alkenyl, alkynyl, substituted alkynyl, hydroxy, sulfhydryl, alkoxy, substituted alkoxy, aryloxy, substituted aryloxy, carbamoyloxy, thioalkyl, substituted thioalkyl, carbamoylthio, thioaryl, substituted thioaryl, amino, and carbamoylamino;

$R_3$ is independently H or an organic radical selected from the group consisting of alkyl, substituted alkyl, aryl, substituted aryl, alkenyl, substituted alkenyl, alkynyl, and substituted alkynyl; and $R_6$ is independently H or an organic radical selected from the group consisting of hydroxy, sulfhydryl, alkoxy, aryloxy, thioalkyl, thioaryl, amino, halogen, alkyl, alkenyl, alkynyl, aryl, cyano, carboxyl, and carboxamido. Illustrative carboxamido moieties include both linear amido moieties as well as lactams, morpholinamides, tetrahydroquinolineamides, tetrahydroisoquinolineamides, coumarinamides, and the like.

Preferably, a substituted pyrazolo[1,5-a]pyridine compound of the invention corresponding to structure I above is one where when $R_2$ is isopropyl and $R_3$ is 2-methylpropan-1-one, then $R_6$ is not H (i.e., is an organic radical other than hydrogen).

In one embodiment of the invention, $R_2$ is lower alkyl, substituted lower alkyl, amino, aryl, or substituted aryl.

In yet a further embodiment, $R_2$ is phenyl or substituted phenyl.

In a preferred embodiment, $R_2$ is lower alkyl or mono-substituted lower alkyl.

In a particular embodiment, $R_2$ is isopropyl or 2-hydroxypropan-2-yl.

In yet another embodiment, $R_2$ is phenyl or mono-substituted phenyl.

In yet another embodiment, $R_2$ is a phenyl ring possessing either a single halogen or alkoxy substituent. Preferred $R_2$ substituents include 4-halo phenyl groups such 4-fluorophenyl, 4-chlorophenyl, and 4-iodophenyl, as well as 4-alkoxy phenyl substituents.

In another embodiment, $R_6$ is H and $R_2$ is isopropyl.

In yet another embodiment, $R_3$ possesses the structure:

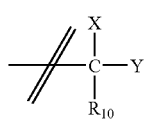

II where

represents the pyrazolo[1,5-a]pyridine ring system, and the carbon atom shown in structure II above is covalently attached to ring carbon 3, and C can be saturated or unsaturated.

In the event that C in structure II is saturated, X and Y are each independently selected from the group consisting of —H or an organic radical selected from the group consisting of hydroxyl, amino, alkoxy, cyano, halo, sulfhydryl, thioalkyl, lower alkyl, and substituted lower alkyl.

In one embodiment of structure II, when C (referring to structure II above) is unsaturated, X and Y, when taken together, form a double bond attached to a functional group, Z, selected from O, S, and N—$R_{11}$, where $R_{11}$ is selected from —OH, —O—C(O)—$NR_{12}R_{13}$, —O—C(O)—$R_{14}$, and $CR_{15}R_{16}$, and $R_{12}$, $R_{13}$, $R_{14}$ and $R_{15}$ are each independently selected from —H, lower alkyl, and aryl. Thus, when C is unsaturated, X and Y, when taken together with the carbon atom, may form one or more of the following moieties: ~C═O, ~C═S, ~C═N—OH, ~C═N—O—C(O)—$NR_{12}R_{13}$, ~C═N—O—C(O)—$R_{14}$, ~C═$CR_{15}R_{16}$, among others. In a preferred embodiment, $R_{12}$ and $R_{13}$ are both hydrogen.

In reference to structure II above, $R_{10}$ is independently H or an organic radical selected from alkyl, substituted alkyl, aryl, substituted aryl, alkenyl, substituted alkenyl, alkynyl, substituted alkynyl, and ester. In a preferred embodiment, $R_{10}$ is lower alkyl or substituted lower alkyl. Exemplary lower alkyl groups include isopropyl and 2-hydroxyisopropyl, among others. In yet another embodiment $R_{10}$ is an ester, e.g., a lower alkyl ester.

Alternatively, when C is unsaturated, X and Y, when taken together, form a double bond to C that, when taken together with $R_{10}$, forms part of an aromatic heterocycle. For example, C, together with X, Y, and $R_{10}$ may form part of a pyridine ring, a pyrazole ring, a pyrimidine ring, a pyridazine ring, an imidazole, a 1H-imidazole-2-(3H)-thione, a thiazole, a thiazole-2(5H)-imine, and the like, including substituted versions thereof.

For example, in one embodiment, $R_3$ corresponds to structure II above, where C is unsaturated, and C, taken together with X, Y, and $R_{10}$, forms a 3-pyridin-4-yl substituent, while $R_2$ is isopropyl.

In yet another embodiment, $R_3$ corresponds to structure II above, where C is unsaturated, and C, taken together with X, Y, and $R_{10}$, forms a substituted pyrimidine ring having a substituent at the 2-position of the pyrimidine ring, while $R_2$ is isopropyl. In a particular embodiment thereof, the substituent at the 2-position of the pyrimidine ring is an isopropylamino group. Preferably, the pyrimidine ring is attached to the core pyrazolo[1,5-a]pyridine ring at its 4 position.

In yet another embodiment, $R_3$ corresponds to structure II above, where C is unsaturated, and C, taken together with X, Y, and $R_{10}$, forms a 1H-imidazole-2-(3H)-thione, while $R_2$ is isopropyl.

In an alternative embodiment, $R_3$ corresponds to structure II above, where C is unsaturated, and C, taken together with X, Y, and $R_{10}$, forms a thiazole-2(5H)-imine, while $R_2$ is isopropyl.

In yet a further embodiment, a substituted pyrazolo[1,5-a]pyridine compound of the invention possesses the following generalized structure:

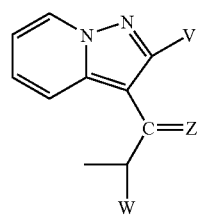

III where Z is O, N—OH, or N—O—C(O)$NH_2$; W is lower alkyl or amino; and V is lower alkyl or substituted phenyl. In one embodiment, V is mono-substituted phenyl, where the substituents can be ortho, meta or para. In a particular embodiment when V is mono-substituted phenyl, the substituents are para to one another.

In a particular embodiment of structure III, W is —$CH_3$ or —$NH_2$, and V is isopropyl or 4-fluorophenyl.

In one preferred embodiment of structure III, Z is O, W is —$NH_2$, and V is isopropyl.

In yet another preferred embodiment of structure III, Z is N—O—C(O)$NH_2$, W is methyl, and V is isopropyl.

In yet a further preferred embodiment of structure III, Z is N—OH, W is methyl, and V is 4-fluorophenyl.

In yet another embodiment, $R_6$ is —H or an organic radical selected from the group consisting of hydroxy, lower alkoxy, lower alkyl, and substituted lower alkyl. Exemplary substituted lower alkyl groups include halomethyl, dihalomethyl, and trihalomethyl, among others.

In yet another embodiment, provided is a compound having the structure shown below,

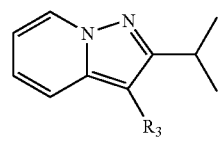

IV where $R_3$ is selected from:

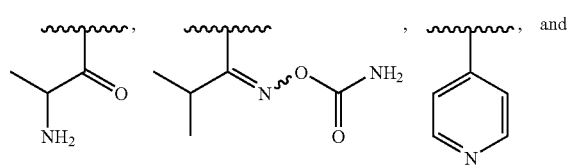

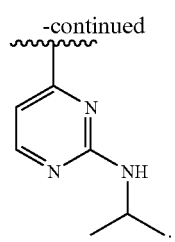

Preferred substituted pyrazolo[1,5-a]pyridine compounds of the invention include compounds corresponding to the following designations used herein: 1001, 1002, 1003, 1004, 1005, 1006, 1007, 1008, 1009, 1012, 1013, 1014, 1015, 1016, 1017, 1018, 1019, 1020, 1021, 1022, 1023, 1024, 1025, 1026, 1027, 1032, 1033, 1103, 1137, 1085, and 1087.

In a preferred embodiment, referring to structure I above, $R_3$ is selected from alkyl, substituted alkyl, alkanoyl (also referred to as acyl), and substituted alkanoyl.

In yet another embodiment, $R_3$ is selected from lower alkyl, substituted lower alkyl, lower alkanoyl, and substituted alkanoyl.

Particularly preferred $R_3$ moieties include (i) lower alkanoyls substituted with one or more polar substituents such as hydroxy, alkoxy, amino, and cyano, and (ii) alkyl oximes. Exemplary $R_3$ moieties include 2-aminoethanone, 2-amino-propan-1-one, 2-methylpropan-1-one oxime, and 2-methylpropan-1-one-O-carbamoyl oxime.

In a particularly preferred embodiment, $R_2$ is isopropyl, $R_3$ is selected from 2-aminoethanone, 2-amino-propan-1-one, 2-methylpropan-1-one oxime, and 2-methylpropan-1-one-O-carbamoyl oxime, and $R_6$ is H.

Illustrative compounds in accordance with the invention are provided in Table 1, as well as in the accompanying examples. That is to say, one particular embodiment of the invention include compounds in accordance with structure I above, where each of $R_2$, $R_3$ and $R_6$ is selected from the structures provided in Table 1.

In yet another embodiment, particular compounds of the invention include those in which each of $R_2$, $R_3$, and $R_6$ possesses the individual structure provided in Table 1, for each of the respective substituted pyrazolo[1,5-a]pyridine compounds provided therein.

In yet another embodiment, a substituted pyrazolo[1,5-a]pyridine compound is selected from compounds 1013 (2-amino-1-(2-isopropylpyrazolo[1,5-a]pyridin-3-yl)propan-1-one), 1014 (1-(2-isopropylpyrazolo[1,5-a]pyridin-3-yl)-2-methylpropan-1-one O-carbamoyl oxime), 1019 (1-(2-(4-fluorophenyl)pyrazolo[1,5-a]pyridin-3-yl)-2-methylpropan-1-one oxime), 1103 (2-Isopropyl-3-pyridin-4-yl-pyrazolo[1,5-a]pyridine), 1137 (isopropyl-[4-(2-isopropylpyrazolo[1,5-a]pyridin-3-yl)-pyrimidin-2-yl]-amine, 1085 (4-(2-isopropylpyrazolo[1,5-a]pyridin-3-yl)-1H-imidazole-2(3H)-thione), and 1087 (4-(2-isopropylpyrazolo[1,5-a]pyridin-3-yl)thiazol-2(5H)-imine).

The present invention also encompasses pharmaceutically acceptable salt forms and prodrugs of the foregoing compounds.

The present invention further provides a pharmaceutical composition comprising a 2,3,6-substituted pyrazolo[1,5-a]pyridine compound as described above. Such compositions may optionally include one or more pharmaceutically acceptable excipients.

In yet another aspect, provided herein is a method for preparing a 2,3,-substituted pyrazolo[1,5-a]pyridine compound. The method comprises the step of acylating a 2-substituted pyrazolo[1,5-a]pyridine under conditions effective to provide a pyrazolo[1,5-a]pyridine compound comprising an acyl group at the 3-ring position ("2-substituted, 3-alkanoyl pyrazolo[1,5-a]pyridine"). The reactant, a 2-substituted pyrazolo[1,5-a]pyridine, typically possesses a moiety at the 2-ring position selected from alkyl, substituted alkyl, aryl, substituted aryl, alkenyl, substituted alkenyl, alkynyl, substituted alkynyl, hydroxy, sulfhydryl, alkoxy, substituted alkoxy, aryloxy, substituted aryloxy, alkanoyl, carbamoyloxy, thioalkyl, substituted thioalkyl, carbamoylthio, thioaryl, substituted thioaryl, amino, halo, and carbamoylamino. Preferred 2-substituents include lower alkyl, substituted lower alkyl, aryl, substituted aryl, alkoxy, halo, and alkanoyl. Particularly preferred 2-substituents include methyl, ethyl, propyl, isopropyl, tert-butyl, sec-butyl, phenyl, halophenyl, and methoxyphenyl.

In the above method, the 2-substituted, 3-alkanoyl pyrazolo[1,5-a]pyridine is optionally further transformed into one or more desired 2,3,-substituted pyrazolo[1,5-a]pyridine compounds. For example, the resulting ketone functionality may be reduced to an alcohol, or even an alkyl group, e.g., using the Clemmensen reduction. Alternatively, the keto group may be converted to an oxime or to an imine or hydrazone. In yet another approach, the 3-alkanoyl pyrazolo[1,5-a]pyridine may be prepared to contain a leaving group, e.g., a halo group or other suitable functionality, to allow yet further transformations. In a preferred approach, an α-halo ketone is prepared from the acylation reaction.

In a particular embodiment of the method, the acylation reaction is a Friedel Crafts acylation.

In yet another embodiment, the acylation reaction comprises reacting a 2-substituted pyrazolo[1,5-a]pyridine with an α-halo alkanyol chloride in the presence of aluminum chloride to provide a 2-substituted, 3-(α-haloalkanoyl)pyrazolo[1,5-a]pyridine. In yet a further embodiment, the 2-substituted, 3-(α-haloalkanoyl)pyrazolo[1,5-a]pyridine is then reacted with a suitable nucleophilic reagent to replace the α-halo group with a new functionality, e.g., an amino group, a nitrile group, a hydroxyl group, or the like.

In yet another aspect, the compounds of the invention are useful in the treatment of neuropathic pain, as evidenced by results using standard neuropathic pain models. The compounds of the invention have been found to be effective in significantly attenuating mechanical allodynia. Thus, also provided herein is a method for treating a mammalian subject experiencing neuropathic pain by administering to the subject a therapeutically effective amount of a substituted pyrazolo[1,5-a]pyridine compound as described herein. As a result of such administering, the subject experiences relief (i.e., attenuation or reduction, elimination, or reversal) of the neuropathic pain.

Mammalian subjects for treatment include those suffering from postherpetic neuralgia, trigeminal neuralgia, diabetic neuropathy, and neuropathic pain associated with a condition selected from the group consisting of migraine, herpes, HIV, traumatic nerve injury, stroke, post-ischemia, fibromyalgia, reflex sympathetic dystrophy, complex regional pain syndrome, and cancer-chemotherapeutic-induced neuropathic pain (e.g., taxol-induced neuropathy).

In a preferred embodiment of the treatment method, the administering is over a duration of time effective to result in attenuation or elimination of the neuropathic pain.

In a further embodiment of the method, a substituted pyrazolo[1,5-a]pyridine compound as described above is administered in combination with at least one other agent effective for treating pain. Such agents include gabapentin, memantine, pregabalin, morphine and related opiates, cannabinoids, tramadol, lamotrigine, carbamazepine, duloxetine, milnacipran, and tricyclic antidepressants, among others.

In yet another aspect, the compounds of the invention are inhibitors of phosphodiesterases.

Further, in yet another aspect, the compounds of the invention are particularly effective in inhibiting cytokine release using a standard in-vitro peripheral blood mononuclear cell assay. More particularly, the compounds of the invention are effective in inhibiting the production of TNF-α and IL-1β. Thus also provided herein is a method for treating inflammation by administering to a subject suffering from an inflammatory condition a therapeutically effective amount of a substituted pyrazolo[1,5-a]pyridine compound of the invention.

In yet another aspect, provided herein is a method for treating opioid withdrawal or opioid dependence by administering to a subject suffering from the same a therapeutically effective amount of a substituted pyrazolo[1,5-a]pyridine compound of the invention.

In yet another aspect, provided herein are methods for (i) attenuating or abolishing the dopamine mediated "reward" associated with addicts' cravings, as well as (ii) alleviating symptoms of withdrawal syndromes after discontinuance of drug use or compulsive behavior.

Specifically, provided herein is a method for suppressing the release of dopamine in the nucleus accumbens of a subject comprising administering to the subject an effective amount of a pyrazolo[1,5-a]pyridine compound of the invention.

In certain embodiments, the subject has an addiction. In certain embodiments, the addiction is a drug addiction, for example, an opiate, cocaine, amphetamine, methamphetamine, cannabinoid, alcohol, or nicotine addiction. In other embodiments, the addiction is a behavioral addiction, for example, an eating, drinking, smoking, shopping, gambling, sex, or computer use addiction.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

DETAILED DESCRIPTION

Figure 1:
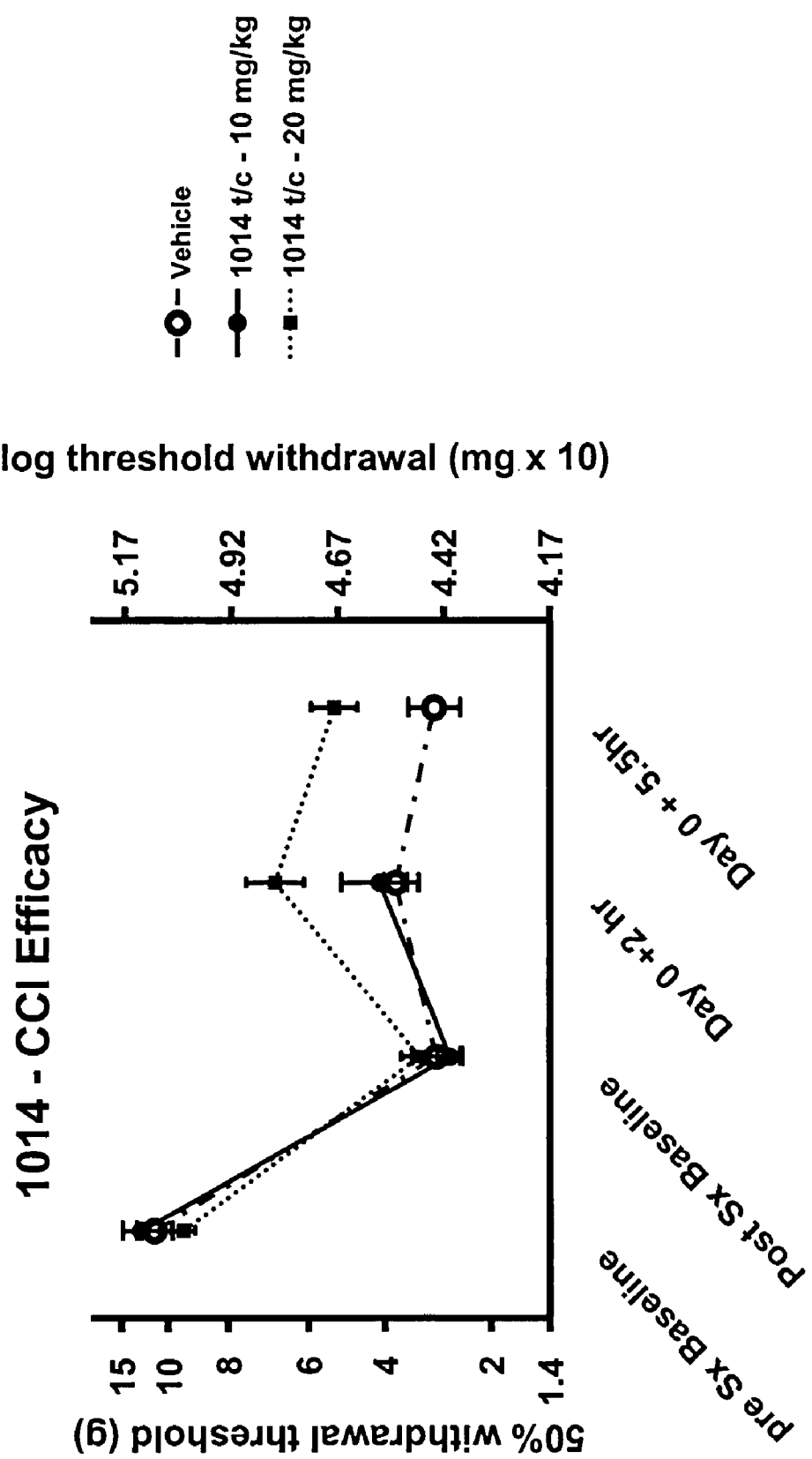
FIG. 1 is a plot demonstrating the results of an illustrative compound of the invention in a rat chronic constriction injury model for assessing efficacy in treatment of neuropathic pain as described in detail in Example 72. The model employed measures mechanical allodynia by response to von Frey Fibers. The plot shows the 50% paw withdrawal threshold (in grams) for rats administered vehicle or compound 1014 intraperitoneally at two different doses at various time points post-administration.

The practice of the present invention will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., $20^{th}$ Ed.; *Goodman & Gilman The Pharmacological Basis of Therapeutics*, J. Griffith Hardman, L. L. Limbird, A. Gilman, $10^{th}$ Ed.

All publications, patents and patent applications cited herein, whether supra or infra, are hereby incorporated by reference in their entirety.

DEFINITIONS

Before describing the present invention in detail, it is to be understood that this invention is not limited to particular embodiments, as such may vary, as will be apparent from the accompanying description, examples, and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present invention, the following terminology will be used in accordance with the definitions described below. The following definitions are meant to apply regardless of whether a term is used by itself or in combination with another term. That is to say, the definition of "alkyl" applies to "alkyl" as well as to the "alkyl" portions of "alkoxy", "alkylamino", etc.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, isopropyl, butyl, pentyl, 1-methylbutyl, 1-ethylpropyl, 3-methylpentyl, and the like. As used herein, "alkyl" includes cycloalkyl when three or more carbon atoms are referenced.

"Lower" in reference to a particular functional group means a group having from 1-6 carbon atoms.

For example, "lower alkyl" refers to an alkyl group containing from 1 to 6 carbon atoms, and may be straight chain or branched, as exemplified by methyl, ethyl, propyl, isopropyl, 1-ethylpropyl, 1,2-dimethylpropyl, n-butyl, i-butyl, sec-butyl, t-butyl, and the like.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

The term "alkylene" includes straight or branched alkylene chains such as methylene, ethylene, trimethylene, tetramethylene, pentamethylene, hexamethylene, and the like.

"Non-interfering substituents" are those groups that, when present in a molecule, are typically non-reactive with other functional groups contained within that molecule.

The term "substituted" as in, for example, "substituted alkyl" or "substituted aryl" refers to a moiety (e.g., an alkyl or aryl group) substituted with one or more non-interfering substituents, such as, but not limited to: $C_3$-$C_8$ cycloalkyl (e.g., cyclopropyl, cyclobutyl, and the like), halogen, (e.g., fluoro, chloro, bromo, and iodo), cyano, oxo, acyl, ester, sulfhydryl, amino, thioalkyl, carbonyl, carboxyl, carboxamido, alkoxy, lower alkyl, aryl, substituted aryl, phenyl, substituted phenyl, cyclic amides (e.g., cyclopentamide, cyclohexamide, etc., morpholinamide, tetrahydroquinolineamide, tetrahydroisoquinolineamide, coumarinamides, and the like). For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propoxy, isopropoxy, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl. Preferred aryl groups contain one or two aromatic rings.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings. Exemplary heteroaryl rings include pyridine, pyridazine, pyrrole, pyrazole, triazole, imidazole, oxazole, isoxazole, thiazole, isothiazole, tetrahyquinoline, tetrahyquinolineamide, tetrahydroisoquinoline, tetrahydroisoquinolineamide, coumarin, courmarinamide, and the like.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Amino" as used herein, encompasses both mono-substituted amino and di-substituted amino compounds. For example, amino refers to the moiety, —$NR_aR_b$, where $R_a$ and $R_b$ are each independently —H, alkyl, aryl, or alkylaryl.

Carbamoyl-derivatives, as referred to herein, e.g., carbamoyloxy, carbamoxythio, and carbamoylamino, encompass carbamoyl moieties where the amino group comprised therein may be unsubstituted, mono-substituted or di-substituted as set forth under the definition for amino group above.

The term "reactive" or "activated" when used in conjunction with a particular functional group, refers to a functional group that reacts readily with an electrophile or a nucleophile, typically present on another molecule, to undergo a transformation. This is in contrast to those groups that require strong catalysts or harsh reaction conditions in order to react (i.e., a "nonreactive" or "inert" group).

The term "protected" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *PROTECTIVE GROUPS IN ORGANIC SYNTHESIS,* 3rd ed., John Wiley & Sons, Inc., New York, N.Y. (1999).

As used herein, the term "functional group" or any synonym thereof is meant to encompass protected forms thereof.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, non-toxic salts such as amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic carboxylic or sulfonic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

By "pathological pain" is meant any pain resulting from a pathology, such as from functional disturbances and/or pathological changes, lesions, burns, injuries, and the like. One form of pathological pain is "neuropathic pain" which is pain thought to initially result from nerve damage but extended or exacerbated by other mechanisms including glial cell activation. Examples of pathological pain include, but are not limited to, thermal or mechanical hyperalgesia, thermal or mechanical allodynia, diabetic pain, pain arising from irritable bowel or other internal organ disorders, endometriosis pain, phantom limb pain, complex regional pain syndromes, fibromyalgia, low back pain, cancer pain, pain arising from infection, inflammation or trauma to peripheral nerves or the central nervous system, multiple sclerosis pain, entrapment pain, and the like.

"Hyperalgesia" means an abnormally increased pain sense, such as pain that results from an excessive sensitiveness or sensitivity. Examples of hyperalgesia include but are not limited to cold or heat hyperalgesia.

"Hypalgesia" (or "hypoalgesia") means the decreased pain sense.

"Allodynia" means pain sensations that result from normally non-noxious stimulus to the skin or body surface. Examples of allodynia include, but are not limited to, cold or heat allodynia, tactile or mechanical allodynia, and the like.

"Nociception" is defined herein as pain sense. "Nociceptor" herein refers to a structure that mediates nociception. The nociception may be the result of a physical stimulus, such as, mechanical, electrical, thermal, or a chemical stimulus. Nociceptors are present in virtually all tissues of the body.

"Analgesia" is defined herein as the relief of pain without the loss of consciousness. An "analgesic" is an agent or drug useful for relieving pain, again, without the loss of consciousness.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

"Glial cells" refer to various cells of the CNS also known as microglia, astrocytes, and oligodendrocytes.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "pharmacologically effective amount" or "therapeutically effective amount" of a composition or agent, as provided herein, refer to a nontoxic but sufficient amount of the composition or agent to provide the desired response, such as a reduction or reversal of neuropathic pain. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about", particularly in reference to a given quantity, is meant to encompass deviations of plus or minus five percent.

"Treatment" or "treating" neuropathic pain includes: (1) preventing pain, i.e. causing pain not to develop or to occur with less intensity in a subject that may be exposed to or predisposed to pain but does not yet experience or display pain, (2) inhibiting pain, i.e., arresting the development or reversing pain, or (3) relieving pain, i.e., decreasing the amount of pain experienced by the subject.

By "treating existing pain" is meant attenuating, alleviating or reversing neuropathic pain in a subject that has been experiencing pain for at least 24 hours, such as for 24-96 hours or more, such as 25 30 35 40 45 48 50 55 65 72 80 90 96 100, etc. hours. The term also intends treating pain that has been occurring long-term, such as for weeks, months or even years.

The term "addiction" is defined herein as compulsively using a drug or performing a behavior repeatedly that increases extracellular dopamine concentrations in the nucleus accumbens. An addiction may be to a drug including, but not limited to, psychostimulants, narcotic analgesics, alcohols and addictive alkaloids such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, such as barbiturates, chlordiazepoxide, and alcohols, such as ethanol, methanol, and isopropyl alcohol. The term addiction also includes behavioral addictions, for example, compulsive eating, drinking, smoking, shopping, gambling, sex, and computer use.

A subject suffering from an addiction experiences addiction-related behavior, cravings to use a substance in the case of a drug addiction or overwhelming urges to repeat a behavior in the case of a behavioral addiction, the inability to stop drug use or compulsive behavior in spite of undesired consequences (e.g., negative impacts on health, personal relationships, and finances, unemployment, or imprisonment), reward/incentive effects associated with dopamine release, and dependency, or any combination thereof.

Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal.

Substituted Pyrazolo[1,5-a]pyridines

The present invention encompasses 2,3,6-substituted pyrazolo[1,5-a]pyridine compounds. Based upon results in both standard in-vitro and in-vivo assays, the compounds of the invention have been found to be effective in treating neuropathic pain, as well as in treating inflammation. Moreover, certain compounds of the invention are inhibitors of phosphodiesterase. These and other features of the invention will now be described in the sections which follow.

The compounds of the invention can be described generally by the following structure:

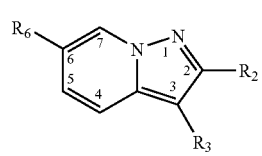

I

These compounds are referred to generally as pyrazolo[1,5-a]pyridine compounds, where the numbering of the non-bridgehead ring atoms is shown in structure I. The compounds of the invention typically possess a substituent at one or more of ring positions 2, 3, and/or 6. That is to say, a compound of the invention may possess a single substituent at position 2, a single substituent at position 3, or a single substituent at position 6. Such compounds are referred to as mono-substituted pyrazolo[1,5-a]pyridines. Alternatively, a compound of the invention may be 2,3-disubstituted, 2,6-disubstituted, or 3,6-disubstituted. Further, a compound of the invention may be 2,3,6-trisubstituted, where each of the substituents is independently selected. Preferably, a compound in accordance with the invention is one where when $R_2$ is isopropyl and $R_3$ is 2-methylpropan-1-one, then $R_6$ is not H.

Generally, in reference to structure I above, $R_2$ is independently H or an organic radical selected from the group consisting of alkyl, substituted alkyl, aryl, substituted aryl, alkenyl, substituted alkenyl, alkynyl, substituted alkynyl, hydroxy, sulfhydryl, alkoxy, substituted alkoxy, aryloxy, substituted aryloxy, carbamoyloxy, thioalkyl, substituted thioalkyl, carbamoylthio, thioaryl, substituted thioaryl, amino, and carbamoylamino;

$R_3$ is independently H or an organic radical selected from the group consisting of alkyl, substituted alkyl, aryl, substituted aryl, alkenyl, substituted alkenyl, alkynyl, and substituted alkynyl; and $R_6$ is independently H or an organic radical selected from the group consisting of hydroxy, sulfhydryl, alkoxy, aryloxy, thioalkyl, thioaryl, amino, halogen, alkyl, alkenyl, alkynyl, aryl, cyano, carboxyl, and carboxamido. Illustrative carboxamido moieties include both linear amido moieties as well as lactams, morpholinamides, tetrahydroquinolineamides, tetrahydroisoquinolineamides, coumarinamides, and the like. Preferably, $R_6$ is H.

Preferred embodiments of $R_2$ include lower alkyl, substituted lower alkyl, aryl, and substituted aryl. Representative lower alkyl groups include methyl, ethyl, propyl, isopropyl, 1-ethylpropyl, 1,2-dimethylpropyl, 1-ethyl-2-methylpropyl, 2-ethyl-1-methylpropyl, butyl, isobutyl, sec-butyl, tert-butyl, 1-methylbutyl, 2-methylbutyl, 1,1-dimethylbutyl, 1,2-dimethylbutyl, 1,3-dimethylbutyl, 2,3-dimethylbutyl, 2,2-dimethylbutyl, 3,3-dimethylbutyl, 1-ethylbutyl, 2-ethylbutyl, 2,2-dimethylbutyl, 3,3-dimethylbutyl, pentyl, isopentyl, neopentyl, tert-pentyl, 1-methylpentyl, 2-methylpentyl, 3-methylpentyl, hexyl, and isohexyl. Preferred lower alkyl and substituted lower alkyl groups include the foregoing, optionally substituted with one or more of the following: hydroxyl, cyano, hydroxyimino, carbamoyloxy, and halo. Particularly preferred $R_2$ groups include lower alkyl, substituted lower alkyl such as mono-substituted lower alkyl, e.g., isopropyl and 2-hydroxypropan-2-yl, amino, aryl, and substituted aryl.

Representative aryl groups and substituted aryl groups include phenyl, benzyl, diphenyl, napthyl, tetrahydronapthyl, indanyl, indenyl and substituted forms thereof. Illustrative aryl groups include phenyl, mono-substituted phenyl, di-substituted phenyl, and tri-substituted phenyl. In a particular embodiment, $R_2$ is a phenyl ring possessing either a single halogen or alkoxy substituent. Preferred $R_2$ substituents include 4-halo phenyl groups such 4-fluorophenyl, 4-chlorophenyl, and 4-iodophenyl, as well as 4-alkoxy phenyl substituents, where alkoxy is preferably lower alkoxy.

In certain instances, $R_3$ possesses the structure:

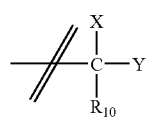

where

// represents the pyrazolo[1,5-a]pyridine ring system, where the carbon indicated is attached to ring carbon 3, and C can be saturated or unsaturated.

In the event that C in structure II is saturated, X and Y are each independently selected from the group consisting of —H or an organic radical selected from the group consisting of hydroxyl, amino, alkoxy, cyano, halo, sulfhydryl, thioalkyl, lower alkyl, and substituted lower alkyl.

When C (referring to structure II above) is unsaturated, X and Y, when taken together, form a double bond attached to a functional group, Z, selected from O, S, and N—$R_{11}$, where $R_{11}$ is selected from —OH, —O—C(O)—N$R_{12}R_{13}$, —O—C(O)—$R_{14}$, and C$R_{15}R_{16}$ and $R_{12}$, $R_{13}$, $R_{14}$ and $R_{15}$ are each independently selected from —H, lower alkyl, and aryl. Thus, when C is unsaturated, X and Y, when taken together with the carbon atom, may form one or more of the following moieties: ~C=O, ~C=S, ~C=N—OH, ~C=N—O—C(O)—N$R_{12}R_{13}$, ~C=N—O—C(O)—$R_{14}$, ~C=C$R_{15}R_{16}$, among others. In a preferred embodiment, $R_{12}$ and $R_{13}$ are both hydrogen.

In reference to structure II above, $R_{10}$ is independently H or an organic radical selected from alkyl, substituted alkyl, aryl, substituted aryl, alkenyl, substituted alkenyl, alkynyl, substituted alkynyl, and ester. In a preferred embodiment, $R_{10}$ is lower alkyl or substituted lower alkyl. Exemplary substituents such as these include isopropyl and 2-hydroxyisopropyl, among others. In yet another embodiment $R_{10}$ is an ester, e.g., a lower alkyl ester.

Alternatively, in reference to structure II, when C is unsaturated, X and Y, when taken together, form a double bond to C that, when taken together with R10, forms part of an aromatic heterocycle, preferably a nitrogen-containing heterocycle. For example, C, together with X, Y, and $R_{10}$ may form part of a pyridine ring, a pyrazole ring, a pyrimidine ring, a pyridazine ring, and the like, including substituted versions thereof. Preferred substituents are lower alkyl and halo.

In one representative example, $R_3$ corresponds to structure II above, where C is unsaturated, and C, taken together with X, Y, and $R_{10}$, forms a 3-pyridin-4-yl substituent, while $R_2$ is isopropyl.

In yet another illustrative example, $R_3$ corresponds to structure II above, where C is unsaturated, and C, taken together with X, Y, and $R_{10}$, forms a substituted pyrimidine ring having a substituent at the 2-position of the pyrimidine ring, while $R_2$ is isopropyl. In a particular embodiment thereof, the substituent at the 2-position of the pyrimidine ring is an isopropylamino group. Preferably, the pyrimidine ring is attached to the core pyrazolo[1,5-a]pyridine ring at its 4 position.

A substituted pyrazolo[1,5-a]pyridine compound of the invention may also possesses the following generalized structure:

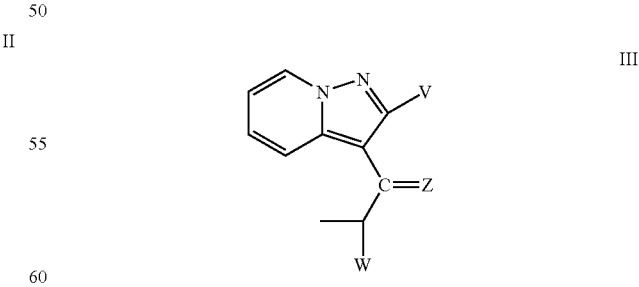

where Z is O, N—OH, or N—O—C(O)NH$_2$; W is lower alkyl or amino; and V is lower alkyl or substituted phenyl. In one embodiment, V is mono-substituted phenyl, where the substituents can be ortho, meta or para. In a particular embodiment when V is mono-substituted phenyl, the substituents are para. Further representative structures in accordance with structure III include those where: (i) W is —CH₃ or —NH₂, and V is isopropyl or 4-fluorophenyl, (ii) Z is O, W is —NH₂, and V is isopropyl, (iii) Z is N—O—C(O)NH₂, W is methyl, and V is isopropyl, and (iv) Z is N—OH, W is methyl, and V is 4-fluorophenyl.

Returning now to the moiety, R₆, R₆, may, in one or more embodiments, be —H or an organic radical selected from the group consisting of hydroxy, lower alkoxy, lower alkyl, and substituted lower alkyl. Exemplary substituted lower alkyl groups include halomethyl, dihalomethyl, and trihalomethyl, among others.

Yet another illustrative compound is one having the structure shown below,

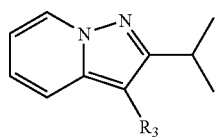

IV where R₃ is selected from:

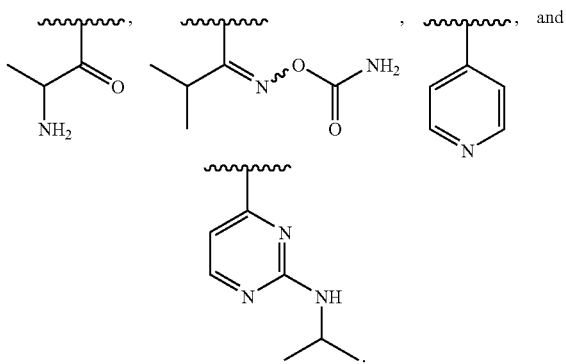

Yet another exemplary substituted pyrazolo[1,5-a]pyridine compound possesses the following generalized structure:

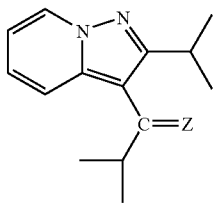

III-a where Z is O, N—OH, or N—O—C(O)NH₂.

Returning to structure I above, in reference to the moiety R₃, exemplary R₃ groups include alkyl, substituted alkyl, alkanoyl (also referred to as acyl), and substituted alkanoyl. For instance, representative R₃ moieties include lower alkyl, substituted lower alkyl, lower alkanoyl, and substituted alkanoyl. Particularly preferred R₃ moieties include (i) lower alkanoyls substituted with one or more polar substituents such as hydroxy, alkoxy, amino, and cyano and (ii) alkyl oximes.

Illustrative R₃ groups include 2-methylpropan-1-one, 2-hydroxy-2-methylpropan-1-one, 2-aminoethanone, 2-methylpropan-1-one oxime, 2-methylpropan-1-one-O-carbamoyl oxime, 4-chlorophenylmethanone, 4-methoxyphenylmethanone, propan-1-one, 2-methylpropan-1-ol, and 2-methylprop-1-enyl isobutyrate, 2-amino-propan-1-one, and 2-methylpropan-1-one-O-carbamoyl oxime, among others.

In certain instances, R₆ is —H or an organic radical selected from the group consisting of hydroxy, lower alkoxy, lower alkyl, and substituted lower alkyl. Exemplary substituted lower alkyl groups include halomethyl, dihalomethyl, and trihalomethyl, among others.

Preferably, at least one of R₂, R₃, and R₆ is a substituent other than hydrogen.

Preferred substituted pyrazolo[1,5-a]pyridine compounds of the invention include compounds corresponding to the following designations used herein: 1001, 1002, 1003, 1004, 1005, 1006, 1007, 1008, 1009, 1012, 1013, 1014, 1015, 1016, 1017, 1018, 1019, 1020, 1021, 1022, 1023, 1024, 1025, 1026, 1027, 1032, 1033, 1085, 1087, 1103, and 1137. The structures corresponding to each of the preceding compound designations is provided in the accompanying examples, and in Table 1.

In a particularly preferred embodiment, R₂ is isopropyl, R₃ is selected from 2-aminoethanone, 2-amino-propan-1-one, 2-methylpropan-1-one oxime, and 2-methylpropan-1-one-O-carbamoyl oxime, and R₆ is H.

Particularly preferred substituted pyrazolo[1,5-a]pyridine compounds include: 1013 (2-amino-1-(2-isopropylpyrazolo[1,5-a]pyridin-3-yl)propan-1-one), 1014 (1-(2-isopropylpyrazolo[1,5-a]pyridin-3-yl)-2-methylpropan-1-one O-carbamoyl oxime), 1019 (1-(2-(4-fluorophenyl)pyrazolo[1,5-a]pyridin-3-yl)-2-methylpropan-1-one oxime), 1103 (2-Isopropyl-3-pyridin-4-yl-pyrazolo[1,5-a]pyridine), and 1137 (isopropyl-[4-(2-isopropylpyrazolo[1,5-a]pyridin-3-yl)-pyrimidin-2-yl]-amine.

Particular embodiments corresponding to each of R₂, R₃ and R₆ are provided in Table 1 and in the accompanying examples.

As stated previously, a reference to any one or more of the herein-described substituted pyrazolo[1,5-a]pyridines is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), and metabolites.

Method of Synthesizing Pyrazolo[5-α]pyridines

The 2,3,6-substituted pyrazolo[1,5-a]pyridine compounds of the invention are prepared using conventional synthetic organic chemistry techniques. Illustrative syntheses are provided in at least Examples 1-71 and 75-78 herein.

One preferred method for preparing a 2,3,-substituted pyrazolo[1,5-a]pyridine compound of the invention comprises the step of acylating a 2-substituted pyrazolo[1,5-a] pyridine under conditions effective to provide a pyrazolo[1,5-a]pyridine compound comprising an acyl group at the 3-ring position i.e., a "2-substituted, 3-alkanoyl pyrazolo[1,5-a]pyridine". The reactant, a 2-substituted pyrazolo[1,5-a] pyridine, typically possesses a moiety at the 2-ring position selected from alkyl, substituted alkyl, aryl, substituted aryl, alkenyl, substituted alkenyl, alkynyl, substituted alkynyl, hydroxy, sulfhydryl, alkoxy, substituted alkoxy, aryloxy, substituted aryloxy, alkanoyl, carbamoyloxy, thioalkyl, substituted thioalkyl, carbamoylthio, thioaryl, substituted thioaryl, amino, halo, and carbamoylamino. Preferred 2-substituents include lower alkyl, substituted lower alkyl, aryl, substituted aryl, alkoxy, halo, and alkanoyl. Particularly preferred 2-substituents include methyl, ethyl, propyl, isopropyl, tert-butyl, sec-butyl, phenyl, halophenyl, and methoxyphenyl.

In the above-described method, the 2-substituted, 3-alkanoyl pyrazolo[1,5-a]pyridine is optionally further transformed into one or more desired 2,3,-substituted pyrazolo[1,5-a]pyridine compounds. For example, the resulting keto functionality may be reduced to an alcohol, or even an alkyl group, e.g., using the Clemmensen reduction. Alternatively, the keto group may be converted to an oxime or to an imine or hydrazone. In yet another approach, the 3-alkanoyl pyrazolo[1,5-a]pyridine may be prepared to contain a leaving group, e.g., a halo group or other suitable functionality, to allow yet further transformations. In a preferred approach, the acylation reaction results in formation of an α-halo ketone.

In a particularly preferred embodiment of the method, the acylation reaction is a Friedel Crafts acylation. Generally, such reactions are carried out by reacting an arene such as a pyrazolo[1,5-a]pyridine with an acyl chloride or anhydride in the presence of a suitable Lewis acid catalyst such as AlCl₃. Other Lewis acid catalysts such as metal triflates can also be used, e.g., lighter lanthanide III triflates—Sc, Y, In, La, Ce, Pr, Dy, Er, Yb, Bi, and Th. The method is effective to provide acylation at only one position of the pyrazolo[1,5-a]pyridine ring system. For instance, for a 2-substituted pyrazolo[1,5-a]pyridine (e.g., having an alkyl, substituted alkyl, aryl, substituted aryl, alkoxy, ester, or halo substituent or the like at position 2), Friedel Crafts acylation with an acid chloride or anhydride typically results in introduction of an acyl group at the 3 ring-position, due to the presence of the bridgehead nitrogen in the ring system.

In one preferred approach, the acylation reaction is carried out by reacting a 2-substituted pyrazolo[1,5-a]pyridine with an α-halo alkanoyl chloride in the presence of a Lewis acid catalyst such as aluminum chloride to provide a 2-substituted, 3-α-haloalkanoyl)pyrazolo[1,5-a]pyridine. The resulting 2-substituted, 3-(α-haloalkanoyl)pyrazolo[1,5-a]pyridine may then optionally be further transformed into a desired product, e.g., by reaction with a suitable nucleophilic reagent to replace the α-halo group with a new functionality, e.g., an amino group, a nitrile group, a hydroxyl group, or the like.

Alternatively, to prepare an oxime-carbamate substituted pyrazolo[1,5-a]pyridine, the acylation reaction is carried out by reacting a substituted pyrazolo[1,5-a]pyridine with an alkanoyl chloride in the presence of a Lewis acid catalyst to provide the corresponding acyl derivative. The acyl group is then transformed into the corresponding oxime. Transformation of the oxime to the corresponding oxime-carbamate may be effected by reacting the oxime with a reagent such as imidazole-1-carboxamide, where one or both amido nitrogens are optionally substituted with an alkyl, substituted alkyl, aryl, or substituted aryl group. The imidazole-1-carboxamide reagent is typically generated from the precursor amine and carbonyldi-imidazole in the presence of a catalytic amount of a weak base such as imidazole, triazole, triethylamine, pyridine, and the like. The reaction is typically carried out in an organic solvent such as tetrahydrofuran, dioxane or a chlorinated hydrocarbon such as dichloromethane.

Additional illustrative synthetic approaches for preparing substituted pyrazolo[1,5-a]pyridine compounds are provided in the accompanying examples. In particular, provided are exemplary approaches for introducing particular types of substituents at the 2, 3, and/or 6 position(s) of the core pyrazolo[1,5-a]pyridine ring structure.

Reaction products are typically purified using any of a number of conventional purification techniques for organic compounds including recrystallization, distillation, column chromatography, thin layer chromatography, high performance liquid chromatography, and the like. Any of a number of chromatographic columns and packing materials may be employed, depending upon the particular components to be separated and the features of the desired product. Chromatographic techniques include normal phase, reverse phase, size exclusion, ion exclusion, and ion exchange chromatography. For separations of enantiomers, chiral chromatography or chiral HPLC may be employed using chiral columns such as those available from Regis Technologies, Inc., and Chromtech. See e.g., Gubitz, G., and Schmid, M. G., Eds. *Methods in Molecular Biology*, Vol. 243, *Chiral Separations Methods and Protocols*, Humana Press.

Products are typically identified using any of a number of analytical techniques such as NMR spectroscopy, mass spectrometry, IR, elemental analysis, etc.

Methods of Use

Based upon results using a standard animal model as described herein, the inventors have discovered that the administration of certain substituted pyrazolo[1,5-a]pyridines is surprisingly effective in providing a measurable reduction in the severity of neuropathic pain, and in particular, in providing a measurable reduction in the severity of certain types of neuropathic pain such as mechanical allodynia. Moreover, certain compounds as provided herein are particularly effective in inhibiting lipopolysaccharide-induced cytokine production, thus providing an indication of their efficacy in treating inflammatory conditions. In addition, certain compounds of the invention are effective phosphodiesterase inhibitors. Thus, based upon the pharmacological data provided herein (see Table 2), it is believed that the compounds of the invention are particularly effective in treating one or more of the following conditions.

The compounds of the invention are useful in treating neuropathic pain associated with certain syndromes such as viral neuralgias (e.g., herpes, AIDS), diabetic neuropathy, phantom limb pain, stump/neuroma pain, post-ischemic pain (stroke), fibromyalgia, reflex sympathetic dystrophy (RSD), complex regional pain syndrome (CRPS), cancer pain, vertebral disk rupture, spinal cord injury, and trigeminal neuralgia, cancer-chemotherapy-induced neuropathic pain, and migraine, among others.

Additionally, the compounds of the invention may be useful in treating opiate tolerance and withdrawal, and/or as antiviral agents.

The compounds provided herein may also be useful in treating depression.

Further, the compounds of the invention may be useful in suppressing the release of dopamine in the nucleus accumbens of a subject. Dopamine release in the nucleus accumbens is thought to mediate the "reward" motivating drug use and compulsive behavior associated with addictions.

Thus, the compounds of the invention may be used to attenuate or abolish the dopamine mediated "reward" associated with addictions, thus diminishing or eliminating cravings associated with addictions and the accompanying addiction-related behavior and withdrawal syndromes of a subject.

In certain embodiments, a therapeutically effective amount of a pyrazolo[1,5-a]pyridine compound of the invention is administered to a subject to treat a drug addiction. The subject may be addicted to one or more drugs including, but not limited to, psychostimulants, narcotic analgesics, alcohols and addictive alkaloids, such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, including, but not limited to, barbiturates, chlordiazepoxide, and alcohols, such as ethanol, methanol, and isopropyl alcohol.

In yet other embodiments, a therapeutically effective amount of a compound of the invention is administered to a subject to treat a behavioral addiction. A behavioral addiction can include, but is not limited to, compulsive eating, drinking, smoking, shopping, gambling, sex, and computer use.

A subject suffering from an addiction experiences addiction-related behavior, cravings to use a substance in the case of a drug addiction or overwhelming urges to repeat a behavior in the case of a behavioral addiction, the inability to stop drug use or compulsive behavior in spite of undesired consequences (e.g., negative impacts on health, personal relationships, and finances, unemployment, or imprisonment), reward/incentive effects associated with dopamine release, and dependency, or any combination thereof.

Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal. The compounds provided herein may be useful for treating addiction-related behavior as described above.

Particularly preferred compounds in accordance with the above-described uses include compounds 1013, 1014, 1019, 1103, and 1137.

In yet another aspect, certain compounds of the invention are effective inhibitors of TNF-α and/or IL-1β. Based upon their ability to inhibit the production of lipopolysaccharide-induced production of TNF-α and IL-1β, the compounds of the invention may also be useful in treating any of a number of inflammatory conditions. Representative inflammatory disorders that may be treated by administering a compound of the invention include rheumatoid arthritis, bronchitis, tuberculosis, chronic cholecystitis, inflammatory bowel disease, acute pancreatitis, sepsis, asthma, chronic obstructive pulmonary disease, dermal inflammatory disorders such as psoriasis and atopic dermatitis, systemic inflammatory response syndrome (SIRS), acute respiratory distress syndrome (ARDS), cancer-associated inflammation, reduction of tumor-associated angiogenesis, osteoarthritis, diabetes, treatment of graft v. host disease and associated tissue rejection, Crohn's disease, delayed-type hypersensitivity, immune-mediated and inflammatory elements of CNS disease; e.g., Alzheimer's, Parkinson's, multiple sclerosis, etc.

In examining the pharmacological activity of the compounds of the invention, it has been discovered that certain substituted pyrazolo[1,5-a]pyridines are particularly effective in inhibiting phosphodiesterase (PDE). See Example 73, which describes an illustrative assay for assessing phosphodiesterase inhibition. Phosphodiesterases regulate the intracellular levels of secondary messengers, cAMP and cGMP, which affects cellular signaling. Therapeutic indications for PDE inhibitors include hypertension, congestive heart failure, thrombosis, glaucoma, asthma, autoimmune disease and inflammation. Thus, any one or more of the foregoing conditions may be treated by administering a pyrazolo[1,5-a]pyridines compound of the invention. Particularly preferred phosphodiesterase inhibitors as provided herein include compounds 1004, 1006, 1008, 1012, 1019, 1022, 1024, 1025, and 1026.

Additionally, the compounds provided herein may be used for treating opioid withdrawal syndrome in a mammalian subject. That is to say, in another aspect, provided herein is a method of treating an opioid withdrawal syndrome in a mammalian subject by administering one or more of the substituted pyrazolo[1,5-a]pyridines described herein. Exemplary opioids include but are not limited to morphine and methadone.

Opioid-driven progressive glial activation causes glia to release neuroexcitatory substances, including the proinflammatory cytokines interleukin-1 (IL-1), tumor necrosis factor (TNF), and interleukin-6 (IL-6). These neuroexcitatory substances counteract the pain-relieving actions of opioids, such as morphine, and drive withdrawal symptomology, as demonstrated by experiments involving co-administration or pro- or anti-inflammatory substances along with morphine. Indeed, if morphine analgesia is established and then allowed to dissipate, potent analgesia can be rapidly reinstated by injecting IL-1 receptor antagonist, suggesting that dissipation of analgesia is caused by the activities of pain-enhancing proinflammatory cytokines rather than dissipation of morphine's analgesic effects.

The activity of other opioids may also be opposed by activation of glia. Studies show that glia and proinflammatory cytokines compromise the analgesic effects of methadone, at least in part, via non-classical opioid receptors (Hutchinson, M. R., et al. (2005) *Proc. Soc. Neurosci.*, in press). These results suggest that glia and proinflammatory cytokines will be involved in methadone withdrawal, and likely withdrawal from other opioids as well. These data also expand the clinical implications of glial activation, since cross-tolerance between opioids may be explained by the activation of the glial pain facilitatory system, which undermines all attempts to treat chronic pain with opioids.

In summary, opioids excite glia, which in turn release neuroexcitatory substances (such as proinflammatory cytokines) that oppose the effects of opioids and create withdrawal symptoms upon cessation of opioid treatment. Compounds that suppress such glial activation, such as those provided herein, may also then be beneficial novel therapeutics for treatment of opioid withdrawal.

In yet another aspect, provided herein is a method for potentiation of opioid-induced analgesia in a subject by administration of a phosphodiesterase 4 (PDE 4) inhibitor or glial attenuator such as the substituted pyrazolo[1,5-a]pyridines described herein. See, for example, Table 2. In particular, provided is a method of treating or preventing acute or subchronic pain by administration of an effective amount of a phosphodiesterase 4 (PDE 4) inhibitor or glial attenuator, such as the illustrative compounds provided herein, in combination with an opioid analgesic. The substituted pyrazolo[1,5-a]pyridine compound administered potentiates opioid-induced analgesia in the subject.

In-Vivo and In-Vitro Models

Standard in-vitro and in-vivo models may be used to assess the potential therapeutic uses of the compounds provided herein. For example, any one or more of the following standard pain models may be used to evaluate the ability of a compound such as those described herein to treat neuropathic pain.

Carrageenan-induced Paw Hyperalgesia Model: The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al., *Arch. Int. Pharmacodyn.* (1957) 111:409-419.

The effects of selected agents on carrageenan-induced paw edema can also be examined. This test (see, Vinegar et al., *J. Phamacol. Exp. Ther.* (1969) 166:96-103) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Von Frey Filament Test: The effect of compounds on mechanical allodynia can be determined by the von Frey filament test in rats with a tight ligation of the L-5 spinal nerve: a model of painful peripheral neuropathy. The surgical procedure is performed as described by Kim et al., *Pain* (1992) 50:355-363. A calibrated series of von Frey filaments are used to assess mechanical allodynia (Chaplan et al., *J. Neurosci. Methods* (1994) 53:55-63). Filaments of increasing stiffness are applied perpendicular to the midplantar surface in the sciatic nerve distribution of the left hindpaw. The filaments are slowly depressed until bending occurred and are then held for 4-6 seconds. The filament application order and number of trials were determined by the up-down method of Dixon (Chaplan et al., supra). Flinching and licking of the paw and paw withdrawal on the ligated side are considered positive responses.

Chronic Constriction Injury: Heat and cold allodynia responses as well as mechanical allodynia sensations can be evaluated as described below in rats having a chronic constriction injury (CCI). A unilateral mononeuropathy is produced in rats using the chronic constriction injury model described in Bennett et al., *Pain* (1988) 33:87-107. CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1-2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

This model is described in greater detail in Example 72. Generally, compounds of the invention exhibiting a chronic constriction injury threshold of 1.0 gram or greater are preferred for use in treating neuropathic pain, while compounds exhibiting a chronic constriction injury threshold of 1.5 grams or greater, or even more preferably 2.0 grams or greater are particularly preferred. Thus, compounds 1009, 1012, 1013, 1014, 1017, 1019, 1026, 1085, 1103, and 1137 are particularly advantageous for treating allodynia. In summary, the aforementioned compounds are particularly efficacious in treating neuropathic pain, as demonstrated using a mechanical allodynia rat model.

Chung Model of Rat Neuropathic Pain: Heat and cold allodynia responses as well as mechanical allodynia sensations can be evaluated as described below in rats following spinal nerve injury (e.g. ligation, transaction). Details are as initially described in S H Kim and J M Chung, *Pain* (1992) 50:355-363.

Cancer-Chemotherapy-Induced Neuropathy: Chemotherapy induced neuropathy using paclitaxel (taxol) is described in detail in Polomano et al., *Pain* (1994) 3:293-304. Rats become allodynic following a series of 4 intraperitoneal injections of taxol on alternating days. Heat and cold hyperalgesia can be evaluated as described below, as well as mechanical allodynia in response to von Frey filaments.

The Hargreaves Test: The Hargreaves test (Hargreaves et al., *Pain* (1998) 32:77-88) is also a radiant heat model for pain. CCI rats are tested for thermal hyperalgesia at least 10 days post-op. The test apparatus consists of an elevated heated (80-82° F.) glass platform. Eight rats at a time, representing all testing groups, are confined individually in inverted plastic cages on the glass floor of the platform at least 15 minutes before testing. A radiant heat source placed underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minutes interval between trials. The average of these values represents the withdrawal latency.

Cold Allodynia Model: The test apparatus and methods of behavioral testing is described in Gogas et al., *Analgesia* (1997) 3:111-118. The apparatus for testing cold allodynia in neuropathic (CCI) rats consists of a Plexiglass chamber with a metal plate 6 cm from the bottom of the chamber. The chamber is filled with ice and water to a depth of 2.5 cm above the metal plate, with the temperature of the bath maintained at 0-4° C. throughout the test. Each rat is placed into the chamber individually, a timer started, and the animal's response latency was measured to the nearest tenth of a second. A "response" is defined as a rapid withdrawal of the right ligated hindpaw completely out of the water when the animal is stationary and not pivoting. An exaggerated limp while the animal is walking and turning is not scored as a response. The animals' baseline scores for withdrawal of the ligated leg from the water typically range from 7-13 seconds. The maximum immersion time is 20 seconds with a 20-minute interval between trials.

Additional information regarding models of neuropathic pain is available in the following publications. Bennett G J, Xie Y K (1988) "A peripheral mononeuropathy in rat that produces disorders of pain sensation like those seen in man" *Pain* 33: 87-107; Chaplan S R, Bach F W, Pogrel J W, Chung J M, Yaksh T L (1994) "Quantitative assessment of tactile allodynia in the rat paw" *J. Neurosci. Meth.* 53: 55-63; Fox A, Gentry C, Patel S, Kesingland A, Bevan S (2003) "Comparative activity of the anti-convulsants oxcarbazepine, carbamazepine, lamotrigin and gabapentin in a model of neuropathic pain in the rat and guinea-pig" *Pain* 105: 355-362; Milligan E D, Mehmert K K, Hinde J L, Harvey L O J, Martin D, Tracey K J, Maier S F, Watkins L R (2000) "Thermal hyperalgesia and mechanical allodynia produced by intrathecal administration of the Human Immunodeficiency Virus-1 (HIV-1)

envelope glycoprotein, gp120 "*Brain Res.* 861: 105-116; De Vry J, Kuhl E, Franken-Kunkel P, Eckel G (2004) "Pharmacological characterization of the chronic constriction injury model of neuropathic pain" *Eur. J. Pharmacol.* 491:137-148. Polomano R C, Mannes A J, Clark U S, Bennett G J (2001) "A painful peripheral neuropathy in the rat produced by the chemotherapeutic drug, paclitaxel" *Pain* 94:293-304.

Models for assessing anti-inflammatory activity include the measurement of cytokine production, e.g., TNF-α, IL-1β, in lipopolysaccharide-activated peripheral blood mononuclear cells upon exposure to a test compound as described in Example 74. Results are provided in Table 2. In this regard, i.e., for use as an anti-inflammatory agent, preferred compounds are those having an $IC_{50}$ of less than or equal to about 50 μM, preferably less than about 40 μM, and even more preferably, less than about 30 μM. Thus, preferred compounds for use as anti-inflammatory agents include 1001, 1004, 1006, 1007, 1008, 1009, 1013, 1014, 1018, and 1024. Since chronic inflammatory diseases are caused by prolonged production of several proinflammatory cytokines such as TNF-α and IL-1β, the ability of a compound to effectively inhibit LPS-stimulated production of such cytokines provides an indication of its efficacy in treating one or more inflammatory conditions.

Additional assays for assessing anti-inflammatory activity are described "*Animal Models for Inflammation*", *ILAR Journal*, 40 (4), 1999. Other suitable animal models that may be employed for assessing anti-inflammatory activity include LPTA® Animal Models available from Xenogen (Alameda, Calif.), which use transgenic mice with a luciferase reporter driven by one of the following promoters: Gadd45b, iNos, IL-2, COX-2, Ptgs2, TNF-α, etc.

Methods of Administration.

The compounds of the invention may be administered either systemically or locally. Such routes of administration include but are not limited to, oral, intra-arterial, intrathecal, intraspinal, intramuscular, intraperitoneal, intravenous, intranasal, subcutaneous, and inhalation routes.

More particularly, the compounds provided herein may be administered for therapeutic use by any suitable route, including without limitation, oral, rectal, nasal, topical (including transdermal, aerosol, buccal and sublingual), vaginal, parenteral (including subcutaneous, intramuscular, intravenous and intradermal), intrathecal, and pulmonary. The preferred route will, of course, vary with the condition and age of the recipient, the particular condition being treated, and the specific combination of drugs employed, if any.

One preferred mode of administration, e.g., for treating neuropathic pain, is directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

A particularly preferred method for targeting spinal cord glia is by intrathecal delivery, rather than into the cord tissue itself.

Another preferred method for administering a substituted pyrazolo[1,5-a]pyridine-based composition of the invention, e.g., for treating neuropathic pain, is by delivery to dorsal root ganglia (DRG) neurons, e.g., by injection into the epidural space with subsequent diffusion to DRG. For example, such compositions can be delivered via intrathecal cannulation under conditions effective to diffuse the composition to the DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, the compounds of the invention can be delivered to many cells over large areas of the CNS. Any convection-enhanced delivery device may be appropriate for delivery of a substituted pyrazolo[1,5-a]pyridine of the invention. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a composition of the invention is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. For a detailed description regarding CED delivery, see U.S. Pat. No. 6,309,634, incorporated herein by reference in its entirety.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular substituted pyrazolo[1,5-a]pyridine being administered.

Therapeutically effective amounts can be determined by those skilled in the art, and will be adjusted to the requirements of each particular case. Generally, a therapeutically effective amount of a substituted pyrazolo[1,5-a]pyridine of the invention will range from a total daily dosage of about 0.1 and 1000 mg/day, more preferably, in an amount between 1-200 mg/day, 30-200 mg/day, 1-100 mg/day, 30-100 mg/day, 30-300 mg/day, 1-60 mg/day, 1-40 mg/day, or 1-10 mg/day, administered as either a single dosage or as multiple dosages. Preferred dosage amounts include dosages greater than or equal to about 10 mg BID, or greater than or equal to about 10 mg TID, or greater than or equal to about 10 mg QID. That is to say, a preferred dosage amount is greater than about 20 mg/day or greater than 30 mg/day. Dosage amounts may be selected from 30 mg/day, 40 mg/day, 50 mg/day, 60 mg/day, 70 mg/day, 80 mg/day, 90 mg/day or 100 mg/day or more. Depending upon the dosage amount and precise condition to be treated, administration can be one, two, or three times daily for a time course of one day to several days, weeks, months, and even years, and may even be for the life of the patient. Illustrative dosing regimes will last a period of at least about a week, from about 1-4 weeks, from 1-3 months, from 1-6 months, from 1-50 weeks, from 1-12 months, or longer.

Practically speaking, a unit dose of any given composition of the invention can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

In addition to comprising a substituted pyrazolo[1,5-a]pyridine of the invention, a therapeutic formulation of the invention may optionally contain one or more additional components as described below.

A composition of the invention may comprise, in addition to a substituted pyrazolo[1,5-a]pyridine, one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A substituted pyrazolo[1,5-a]pyridine-containing composition of the invention may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the invention may also contain one or more antioxidants. Antioxidants are used to prevent oxidation, thereby preventing the deterioration of the drug(s) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the invention may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the invention is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

A formulation (or kit) in accordance with the invention may contain, in addition to a substituted pyrazolo[1,5-a]pyridine of the invention, one or more additional active agents, e.g., a drug effective for treating neuropathic pain. Such actives include gabapentin, memantine, pregabalin, morphine and related opiates, cannabinoids, tramadol, lamotrigine, carbamazepine, duloxetine, milnacipran, and tricyclic antidepressants.

Gabapentin, also known as Neurontin®, is structurally related to the neurotransmitter GABA. Although structurally related to GABA, gabapentin does not interact with GABA receptors, is not converted metabolically into GABA or a GABA agonist, and is not an inhibitor of GABA uptake or degradation. Gabapentin has no activity at GABAA or GABAB receptors of GABA uptake carriers of the brain, but instead interacts with a high-affinity binding site in brain membranes (an auxiliary subunit of voltage-sensitive $Ca^{2+}$ channels). The exact mechanism of action is unknown, only that its physiological site of action is the brain. The structure of gabapentin allows it to pass freely through the blood-brain barrier. In vitro, gabapentin has many pharmacological actions including modulating the action of the GABA synthetic enzyme, increasing non-synaptic GABA responses from neural tissue, and reduction of the release of several mono-amine neurotransmitters. Daily dosages of gabapentin typically range from about 600 to 2400 mg/day, more preferably from about 900 to 1800 mg/day, and are administered in divided doses, for example, three times a day. Conventional unit dosage forms are 300 or 400 mg capsules or 600 or 800 mg tablets.

The active agent, memantine, is a receptor antagonist. Memantine is believed to function as a low to moderate affinity uncompetitive (open-channel) NMDA receptor antagonist which binds to the NMDA receptor-operated cation channels. Recommended daily dosage amounts typically range from about 5 mg to 20 mg.

The opiate, morphine, elicits its effects by activating opiate receptors that are widely distributed throughout the brain and body. Once an opiate reaches the brain, it quickly activates the opiate receptors found in many brain regions and produces an effect that correlates with the area of the brain involved. There are several types of opiate receptors, including the delta, mu, and kappa receptors. Opiates and endorphins function to block pain signals by binding to the mu receptor site.

The cannabinoids, e.g., tetrahydrocannabinol, bind to the cannabinoid receptor referred to as $CB_1$. $CB_1$ receptors are found in brain and peripheral tissues; $CB_1$ receptors are present in high quantities in the central nervous system, exceeding the levels of almost all neurotransmitter receptors. An additional cannabinoid receptor subtype termed 'CB2' has also been identified. See, e.g., Martin, B. R., et al., *The Journal of Supportive Oncology*, Vol. 2, Number 4, July/August 2004.

Although its mechanism of action has not yet been fully elucidated, the opioid, tramadol, is believed to work through modulation of the GABAergic, noradrenergic and serotonergic systems. Tramadol, and its metabolite, known as MI, have been found to bind to μ-opioid receptors (thus exerting its effect on GABAergic transmission), and to inhibit re-uptake of 5-HT and noradrenaline. The second mechanism is believed to contribute since the analgesic effects of tramadol are not fully antagonised by the k-opioid receptor antagonist naloxone. Typical daily dosages range from about 50 to 100 milligrams every 4 to 6 hours, with a total daily dosage not to exceed 400 milligrams.

Lamotrigine is a phenyltriazine that stabilizes neuronal membranes by blocking voltage-sensitive sodium channels, which inhibit glutamate and aspartate (excitatory amino acid neurotransmitter) release. The daily dosage of lamotrigine typically ranges from 25 milligrams per day to 500 mg per day. Typical daily dosage amounts include 50 mg per day, 100 mg per day, 150 mg per day, 200 mg per day, 300 mg per day, and 500 mgs per day, not exceed 700 mgs per day.

Carbamazepine acts by blocking voltage-sensitive sodium channels. Typical adult dosage amounts range from 100-200 milligrams one or two times daily, to an increased dosage of 800-1200 milligrams daily generally administered in 2-3 divided doses.

Duloxetine is a potent inhibitor of neuronal uptake of serotonin and norephinephrine and a weak inhibitor of dopamine re-uptake. Typical daily dosage amounts range from about 40 to 60 milligrams once daily, or 20 to 30 milligrams twice daily.

Milnacipran acts as a serotonin and norepinephrine reuptake inhibitor. Daily dosage amounts typically range from about 50 to 100 milligrams once or twice daily.

The dosage amounts provided above are meant to be merely guidelines; the precise amount of a secondary active agent to be administered during combination therapy with a substituted pyrazolo[1,5-a]pyridine of the invention will, of course, be adjusted accordingly and will depend upon factors such as intended patient population, the particular neuropathic pain symptom or condition to be treated, potential synergies between the active agents administered, and the like, and will readily be determined by one skilled in the art based upon the guidance provided herein.

Preferably, the compositions are formulated in order to improve stability and extend the half-life of the active agent. For example, the substituted pyrazolo[1,5-a]pyridine may be delivered in a sustained-release formulation. Controlled or sustained-release formulations are prepared by incorporating the active into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, a substituted pyrazolo [1,5-a]pyridine of the invention can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Delivery Forms

The compositions described herein encompass all types of formulations, and in particular, those that are suited for systemic or intrathecal administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, a composition of the invention is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the Ultravent® (Mallinkrodt), and the Acorn II® (Marquest Medical Products). A composition of the invention may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the invention are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the invention may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and particular type of formulation being employed, for example, for oral administration forms, the composition for oral administration may also include additional agents as sweeteners, thickeners or flavoring agents.

The compositions of the present invention may also be prepared in a form suitable for veterinary applications.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Materials and Methods

All chemical reagents, solvents, and the like referred to in the appended examples are commercially available unless otherwise indicated. All NMR data was generated by a 300 MHz NMR spectrometer manufactured by Bruker or Varian.

Example 1

Synthesis of 2-amino-1-(2-isopropylpyrazolo[1,5-a]pyridin-3-yl)ethanone

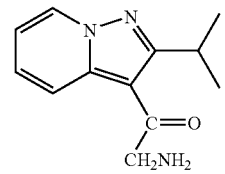

(a) Hydroxylamine-O-sulfonic acid (113 g, 11.0 mol) was dissolved in water (500 ml) and 2-methylpyridine (279 g, 3 mol) was added. The solution was stirred at 90° C. for 45 minutes, cooled in ice, and $K_2CO_3$ (138 g, 1 mol) was added in portions to control foaming. After the addition was complete, the beige suspension was evaporated to dryness on a rotary evaporator at 40-50° C., ethanol (450 ml) was added and the suspension was filtered with suction. The precipitate was washed with 150 ml of ethanol, the solution cooled in an ice/salt bath and HI (140 ml of 57%) was added slowly in small portions. Crystals separated in approximately 20 minutes, and were filtered and dried in vacuo to afford 1-amino-2-methylpyridinium iodide, 87.2 g (51%). The mother liquor was concentrated, cooled, and a second crop of crystals collected and dried to yield an additional 68.8 g (40.4%) for a combined yield of 156 g (91.4%) (K. T. Potts, et al., *J. Org. Chem.*, 33, 3766-3770 (1968)).

(b) 1-(2-isopropylpyrazolo[1,5-a]pyridin-3-yl)-2-methyl-propan-1-one. The dry salt (113 g) from Example 1 (a) was suspended in isobutyric anhydride (515 g) in a large round bottom flask equipped with a mechanical stirrer and $K_2CO_3$ (85 g) was added with stirring. The mixture was refluxed for 8 hours, cooled to room temperature and water (10 ml) was added followed by addition of $K_2CO_3$ (10 g) in portions. After the initial vigorous reaction subsided, water (500 ml) and ethyl acetate (500 ml) were added, followed by 280 g of $K_2CO_3$, added in portions with continuous mechanical stirring to control foaming. The reaction mixture was stirred for 1 hour at room temperature, 50 mL of 50% NaOH was added, and the mixture extracted with ethyl acetate (4×250 ml). Evaporation of the solution yielded a viscous oil, which was distilled under high vacuum to provide 25.2 g (32.9%) of 2-isopropylpyrazolo[1,5-a]pyridine (b.p. 45-75° C./0.25-0.5 mm Hg), and 60.4 g (51.3%) of 1-(2-isopropylpyrazolo[1,5-a]pyridin-3-yl)-2-methylpropan-1-one (b.p. 125-135° C./0.1 mm Hg; m.p. 53-55° C.) (T. Irikura, et al., U.S. Pat. No. 3,850,941, Nov. 26, 1974). Compound 411.

(c) 2-isopropylpyrazolo[1,5-a]pyridine. 1-(2-isopropylpyrazolo[1,5-a]pyridin-3-yl)-2-methylpropan-1-one (28.1 g, 120 mmol) was added to 200 ml of 50% sulfuric acid with stirring for 10-15 min., and then refluxed overnight. After cooling, the solution was neutralized with about 134 g of NaOH added portionwise, while maintaining the temperature at 0-50° C., to a final pH of 8-8.5. The mixture was extracted 3 times with ethyl acetate. The organic phase was washed with brine and dried over $MgSO_4$. The ethyl acetate was evaporated under vacuum to provide 16.07 g of 2-isopropylpyrazolo[1,5-a]pyridine (83.3%). (T. Irikura, U.S. Pat. No. 4,097,483, Jun. 27, 1978).

(d) 2-isopropyl-3-(2-chloroacetyl)pyrazolo[1,5-a]pyridine. 2.0 ml of 2-isopropylpyrazolo[1,5-a]pyridine, 2.0 ml of 2-chloroacetyl chloride and 200 mg anhydrous $AlCl_3$ were mixed with stirring at room temperature for 4 days. After cooling, 50 ml of ethyl acetate was added, followed by addition of cooled ammonia solution to pH 8-8.5 at 0-5° C. The mixture was extracted with ethyl acetate twice. The organic phase was washed with brine and dried over $MgSO_4$. The ethyl acetate was evaporated under reduced pressure to obtain 3 g of crude compound, which was purified on an aluminum oxide column with hexane-dichloromethane-ethyl acetate as eluant to yield 1.44 g of pure 2-isopropyl-3-(2-chloroacetyl)pyrazolo[1,5-a]pyridine (yield 48.6%).

(e) 2-isopropyl-3-(2-hexamethylenetetramine-acetyl)pyrazolo[1,5-a]pyridine hydrochloride. To a solution of 626 mg (2.64 mmol) of 2-isopropyl-3-(2-chloroacetyl)pyrazolo[1,5-a]pyridine in 2 ml of chloroform was added 369 mg (2.1 mmol) of hexamethylenetetramine in 1 ml chloroform at room temperature with stirring, and then heated to 60° C. for 1 hour. After cooling, the solid was filtered and washed with ethyl ether to yield 620 mg (78.4%) of 2-isopropyl-3-(2-hexamethylenetetramine-acetyl)pyrazolo[1,5-a]pyridine hydrochloride.

(f) 2-amino-1-(2-isopropylpyrazolo[1,5-a]pyridin-3-yl)ethanone. To 4.56 ml of ethanolic HCl solution (ethanol:conc.HCl:water 20:4.8:4) was added 996 mg (2.64 mmol) of 2-isopropyl-3-(2-hexamethylenetetramine-acetyl)pyrazolo[1,5-a]pyridine hydrochloride. The mixture was stirred at 40° C. for 90 minutes. After the solvent was evaporated, the residue was washed with ethyl ether. The remaining solid was dissolved in water and purified on an open $C_{18}$ column with 0.05% HCl-acetonitrile as eluant to furnish 510 mg (79.3%.) of 2-amino-1-(2-isopropylpyrazolo[1,5-a]pyridin-3-yl)ethanone. Compound 1009.

Example 2

Synthesis of 2-amino-1-(2-isopropylpyrazolo[1,5-a]pyridin-3-yl)propan-1-one

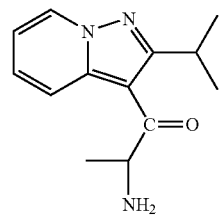

(a) 2-chloro-1-(2-isopropylpyrazolo[1,5-a]pyridine-3-yl)ethanone. 2.0 ml of 2-isopropylpyrazolo[1,5-a]pyridine, 2.0 ml of 2-chloropropionyl chloride and 200 mg of anhydrous $AlCl_3$ were mixed with stirring at room temperature for 4 days. After cooling, 50 ml of ethyl acetate was added, followed by pre-cooled 4N KOH solution to pH 8-8.5 at 0-5° C. The mixture was extracted with ethyl acetate twice. The organic phase was washed with brine and dried over $MgSO_4$. The solvent was evaporated under reduced pressure to obtain 2.6 g of crude compound, which was purified on an aluminum oxide column with hexane-dichloromethane-ethyl acetate as eluant to yield 1.16 g (37.2%.) of 2-chloro-1-(2-isopropylpyrazolo[1,5-a]pyridine-3-yl)ethanone.

(b) 2-amino-1-(2-isopropylpyrazolo[1,5-a]pyridin-3-yl)propan-1-one. $NH_3$ (gas) was bubbled through a solution of 1.16 g (4.6 mmol) of 2-isopropyl-3-(2-chloropropyl)pyrazolo[1,5-a]pyridine in 100 ml of 7N $NH_3$-MeOH solution at 40° C. for 50-60 hours in an apparatus fitted with a dry-ice condenser. After evaporation of solvent in vacuo, the residue was dissolved in 15 ml ethyl ether and precipitated by the addition of 4N HCl-dioxane solution. The precipitate was filtered and washed with ethyl ether. The residue was dissolved in water and purified on an open $C_{18}$ column with 0.05% HCl-acetonitrile as eluant to obtain 600 mg (49.2%) of 2-amino-1-(2-isopropylpyrazolo[1,5-a]pyridin-3-yl)propan-1-one. Compound 1013.

Example 3

Synthesis of 1-(2-isopropylpyrazolo[1,5-a]pyridin-3-yl)-2-methylpropan-1-one oxime

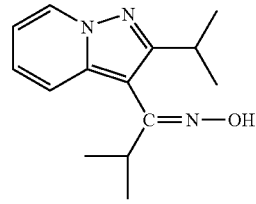

To a solution of 2.3 g (10 mmol) of 1-(2-isopropylpyrazolo[1,5-a]pyridin-3-yl)-2-methylpropan-1-one in 32 ml of anhydrous EtOH was added hydroxylamine hydrochloride 1.5 g (20 mmol), followed by dropwise addition of 2.4 g NaOH in 6 ml of water. The mixture was stirred and refluxed over night. After cooling, the solution was poured into a solution of 8.3 ml of 6N HCl and 380 ml ice water with stirring for 30 minutes. The precipitate was filtered and washed with ethyl ether-hexane to furnish 1.2 g (74.5%) of 1-(2-isopropylpyrazolo[1,5-a]pyridin-3-yl)-2-methylpropan-1-one oxime (as a mixture of cis- and trans-isomers), which was separated on an aluminum oxide column with hexane-dichloromethane-ethyl acetate as eluant to yield 0.3 g (cis-) and 0.325 g (trans-) isomers of 1-(2-isopropylpyrazolo[1,5-a]pyridin-3-yl)-2-methylpropan-1-one oxime. Compound 1012.

Example 4

Synthesis of 1-(2-isopropylpyrazolo[1,5-a]pyridin-3-yl)-2-methylpropan-1-one O-carbamoyl oxime

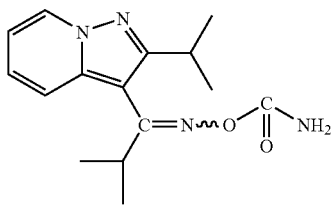

To a solution of 376 mg (1.53 mol) of 1-(2-isopropylpyrazolo[1,5-a]pyridin-3-yl)-2-methylpropan-1-one oxime in 2 ml of anhydrous THF was added 540 µl of trimethylsilyl isocyanate (85%) dropwise at 0° C. over 30 minutes. The reaction was stirred at room temperature overnight. Solvent was removed in vacuo, and the residue obtained was purified on an aluminum oxide column with hexane-dichloromethane-ethyl acetate as eluant to yield 200 mg (45.3%.) of 1-(2-isopropylpyrazolo[1,5-a]pyridin-3-yl)-2-methylpropan-1-one O-carbamoyl oxime. Compound 1014.

Example 5

2-methyl-1-(2-phenylpyrazolo[1,5-a]pyridin-3-yl)propan-1-one

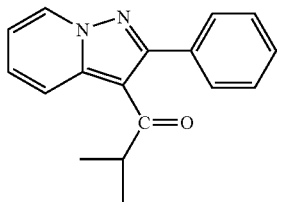

a) 4-methyl-1-phenylpent-1-yn-3-one. To a solution of 10.6 g (100 mmol) of ethynylbenzene in 50 ml of anhydrous THF was added dropwise 36 ml of n-butyl lithium (2.87M in hexane) at −50° C. under argon with stirring over a 10-15 minutes period, followed by the addition of 13.6 g of anhydrous zinc chloride in 50 ml of THF dropwise at −20° C. to 0° C. The reaction was stirred at 0° C. for 20 minutes, and 10.5 ml of isobutyryl chloride was added dropwise. After stirring at room temperature for 2 hours, the mixture was quenched with 60 ml of saturated ammonium chloride solution, followed by 10 ml of concentrated ammonium hydroxide and 100 ml of ethyl ether at 0-5° C. and extracted 3 times with ethyl acetate. The combined organic phases were washed with saturated ammonium chloride solution again, dried over MgSO$_4$ and evaporated under vacuum to obtain 19.4 g of 4-methyl-1-phenylpent-1-yn-3-one as a crude oil.

(b) 2-methyl-1-(2-phenylpyrazolo[1,5-a]pyridin-3-yl)propan-1-one. 5 g (20 mmol) of 4-methyl-1-phenylpent-1-yn-3-one and 4.45 g of 1-aminopyridinium iodide were dissolved in 30 ml of dry acetonitrile. To this solution was added dropwise 6.0 g of DBU in 10 ml of acetonitrile at 0° C. under argon during 30 minutes. This mixture was allowed to stir at room temperature overnight. The solvent was evaporated under reduced pressure and ethyl acetate was added to the residue. An insoluble solid was removed by filtration. The resulting ethyl acetate solution was washed with 10% citric acid, saturated ammonium chloride solution and dried over MgSO$_4$. The ethyl acetate was evaporated to furnish 5.2 g of crude product, which was purified on an aluminum oxide column with hexane-dichloromethane-ethyl acetate as eluant to yield 2.18 g (41.1%) of 2-methyl-1-(2-phenylpyrazolo[1,5-a]pyridin-3-yl)propan-1-one. Compound 1015.

Example 6

Synthesis of 2-methyl-1-(2-phenylpyrazolo[1,5-a]pyridin-3-yl)propan-1-one oxime

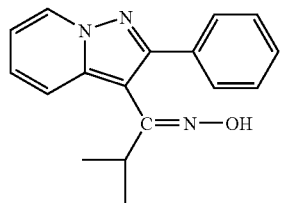

To a solution of 5.32 g (20 mmol) of 2-methyl-1-(2-phenylpyrazolo[1,5-a]pyridin-3-yl)propan-1-one in 32 ml of anhydrous EtOH was added 3 g of hydroxylamine hydrochloride, followed by dropwise addition of a solution of 4.0 g NaOH in 12 ml water. The mixture was stirred and refluxed over night. After cooling, the solution was poured into a solution of 11 ml of 6N HCl and 200 ml ice water with stirring for 30 minutes. The mixture was extracted with ethyl acetate three times. The organic phase was washed with brine and dried over MgSO$_4$. The solvent was removed under reduced pressure to obtain 4.6 g of crude compound, which was purified on an aluminum oxide column with hexane-dichloromethane-ethyl acetate as eluant to furnish 1.58 g (30.1%) of 2-methyl-1-(2-phenylpyrazolo[1,5-a]pyridin-3-yl)propan-1-one oxime. Compound 1016.

Example 7

Synthesis of 2-methyl-1-(2-phenylpyrazolo[1,5-a]pyridin-3-yl)propan-1-one O-carbamoyl oxime

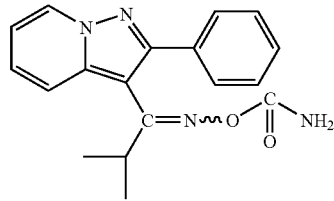

To a solution of 630 mg (2.24 mmol) of 2-methyl-1-(2-phenylpyrazolo[1,5-a]pyridin-3-yl)propan-1-one oxime in 2 ml of anhydrous THF was added 600 μl of trimethylsilyl isocyanate (85%) dropwise at 0° C. over 30 minutes. The mixture was stirred at room temperature overnight, followed by the addition of 500 μl pyridine and stirring for another 4 hours. The solvent was removed in vacuo, and the residue obtained was purified on an aluminum oxide column with hexane-dichloromethane-ethyl acetate as eluant to yield 482 mg (66.3%) of 2-methyl-1-(2-phenylpyrazolo[1,5-a]pyridin-3-yl)propan-1-one O-carbamoyl oxime. Compound 1017.

Example 8

Synthesis of 1-(2-(4-fluorophenyl)pyrazolo[1,5-a]pyridin-3-yl)-2-methylpropan-1-one

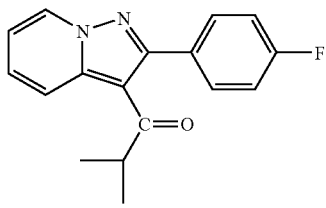

Starting with 5.0 g (41.25 mmol) of 4-fluoroethynylbenzene and 4.33 ml of isobutyryl chloride and 5.62 g $ZnCl_2$, the corresponding 1-(4-fluorophenyl)-4-methylpent-1-yn-3-one was prepared using the same procedure as in Example 5(a) to obtain 8.3 g of crude oil intermediate. From 4 g (20 mmol) of 1-(4-fluorophenyl)-4-methylpent-1-yn-3-one, 4.45 g of 1-aminopyridinium iodide and 6.0 g DBU was obtained 2.18 g (44.8%) of 1-(2-(4-fluorophenyl)pyrazolo[1,5-a]pyridin-3-yl)-2-methylpropan-1-one using the same procedure as in Example 5(b). Compound 1018.

Example 9

Synthesis of 1-(2-(4-fluorophenyl)pyrazolo[1,5-a]pyridin-3-yl)-2-methylpropan-1-one oxime

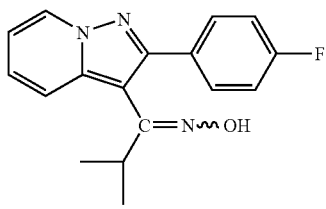

To a solution of 2.3 g (8.15 mmol) of 1-(2-(4-fluorophenyl)pyrazolo[1,5-a]pyridin-3-yl)-2-methylpropan-1-one in 32 ml of anhydrous EtOH was added 2.26 g of hydroxylamine hydrochloride, followed by a solution of 1.63 g (8.15 mmol) NaOH in 5 ml water dropwise. The mixture was stirred and refluxed over night. After cooling, the solution was poured into a solution of 4.8 ml 6N HCl in 100 ml ice water with stirring for 30 minutes. The mixture was extracted with ethyl acetate three times. The combined organic phases were washed with brine and dried over $MgSO_4$. After solvent evaporation under vacuum, 4.6 g of crude product was obtained. Purification on an aluminum oxide column with hexane-dichloromethane-ethyl acetate as eluant afforded 1.65 g (67%) of 1-(2-(4-fluorophenyl)pyrazolo[1,5-a]pyridin-3-yl)-2-methylpropan-1-one oxime. Compound 1019.

Example 10

Synthesis of 1-(2-(4-fluorophenyl)pyrazolo[1,5-a]pyridin-3-yl)-2-methylpropan-1-one O-carbamoyl oxime

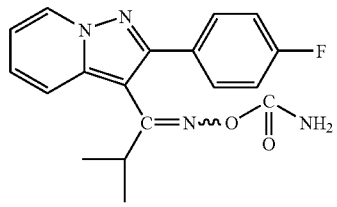

To a solution of 742 mg (2.5 mmol) of 1-(2-(4-fluorophenyl)pyrazolo[1,5-a]pyridin-3-yl)-2-methylpropan-1-one oxime in 5 ml of anhydrous THF was added 2 ml of trimethylsilyl isocyanate (85%) dropwise at 0° C. over 30 minutes. The mixture was stirred at room temperature over 48 hours, followed by addition of 50 μl pyridine. After stirring for another 4 hours, the solvent was removed and the residue was purified on an aluminum oxide column with hexane-dichloromethane-ethyl acetate as eluant to yield 482 mg (56.7%) of 1-(2-(4-fluorophenyl)pyrazolo[1,5-a]pyridin-3-yl)-2-methylpropan-1-one O-carbamoyl oxime. Compound 1020.

Example 11

Synthesis of 1-(2-(4-methoxyphenyl)pyrazolo[1,5-a]pyridin-3-yl)-2-methylpropan-1-one

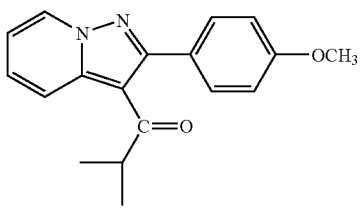

Starting with 5.0 g (36.7 mmol) of 4-methoxyethynylbenzene, 3.85 ml of isobutyryl chloride, and 5.0 g $ZnCl_2$, the corresponding 1-(4-methoxyphenyl)-4-methylpent-1-yn-3-one was prepared using the same procedure as in Example 5(a) to obtain 7.87 g of crude oil intermediate. Starting with 7.5 g (37 mmol) of 1-(4-methoxyphenyl)-4-methylpent-1-yn-3-one, 8.22 g (37 mmol) of 1-aminopyridinium iodide and 11.6 g DBU, 4.84 g (45%) of 1-(2-(4-methoxyphenyl)pyrazolo[1,5-a]pyridin-3-yl)-2-methylpropan-1-one was obtained as in Example 5(b). Compound 1021.

Example 12

Synthesis of 1-(2-(4-methoxyphenyl)pyrazolo[1,5-a]pyridin-3-yl)-2-methylpropan-1-one oxime

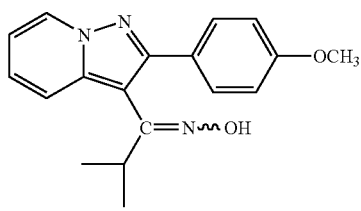

To a solution of 4.4 (14.9 mmol) of 1-(2-(4-methoxyphenyl)pyrazolo[1,5-a]pyridin-3-yl)-2-methylpropan-1-one in 32 ml of anhydrous EtOH was added 4.15 g of hydroxylamine hydrochloride, followed by a solution of 13.73 g (14.9 mmol) of NaOH in 10 ml water dropwise. The mixture was stirred and refluxed over night. After cooling, the solution was poured into a solution of 6 ml 6N HCl and 100 ml ice water with stirring for 30 minutes. The mixture was extracted with ethyl acetate three times. The organic phase was washed with brine and dried over $MgSO_4$. After evaporation of the solvent under vacuum, 5 g of crude product was obtained. Purification on an aluminum oxide column with hexane-dichloromethane-ethyl acetate as eluant afforded 2.33 g (50.5%) of 1-(2-(4-methoxyphenyl)pyrazolo[1,5-a]pyridin-3-yl)-2-methylpropan-1-one oxime. Compound 1022.

Example 13

Synthesis of 1-(2-(4-methoxyphenyl)pyrazolo[1,5-a]pyridin-3-yl)-2-methylpropan-1-one O-carbamoyl oxime

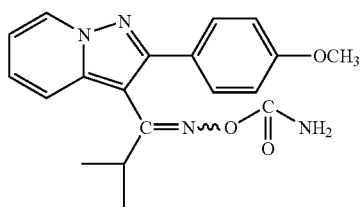

To a solution of 775 mg (2.5 mmol) of 1-(2-(4-methoxyphenyl)pyrazolo[1,5-a]pyridin-3-yl)-2-methylpropan-1-one oxime in 5 ml of anhydrous THF was added 2 ml of trimethylsilyl isocyanate (85%) dropwise at 0° C. over 30 minutes. The mixture was stirred at room temperature over 48 hours, followed by addition of 500 µl pyridine. After stirring for another 4 hours the solvent was removed, and the residue was extracted with ethyl acetate three times. The combined organic layers were washed with 10% citric acid twice and dried over $MgSO_4$. After evaporation of the solvent, 900 mg of crude product was obtained, which was purified on an aluminum oxide column with hexane-dichloromethane-ethyl acetate as eluant to yield 263 mg (29.8%) of 1-(2-(4-methoxyphenyl)pyrazolo[1,5-a]pyridin-3-yl)-2-methylpropan-1-one O-carbamoyl oxime. Compound 1023.

Example 14

Synthesis of 1-(2-(4-chlorophenyl)pyrazolo[1,5-a]pyridin-3-yl)-2-methylpropan-1-one

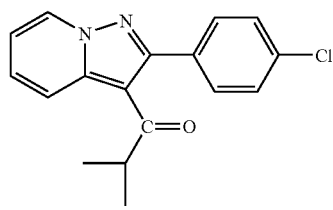

Starting with 4.9 g (35.8 mmol) of 4-chloroethynylbenzene, 3.76 ml of isobutyryl chloride and 4.88 g $ZnCl_2$, the corresponding 1-(4-chlorophenyl)-4-methylpent-1-yn-3-one was prepared using the same procedure as in Example 5(a) to obtain 9.21 g of crude oil intermediate. Starting with 9.21 g (35.8 mmol) of 1-(4-chlorophenyl)-4-methylpent-1-yn-3-one, 9.90 g (44 mmol) of 1-aminopyridinium iodide and 11 g DBU, the desired product was obtained—4.64 g (43%) of 1-(2-(4-chlorophenyl)pyrazolo[1,5-a]pyridin-3-yl)-2-methylpropan-1-one as in Example 5(b). Compound 1024.

Example 15

Synthesis of 1-(2-(4-chlorophenyl)pyrazolo[1,5-a]pyridin-3-yl)-2-methylpropan-1-one oxime

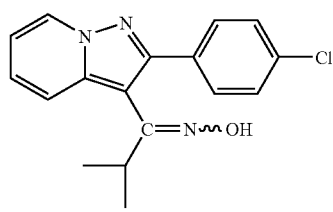

To a solution of 3.5 g (11.7 mmol) of 1-(2-(4-chlorophenyl)pyrazolo[1,5-a]pyridin-3-yl)-2-methylpropan-1-one in 65 ml of anhydrous EtOH was added 3.25 g of hydroxylamine hydrochloride, followed by a solution of 2.92 g (11.7 mmol) NaOH in 8 ml water dropwise. The mixture was stirred and refluxed over night. After cooling, the solution was evaporated and poured into a solution of 6 ml 6N HCl and 100 ml ice water with stirring for 30 minutes. The mixture was extracted with ethyl acetate three times. The organic phase was washed with brine and dried over $MgSO_4$. After evaporation of the solvent under vacuum, 5.11 g of crude product was obtained. Purification on an aluminum oxide column with hexane-dichloromethane-ethyl acetate as eluant furnished 1.86 g (50.7%) of 1-(2-(4-chlorophenyl)pyrazolo[1,5-a]pyridin-3-yl)-2-methylpropan-1-one oxime. Compound 1025.

Example 16

Synthesis of 1-(2-(4-chlorophenyl)pyrazolo[1,5-a]pyridin-3-yl)-2-methylpropan-1-one O-carbamoyl oxime

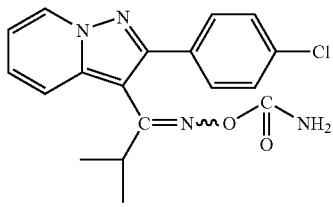

To a solution of 783 mg (2.5 mmol) of 1-(2-(4-chlorophenyl)pyrazolo[1,5-a]pyridin-3-yl)-2-methylpropan-1-one oxime in 5 ml of anhydrous THF was added 2 ml of trimethylsilyl isocyanate (85%) dropwise at 0° C. over 30 minutes. The mixture was stirred at room temperature over 48 hrs, followed by addition of 500 μl pyridine. After stirring for another 4 hours, the solvent was removed and the residue was extracted by ethyl acetate three times. The combined organic layers were washed with 1N HCl twice, brine and dried over MgSO$_4$. After evaporation of the solvent under vacuum, 935 mg of crude product was obtained. Purification on an aluminum oxide column with hexane-dichloromethane-ethyl acetate as eluant furnished 621 mg (69.6%) of 1-(2-(4-chlorophenyl)pyrazolo[1,5-a]pyridin-3-yl)-2-methylpropan-1-one O-carbamoyl oxime. Compound 1026.

Example 17

Synthesis of (4-chlorophenyl)(2-isopropylpyrazolo[1,5-a]pyridin-3-yl)methanone

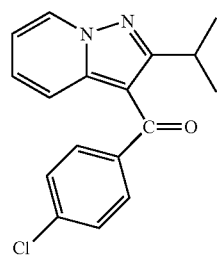

1.59 g of 2-isopropylpyrazolo[1,5-a]pyridine, 1.74 g of 4-chlorobenzoyl chloride and 200 mg anhydrous AlCl$_3$ were mixed with stirring at room temperature over night, then at 100-120° C. for 4 hrs. After cooling, the mixture was treated with 50 ml 20% dichloromethane in ethyl acetate and 15 ml of 10% Na$_2$CO$_3$, followed by addition of 4N KOH to pH 8-8.5 at 0-5° C. The mixture was extracted with ethyl acetate twice. The combined organic phases were washed with brine and dried over MgSO$_4$. The ethyl acetate was evaporated under reduced pressure to obtain 2.6 g of residue, which was purified on an aluminum oxide column with hexane-dichloromethane as eluant to yield 480 mg (16.3%) of (4-chlorophenyl)(2-isopropylpyrazolo[1,5-a]pyridin-3-yl)methanone. Compound 1007.

Example 18

Synthesis of (2-isopropylpyrazolo[1,5-a]pyridin-3-yl)(4-methoxyphenyl)methanone

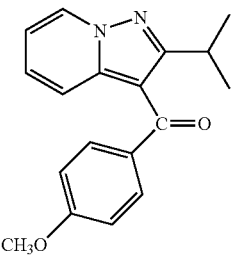

3.2 ml of 2-isopropylpyrazolo[1,5-a]pyridine, 2.2 g of 4-methoxybenzoyl chloride and 200 mg anhydrous AlCl$_3$ were mixed with stirring at room temperature for 4 days. After cooling, 50 ml of ethyl ether was added to the mixture, followed by addition of 4N KOH solution to pH 8-8.5 at 0-5° C. The mixture was extracted with ethyl acetate twice. The combined organic phases were washed with brine and dried over MgSO$_4$. The ethyl acetate was evaporated under reduced pressure to obtain 6.4 g of crude product, which was purified on an aluminum oxide column with hexane-dichloromethane-ethyl acetate as eluant to yield 510 mg (13.6%) of (2-isopropylpyrazolo[1,5-a]pyridin-3-yl)(4-methoxyphenyl)methanone. Compound 1008.

Example 19

Synthesis of 1-(2-(4-fluorophenyl)-6-(trifluoromethyl)pyrazolo[1,5-a]pyridin-3-yl)-2-methylpropan-1-one

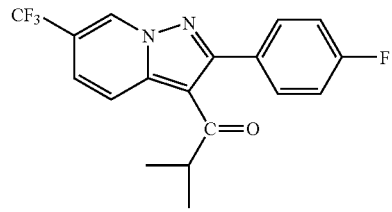

(a) 1-(4-fluorophenyl)-2-(5-(trifluoromethyl)pyridin-2-yl)ethanone. To a solution of 4-fluoroacetophenone (13.8 g, 100 mmol) and 2-chloro-5-trifluoromethylpyridine (20.0 g, 110 mmol) in 400 ml of anhydrous THF was added NaH (5.56 g, 220 mmol) (washed with pentane prior to use) in several portions. The reaction was stirred under argon at room temperature for 3 days. The reaction was carefully quenched with H$_2$O (300 ml), followed by addition of diethyl ether (200 ml). The organic layer was separated and extracted with 6N HCl (2×300 ml). The aqueous extracts were cooled to 0° C. and 6N NaOH was added dropwise to adjust the pH of the solution to pH 11-12. The mixture was then extracted with diethyl ether (4×150 ml) and the combined organic layers were then dried over MgSO₄. Filtration and concentration furnished 22.4 g (79%) of the title compound as a tautomeric mixture.

(b) 1-(4-fluorophenyl)-2-(5-(trifluoromethyl)pyridin-2-yl)ethanone oxime. To a solution of 1-(4-fluorophenyl)-2-(5-(trifluoromethyl)pyridin-2-yl)ethanone (8.00 g, 28.2 mmol) in methanol (100 ml) at room temperature was added 15% NaOH (29 ml, 109 mmol). The resulting solution was stirred vigorously as solid hydroxylamine hydrochloride (9.8 g, 140 mmol) was added portionwise. The mixture was heated to reflux for 1 hour, treated with charcoal while hot, and then quickly filtered through Celite before being allowed to cool. The filtrate was concentrated to one-half of its original volume and then cooled to 0° C. for 1 hour. The resultant solids were collected by filtration, washed with water, and dried under vacuum at 50° C. overnight to provide 5.00 g (59%) of the title compound as a dark yellow solid.

The oxime, compound 1032, 1-(2-(4-fluorophenyl)-6-(trifluoromethyl)pyrazolo[1,5-a]pyridin-3-yl)-2-methylpropan-1-one oxime, was prepared in a fashion similar to that described in (b) above.

(c) 2-(3-(4-fluorophenyl)-2H-azirin-2-yl)-5-(trifluoromethyl)pyridine. To a solution of 1-(4-fluorophenyl)-2-(5-(trifluoromethyl)pyridin-2-yl)ethanone oxime (4.00 g, 13.4 mmol) in dichloromethane was added triethylamine (7.5 ml, 53.6 mmol, dist. from CaH₂). The solution was cooled to 0° C. under argon and trifluoroacetic anhydride (2.2 ml, 16.2 mmol) was added dropwise. The reaction was stirred for 30 minutes and then quenched with water (100 ml). The organic layer was separated, dried over MgSO₄, filtered and concentrated to afford an oil. Purification by flash chromatography (15% EtOAc-hexane) yielded 3.08 g (82%) of the title compound, which crystallized on standing.

(d) 2-(4-fluorophenyl)-6-(trifluoromethyl)pyrazolo[1,5-a]pyridine. 2.82 g (10.0 mmol) of 2-(3-(4-fluorophenyl)-2H-azirin-2-yl)-5-(trifluoromethyl)pyridine was dissolved in 1,2,4-trichlorobenzene (30 ml, >99%) and the mixture was heated to 200° C. for 10 hours. The reaction mixture was cooled to room temperature and loaded onto a silica column. The column was eluted with hexane to remove 1,2,4-trichlorobenzene, and then with 20% Et₂O-hexane to elute the product. Concentration provided 2.62 g (94%) of the title compound.

(e) 1-(2-(4-fluorophenyl)-6-(trifluoromethyl)pyrazolo[1,5-a]pyridin-3-yl)-2-methylprop-1-enyl isobutyrate. To 2.50 g (8.9 mmol) of 2-(4-fluorophenyl)-6-(trifluoromethyl)pyrazolo[1,5-a]pyridine in 43 ml of isobutyric anhydride was added conc. H₂SO₄ (5 drops). The mixture was stirred and heated at 142° C. overnight. The mixture was cooled to room temperature and poured into water (120 ml) at 0° C. The solution was then adjusted to pH 10 with 2N NaOH. The aqueous layer was extracted with Et₂O (3×100 ml), dried over MgSO₄, filtered and concentrated. The crude product was purified by flash column chromatography (3% EtOAc-hexane) to afford 2.54 g (68%) of the title compound as an orange solid. Compound 1033.

(f) 1-(2-(4-fluorophenyl)-6-(trifluoromethyl)pyrazolo[1,5-a]pyridin-3-yl)-2-methylpropan-1-one. To product of (e) (0.45 g, 1.07 mmol) was dissolved in THF (1 ml) and cooled to 0° C. A 1.1M solution of NaOMe in MeOH (1.3 ml, 1.4 mmol) was added dropwise and the mixture warmed to room temperature over 3 hours. Saturated NH₄Cl solution was added to adjust the solution to pH 6-7 and the mixture was extracted with Et₂O (4×5 ml). The combined organic layers were washed with water (3×2 ml), brine, dried over MgSO₄, filtered and concentrated to provide the crude product as a solid. Recrystallization from hexane provided 0.35 g (78%) of 1-(2-(4-fluorophenyl)-6-(trifluoromethyl)pyrazolo[1,5-a]pyridin-3-yl)-2-methylpropan-1-one; m.p. 129-130° C. Compound 1027.

Example 20

Synthesis of 1-(2-isopropylpyrazolo[1,5-a]pyridin-3-yl)propan-1-one

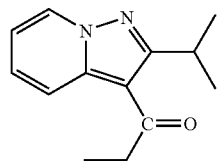

3.70 g (23 mmol) of 2-isopropylpyrazolo[1,5-a]pyridine was dissolved in 12.03 g (92.4 mmol) of propionic anhydride and 2 drops of conc. H₂SO₄ were added. The reaction mixture was heated to reflux until full consumption of starting material (determined by ¹H NMR, 7 hours). The brown solution was cooled to room temperature, and was poured on a mixture of ice (20 g) and K₂CO₃ (20 g). K₂CO₃ was added until the pH of the reaction mixture was 11 and then the reaction mixture was stirred at room temperature for an additional hour. The aqueous layer was extracted four times with ethyl acetate. The combined organic layers were washed with brine, treated with charcoal, dried over Na₂SO₄, and the solvent was evaporated under reduced pressure. Flash column chromatography (hexanes-ethyl acetate, 9:1; deactivated silica) of the residue afforded 760 mg (15.4%) of 1-(2-isopropylpyrazolo[1,5-a]pyridin-3-yl)propan-1-one as a yellow oil, which crystallized when stored in the refrigerator; m.p. 41-43° C. Compound 1001.

Example 21

Synthesis of 1-(2-isopropylpyrazolo[1,5-a]pyridin-3-yl)-2-methylpropan-1-ol

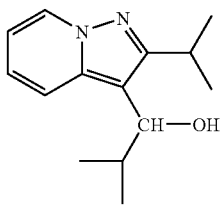

2.5 g (10.76 mmol) of 1-(2-isopropylpyrazolo[1,5-a]pyridin-3-yl)-2-methylpropan-1-one was dissolved in MeOH (50 ml) (charcoal filtration) and cooled to 0° C. NaBH₄ (570 mg, 15.06 mmol) was added portion wise. The reaction mixture was heated to reflux until complete conversion of starting material (2-4 hours). The reaction mixture was cooled to room temperature, and was quenched by the addition of water (50 ml). The aqueous layer was extracted four times with dichloromethane. The combined organic layers were washed with brine, treated with charcoal, dried over Na₂SO₄, and the solvent was evaporated under reduced pressure. Flash column chromatography (hexanes-ethyl acetate, 5:2; 10% deactivated silica) of the residue (yellow oil) afforded 1-(2-isopropylpyrazolo[1,5-a]pyridin-3-yl)-2-methylpropan-1-ol as a colorless oil (1.7 g, 68%), which crystallized upon trituration with pentane; m.p. 69° C. Compound 1002.

Example 22

Synthesis of 1-(2-isopropyl-4,5,6,7-tetrahydropyrazolo[1,5-a]pyridin-3-yl)-2-methylpropan-1-amine

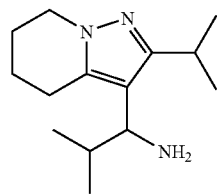

To a solution of 600 mg (4.6 mmol) of N-benzyl-1-(2-isopropylpyrazolo[1,5-a]pyridin-3-yl)-2-methylpropan-1-amine in 10 ml of acetic acid was added 100 mg of $PtO_2$ in hydrogenation bottle. $H_2$ was applied at 50 psi for 4 hours. The reaction was worked up by filtration and dilution with 0.1N HCl to provide 503 mg of crude product. Purification by $C_{18}$ preparative HPLC furnished 400 mg of purified 1-(2-isopropyl-4,5,6,7-tetrahydropyrazolo[1,5-a]pyridin-3-yl)-2-methylpropan-1-amine after lyophilization. Compound 1011.

The products from Examples 22-58 were each characterized by fast atom bombardment mass spectrometry (FAB MS) to provide the corresponding M+1 ions. Products were also characterized by $^1$H NMR, and when warranted, their structures further confirmed by $^{13}$C NMR and correlated (multinuclear $^1$H and $^{13}$C) NMR spectroscopy.

Example 23

Synthesis of 1-(2-isopropylpyrazolo[1,5-a]pyridin-3-yl)-2-morpholinopropan-1-one hydrochloride

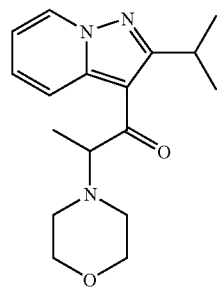

To a solution of 500 mg (2 mmol) 2-chloro-1-(2-isopropylpyrazolo[1,5-a]pyridin-3-yl)propan-1-one in 4 ml of MeOH was added 227 mg (2.6 mmol) of morpholine and 150 mg NaI. The mixture was stirred at RT for 3 days. The solvent was removed and the residue dissolved in 5 ml of ether, followed by titration with 4N HCl-dioxane to obtain a precipitate. Recrystallization from isopropanol/ether produced 200 mg of pure 1-(2-isopropylpyrazolo[1,5-a]pyridin-3-yl)-2-morpholinopropan-1-one hydrochloride. Compound 1034.

Example 24

Synthesis of 1-(2-isopropylpyrazolo[1,5-a]pyridin-3-yl)-2-(4-methylpiperazin-1-yl)propan-1-one hydrochloride

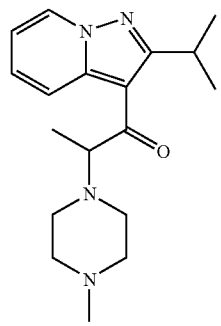

A mixture of 500 mg (2 mmol) of 2-chloro-1-(2-isopropylpyrazolo[1,5-a]pyridin-3-yl)propan-1-one, 272 μl (2.4 mmol) of N-methylpiperazine and 50 mg of NaI in 4 ml of MeOH was stirred at RT for 4 days. The solvent was removed and the crude residue was purified on an $Al_2O_3$ column. The fractions containing purified product were titrated with 4N HCl-dioxane to obtain a precipitate. Recrystallization from isopropanol/ether produced 150 mg of 1-(2-isopropylpyrazolo[1,5-a]pyridin-3-yl)-2-(4-methylpiperazin-1-yl)propan-1-one hydrochloride (shown in neutral form above). Compound 1035.

Example 25

Synthesis of 1-(2-isopropylpyrazolo[1,5-a]pyridin-3-yl)-2-(piperidin-1-yl)propan-1-one hydrochloride

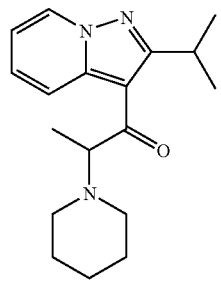

A mixture of 500 mg (2 mmol) of 2-chloro-1-(2-isopropylpyrazolo[1,5-a]pyridin-3-yl)propan-1-one, 478 ul (4.8 mmol) of piperidine and 50 mg of NaI in 4 ml of MeOH was stirred at 50° C. overnight. The residue obtained after evaporation of the solvent was purified on an $Al_2O_3$ column. The fractions containing purified product were titrated with 4N HCl-dioxane to obtain a precipitate. Recrystallization from isopropanol/ether produced 175 mg of 1-(2-isopropylpyrazolo[1,5-a]pyridin-3-yl)-2-(piperidin-1-yl)propan-1-one hydrochloride. Compound 1036.

Example 26

Synthesis of 1-(2-isopropylpyrazolo[1,5-a]pyridin-3-yl)-2-(piperazin-1-yl)propan-1-one hydrochloride

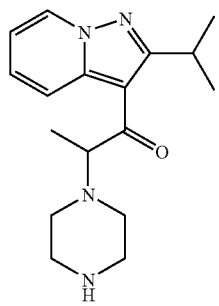

A mixture of 980 mg (3.90 mmol) of 2-chloro-1-(2-isopropylpyrazolo[1,5-a]pyridin-3-yl)propan-1-one, 1.45 g (4 mmol) of N-Boc-piperazine and 100 mg of NaI in 10 ml of MeOH was stirred at 50-70° C. for 5 hours. The residue obtained after evaporation of the solvent was purified on an Al$_2$O$_3$ column. The fractions containing purified product were titrated with 4N HCl-dioxane to obtain a precipitate. Recrystallization from isopropanol/ether produced 150 mg of 1-(2-isopropylpyrazolo[1,5-a]pyridin-3-yl)-2-(piperazin-1-yl)propan-1-one hydrochloride. Compound 1037.

Example 27

Synthesis of (3-chloropyridin-2-yl)(2-isopropylpyrazolo[1,5-a]pyridin-3-yl)methanone

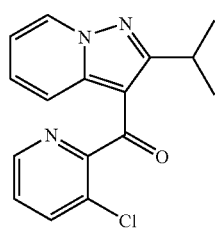

Picolinic acid was reacted with thionyl chloride to yield the corresponding acid chloride, which was used without purification to acylate 2-isopropylpyrazolo[1,5-a]pyridine in the presence of 300 mg of AlCl$_3$ at RT for 4 days. 5 g of crude product were obtained after workup, followed by purification on an Al$_2$O$_3$ column to produce 373 mg of (3-chloropyridin-2-yl)(2-isopropylpyrazolo[1,5-a]pyridin-3-yl)methanone. The structure was assigned by NMR and LC-MS. Compound 1038.

Example 28

Synthesis of 2-amino-1-(2-isopropylpyrazolo[1,5-a]pyridin-3-yl)-2-phenylethanone

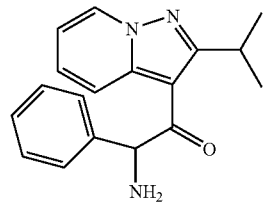

A mixture of 3.5 ml (21.8 mmol) of 2-isopropylpyrazolo[1,5-a]pyridine, 2 ml (10.5 mmol) of 2-chloro-phenylacetyl chloride and 300 mg of AlCl$_3$ were stirred at RT for 4 days. The resulting 1.5 g of crude chloride was dissolved in 150 ml of MeOH, and reacted with NH$_3$ (gas) in presence of 20 mg of NaI at 400° C. for 3 days to get 1.2 g of crude product, followed by purification on an Al$_2$O$_3$ column to obtain 220 mg of 2-amino-1-(2-isopropylpyrazolo[1,5-a]pyridin-3-yl)-2-phenylethanone. Compound 1039.

Example 29

Synthesis of 1-(2-ethylpyrazolo[1,5-a]pyridin-3-yl)propan-1-one

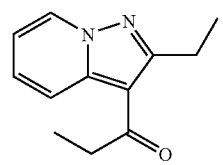

4.35 g (47 mmol) of propionyl chloride was dropwise added to 4.5 g (23.5 mmol) of 2-methyl-1-aminopyridium bromide in 50 ml of pyridine at 0° C. over 20 minutes. The mixture was stirred at RT for 1 hour and refluxed for another 2 hours. 3.39 g of crude product obtained after workup was purified on an Al$_2$O$_3$ column and 1.27 g of 1-(2-ethylpyrazolo[1,5-a]pyridin-3-yl)propan-1-one were obtained after recrystallization from ether/hexane. Compound 1040.

Example 30

Synthesis of 2-(benzyl(methyl)amino)-1-(2-isopropylpyrazolo[1,5-a]pyridin-3-yl)propan-1-one

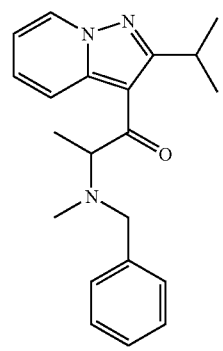

A mixture of 2.37 g (13.4 mmol) of 2-chloro-1-(2-isopropylpyrazolo[1,5-a]pyridin-3-yl)propan-1-one, 1.74 ml (13.4 mmol) of N-methyl benzylamine and 50 mg of NaI in 15 ml of MeOH was refluxed overnight. The mixture obtained after evaporation of the solvent was purified on an Al$_2$O$_3$ column, and recrystallized from ether/hexane to obtain 1.5 g of 2-(benzyl(methyl)amino)-1-(2-isopropylpyrazolo[1,5-a]pyridin-3-yl)propan-1-one. Compound 1041.

Example 31

Synthesis of 1-(2-isopropylpyrazolo[1,5-a]pyridin-3-yl)-2-(methylamino)propan-1-one hydrochloride

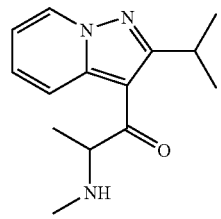

To 700 mg of 2-(benzyl(methyl)amino)-1-(2-isopropylpyrazolo[1,5-a]pyridin-3-yl)propan-1-one in 2.5 ml H$_2$O and 47.5 ml MeOH was added 30 mg of 10% Pd—C. The mixture was hydrogenated at 50 psi for 5 hours. The residue obtained after filtration and solvent evaporation was dissolved in ether and treated with HCl/ether to obtain 640 mg of 1-(2-isopropylpyrazolo[1,5-a]pyridin-3-yl)-2-(methylamino)propan-1-one hydrochloride. Compound 1042.

Example 32

Synthesis of N-(1-(2-isopropylpyrazolo[1,5-a]pyridin-3-yl)-2-methylpropyl)cyclopropanamine

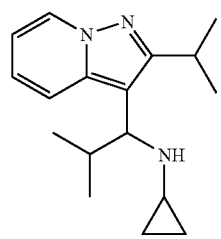

To a mixture of 2.3 g (10 mmol) of 1-(2-isopropylpyrazolo[1,5-a]pyridin-3-yl)-2-methylpropan-1-one and 4.8 ml (75 mmol) of cyclopropylamine in 25 ml of benzene were added dropwise 735 µl of TiCl$_4$ in 5 ml of benzene at RT over 20 minutes under a nitrogen atmosphere. The mixture was stirred at RT for 1 hour and refluxed for 2 hours. Filtration and evaporation of the solvent furnished an intermediate imine, which was dissolved in 10 ml of MeOH and reacted with 378 mg of NaBH$_4$ at RT overnight. 4.3 g of crude material was obtained after workup. Recrystallization from MeOH-acetone-ether yielded 770 mg of N-(1-(2-isopropylpyrazolo[1,5-a]pyridin-3-yl)-2-methylpropyl)cyclopropanamine. Compound 1044.

Example 33

Synthesis of N-(cyclopropylmethyl)-1-(2-isopropylpyrazolo[1,5-a]pyridin-3-yl)-2-methylpropan-1-amine hydrochloride

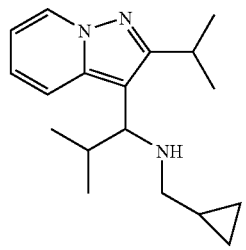

To a mixture of 2.3 g (10 mmol) of 1-(2-isopropylpyrazolo[1,5-a]pyridin-3-yl)-2-methylpropan-1-one and 2.37 g (30 mmol) of aminomethylcyclopropane in 25 ml of benzene were added 548 µl of TiCl$_4$ in 5 ml of benzene at RT over 20 minutes under a nitrogen atmosphere. The mixture was stirred at RT for 1 hour and refluxed for 2 hours. Filtration and evaporation of the solvent furnished an intermediate, which was purified by chromatography on an Al$_2$O$_3$ column. 1.69 g of purified intermediate imine was reduced by 338 mg of NaBH$_4$ in 10 ml of MeOH. The crude product was purified again on Al$_2$O$_3$ column to produce 1 g of an oil. Titration with 2N HCl-ether furnished 616 mg of N-(cyclopropylmethyl)-1-(2-isopropylpyrazolo[1,5-a]pyridin-3-yl)-2-methylpropan-1-amine hydrochloride. Compound 1048.

Example 34

Synthesis of 2-(cyclopropylamino)-1-(2-isopropylpyrazolo[1,5-a]pyridin-3-yl)propan-1-one hydrochloride

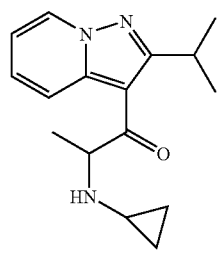

621 mg (2.4 mmol) of 2-chloro-1-(2-isopropylpyrazolo[1,5-a]pyridin-3-yl)propan-1-one was reacted with 283 mg (4.8 mmol) cyclopropylamine in the presence of 20 mg of NaI in 6 ml of MeOH. The crude product obtained after workup was acidified with 2N HCl-ether to furnish 405 mg of 2-(cyclopropylamino)-1-(2-isopropylpyrazolo[1,5-a]pyridin-3-yl)propan-1-one hydrochloride. Compound 1045.

Example 35

Synthesis of 1-(2-isopropylpyrazolo[1,5-a]pyridin-3-yl)-2-methylpropan-1-amine hydrochloride

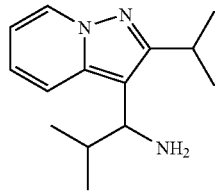

3.5 g (15 mmol) of 1-(2-isopropylpyrazolo[1,5-a]pyridin-3-yl)-2-methylpropan-1-one was stirred at RT with 11.48 ml (7×15 mmol) of benzylamine and 1,097 µl of TiCl$_4$ in 40 ml of benzene, then refluxed for 2 hours. Filtration and evaporation of the solvent furnished an intermediate, which was purified by chromatography on an Al$_2$O$_3$ column to furnish 3.1 g of intermediate imine. Reduction of the imine with 163 mg of NaBH$_4$ in MeOH furnished crude benzylamine, which was hydrogenated on 10% Pd—C. The crude product was purified by C18-reverse-phase preparative HPLC. Addition of dilute HCl to the fractions containing purified product followed by lyophilization furnished 399 mg of 1-(2-isopropylpyrazolo[1,5-a]pyridin-3-yl)-2-methylpropan-1-amine hydrochloride. Compound 1051.

Example 36

Synthesis of 2-amino-1-(2-(4-fluorophenyl)pyrazolo[1,5-a]pyridin-3-yl)propan-1-one hydrochloride

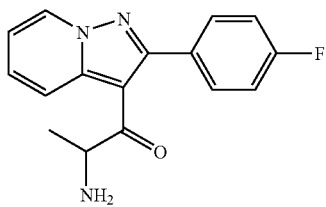

To a mixture of 1.1 g (3.4 mmol) of 2-(5-(4-fluorophenyl)-3-oxopent-4-yn-2-yl)isoindoline-1,3-dione and 785 mg (3.4 mmol) of N-aminopyridinium iodide in 10 ml of acetonitrile was added dropwise 1.04 g of DBU in 5 ml of acetonitrile at 0° C. for 20 minutes under a nitrogen atmosphere. The reaction was stirred at RT overnight, and it was worked up with ethyl acetate and ammonium chloride to produce 2-(1-(2-(4-fluorophenyl)pyrazolo[1,5-a]pyridin-3-yl)-1-oxopropan-2-yl)isoindoline-1,3-dione as a crude solid. The phthalimide intermediate was reacted with 500 µl of hydrazine hydrate at RT in ethanol overnight. After workup with ethyl acetate and ammonium chloride, 1 g of crude product was obtained. The crude product was purified by C18-reverse-phase preparative HPLC. Addition of dilute HCl to the fractions containing purified product followed by lyophilization furnished 110 mg of 2-amino-1-(2-(4-fluorophenyl)pyrazolo[1,5-a]pyridin-3-yl)propan-1-one hydrochloride. Compound 1052.

Example 37

Synthesis of cyclopropyl(2-isopropylpyrazolo[1,5-a]pyridin-3-yl)methanone

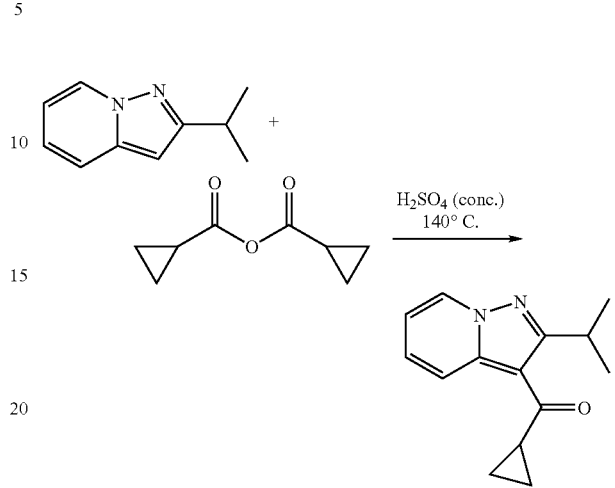

2-isopropyl-pyrazolo[1,5-a]pyridine (2.00 g, 12.4 mmol) was dissolved in cyclopropyl anhydride (8.00 g, 51.9 mmol). Concentrated H$_2$SO$_4$ (3 drops) was added at room temperature and the mixture was then heated to 140° C. for 28 hours. The mixture was then cooled to 0° C., diluted with H$_2$O (10 mL) and 50% NaOH (aq) was added to achieve a solution pH of 11. This mixture was extracted with Et$_2$O (3×10 mL). The combined organic layers were washed with H$_2$O (15 mL), brine (15 mL), dried (Na$_2$SO$_4$), filtered and concentrated. The crude mixture was then immediately subjected to flash chromatography (90% EtOAc/hexane) to afford 1.02 g (4.4 mmol, 36%) of the title compound as a white powder. This material was then recrystallized from n-heptane to afford 0.6115 g (2.7 mmol, 22%) of SB-I1-61 was white needles. mp 72° C. (n-heptane); IR (thin film) v=2969, 1635, 1506, 1439 $^1$H NMR (300 MHz, CDCl$_3$) δ=8.42 (d, J=6.8 Hz, 1H), 8.09 (d, J=9.0 Hz, 1H), 7.33-7.27 (m, 1H), 6.82 (ddd, J=6.8, 6.8, 1.2 Hz, 1H), 3.75 (sept, J=6.9 Hz, 1H), 2.47-2.39 (m, 1H), 1.40 (d, J=6.9 Hz, 6H), 1.27-1.17 (m, 2H), 0.99-0.93 (m, 2H); $^{13}$C NMR (150 MHz, CDCl$_3$) δ=194.8, 163.1, 141.6, 128.9, 127.4, 118.9, 113.2, 110.7, 27.8, 22.4, 20.4, 10.2; MS (EI) m/z 229 (M+1, 18.2), 228 (M$^+$, 100.0), 213 (46.4), 200 (13.1), 199 (23.4), 198 (14.1), 185 (23.2), 171 (23.2), 160 (13.5), 145 (11.8), 132 (10.2), 131 (13.8), 119 (11.6), 117 (18.0), 92 (10.2), 91 (10.9), 90 11.0), 84 (11.2), 78 (17.6), 69 (24.6) 51 (10.9); HRMS (EI) calcd for C$_{14}$H$_{16}$N$_2$O: 228.1263. found: 228.1261; Anal. Calcd for C$_{14}$H$_{16}$N$_2$O: C, 73.66%; H, 7.06%. Found: C, 73.93%; H, 7.25%. Compound 1046.

Example 38

Synthesis of cyclopropyl(2-cyclopropylpyrazolo[1,5-a]pyridin-3-yl)methanone

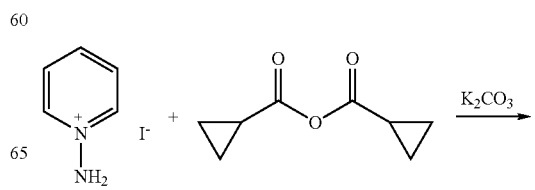

-continued

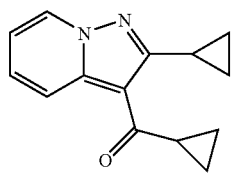

1-Aminopyridinium iodide (5.2 g, 0.024 mol) was suspended in cyclopropyl anhydride (22.0 g, 0.143 mol) and $K_2CO_3$ (3.4 g, 0.025 mol) was added. The reaction mixture was slowly heated to 190° C. and kept at the same temperature for 8 hours and then stirred at rt for 12 hours. The suspension was diluted with $H_2O$ (50 ml) and basified with 50% NaOH at 50° C. The aqueous layer was cooled to rt and extracted four times with EtOAc. The combined organic layers were washed with brine, treated with charcoal, dried over anhydrous $MgSO_4$ and filtered. The solvent was evaporated and the residue was purified by flash column chromatography (EtOAc:hexanes, 10:1 to 5:1) to give the title compound as colorless solid (2.4 g, 44%) after recrystallization from n-heptane.

mp 102-104° C. (n-heptane); IR (thin film) v=3091, 3007, 1638, 1509, 1438, 1393, 1325, 1262, 1206, 1182 cm$^{-1}$; $^1$H NMR (300 MHz, CDCl$_3$) δ=8.39 (d, J=6.9 Hz, 1H), 8.23 (d, J=8.9 Hz, 1H), 7.33-7.41 (m, 1H), 6.90 (dt, J=6.9, 1.2 Hz, 1H), 2.75-2.87 (m, 1H), 2.51-2.63 (m, 1H), 1.26-1.34 (m, 2H), 1.16-1.23 (m, 2H) 1.07-1.15 (m, 2H) 0.97-1.06 (m, 2H); $^{13}$C NMR (75 MHz, CDCl$_3$) δ=195.2, 158.6, 142.0, 128.5, 127.6, 119.2, 113.6, 112.4, 20.2, 10.2, 9.9, 8.6; MS (EI) m/z (%): 226 (54), 225 (11), 211 (33), 199 (14), 198 (26), 185 (59), 183 (12), 170 (26), 169 (43), 157 (27), 156 (14), 155 (20), 142 (13), 130 (16), 117 (18), 90 (12), 78 (27), 51 (13), 41 (33); HRMS (EI) calcd for $C_{14}H_{14}N_2O$: 226.1106. found: 226.1107; Anal. Calcd for $C_{14}H_{14}N_2O$: C, 74.31%; H, 6.24%. Found: C, 74.27%; H, 6.28%. Compound 1047.

Example 39

Synthesis of 1-(2-methoxypyrazolo[1,5-a]pyridin-3-yl)-2-methylpropan-1-one

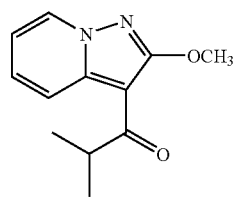

A mixture of 700 mg (4.7 mmol) of 2-methoxypyrazolo[1,5-a]pyridine, 550 mg of isobutyryl chloride and 300 mg of AlCl$_3$ was stirred in 2 ml of DCE at RT for 5 hours. The reaction was quenched with saturated NH$_4$Cl and extracted with ethyl acetate to yield 1 g of crude product. Purification on an Al$_2$O$_3$ column furnished 323 mg of 1-(2-methoxypyrazolo[1,5-a]pyridin-3-yl)-2-methylpropan-1-one. Compound 1055.

Example 40

Synthesis of 2-amino-1-(2-methoxypyrazolo[1,5-a]pyridin-3-yl)propan-1-one

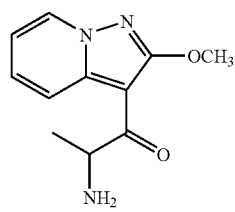

A mixture of 500 mg (3.3 mmol) of 2-methoxypyrazolo[1,5-a]pyridine, 393 µl of 2-chloro-propionyl chloride and 300 mg of AlCl$_3$ was stirred in 2 ml of DCE at RT for 5 hours. The reaction was quenched with saturated NH$_4$Cl and extracted with ethyl acetate to yield 663 mg of crude α-chloroketone. Crude α-chloroketone was reacted without further purification with 1.03 g of NaN$_3$ in 5 ml of DMF overnight to provide 1 g of crude α-azidoketone. Reduction of α-azidoketone was carried out with 1.17 g of Ph$_3$P in 10 ml of THF containing 60 µl of H$_2$O. The product was purified on an Al$_2$O$_3$ column to yield 116 mg of 2-amino-1-(2-methoxypyrazolo[1,5-a]pyridin-3-yl)propan-1-one. Compound 1057.

Example 41

Synthesis of 2-amino-1-(2-isopropylpyrazolo[1,5-a]pyridin-3-yl)butan-1-one

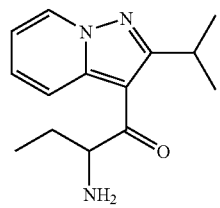

Following the same procedure for the synthesis of compound 1057, 250 mg of 2-amino-1-(2-isopropylpyrazolo[1,5-a]pyridin-3-yl)butan-1-one was obtained from 4 g (25 mmol) of 2-isopropylpyrazolo[1,5-a]pyridine, 3.5 g of 2-chloro-butyryl chloride and 600 mg of AlCl$_3$. Compound 1060.

Example 42

Synthesis of 2-amino-1-(2-isopropylpyrazolo[1,5-a]pyridin-3-yl)-4-methylpentan-1-one

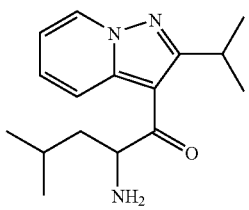

Following the same procedure for the synthesis of compound 1057, 259 mg of 2-amino-1-(2-isopropylpyrazolo[1,5-a]pyridin-3-yl)-4-methylpentan-1-one was obtained from 3.2 g (20 mmol) of 2-isopropylpyrazolo[1,5-a]pyridine, 3.37 g (20 mmol) of 2-chloro-valeryl chloride and 600 mg of AlCl$_3$. Compound 1061.

Example 43

Synthesis of 1-(2-(4-fluorophenyl)pyrazolo[1,5-a]pyridin-3-yl)propan-1-one

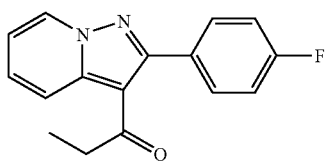

To a mixture of 8.7 g (38 mmol) of 4-chloro-1-(4-fluorophenyl)pent-1-yn-3-one and 10 g (45 mmol) of N-aminopyridinium iodide in 140 ml of acetonitrile was added dropwise 11 g of DBU in 50 ml of acetonitrile at 0° C. for 20 minutes under a nitrogen atmosphere. The reaction was then stirred at RT overnight. After evaporation of the solvent, the crude mixture was purified on an Al$_2$O$_3$ column, and the desired product recrystallized from ethyl acetate-hexane to obtain 200 mg of 1-(2-(4-fluorophenyl)pyrazolo[1,5-a]pyridin-3-yl)propan-1-one. Compound 1070.

Example 44

Synthesis of 1-(2-(dimethylamino)pyrazolo[1,5-a]pyridin-3-yl)-2-methylpropan-1-one

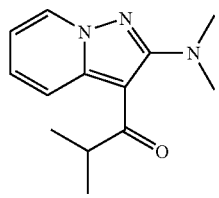

A mixture of 560 mg (3.45 mmol) of N,N-dimethylpyrazolo[1,5-a]pyridin-2-amine, 355 µl (3.45 mmol) of isobutyryl chloride and 100 mg of AlCl$_3$ was stirred in 3 ml of DCE at RT overnight. The mixture was quenched with saturated NH$_4$Cl and extracted with EtOAc, and the crude product was purified on an Al$_2$O$_3$ column to provide 208 mg of 1-(2-(dimethylamino)pyrazolo[1,5-a]pyridin-3-yl)-2-methylpropan-1-one. Compound 1072.

Example 45

Synthesis of 2-amino-1-(2-(dimethylamino)pyrazolo[1,5-a]pyridin-3-yl)propan-1-one

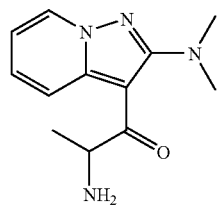

A mixture of 620 mg (3.85 mmol) of N,N-dimethylpyrazolo[1,5-a]pyridin-2-amine, 458.4 µl of 2-chloro-propionyl chloride and 100 mg of AlCl$_3$ was stirred in 6 ml of DCE at RT overnight. The mixture was quenched with saturated NH$_4$Cl and extracted with EtOAc to provide 756 mg of crude x-chloroketone intermediate. Reaction of x-chloroketone with 1.17 g of NaN$_3$ in 5 ml of DMF, followed by reduction with 1.17 g of Ph$_3$P in 10 ml of THF containing 7211 of H$_2$O resulted in 1.3 g of crude product. Purification on an Al$_2$O$_3$ column yielded 404 mg of 2-amino-1-(2-(dimethylamino)pyrazolo[1,5-a]pyridin-3-yl)propan-1-one. Compound 1075.

Example 46

Synthesis of 2-amino-1-(2-isopropylpyrazolo[1,5-a]pyridin-3-yl)hexan-1-one

A mixture of 4 g (25 mmol) of 2-isopropylpyrazolo[1,5-a]pyridine, 5.32 g (25 mmol) of 2-bromohexanoyl chloride and 600 mg of AlCl3 was stirred in 6 ml of DCE at RT for 3 days. The mixture was quenched with saturated NH4Cl and extracted with EtOAc to provide 4.85 g α-bromoketone intermediate. Reaction α-bromoketone with 5.1 g of NaN3 in 25 ml of DMF, followed by reduction with Ph3P in 50 ml of THF containing 594 µl of H$_2$O yielded 9 g of crude product. Purification of the crude product on a silica gel column furnished 200 mg of 2-amino-1-(2-isopropylpyrazolo[1,5-a]pyridin-3-yl)hexan-1-one and 1.5 g of recovered 2-isopropylpyrazolo[1,5-a]pyridine starting material. Compound 1077.

Example 47

Synthesis of 2-amino-1-(2-isopropylpyrazolo[1,5-a]pyridin-3-yl)-3-methoxypropan-1-one

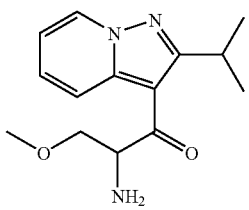

A mixture of 4 g (25 mmol) of 2-isopropylpyrazolo[1,5-a]pyridine, 3.9 g (25 mmol) of 2-chloro-3-methoxy-propionyl chloride and 600 mg of AlCl$_3$ in 6 ml of DCE was stirred at RT for 3 days. The mixture was quenched with saturated NH$_4$Cl and extracted with EtOAc to provide 6.3 g of crude α-chloroketone intermediate. Reaction of α-chloroketone with 5.1 g of NaN$_3$ in 25 ml of DMF, followed by reduction with 4.76 g of Ph$_3$P in 50 ml of THF containing 594 μl of H$_2$O furnished 9 g of crude product. Purification of the desired product was carried out on a silica gel column to furnish 560 mg of 2-amino-1-(2-isopropylpyrazolo[1,5-a]pyridin-3-yl)-3-methoxypropan-1-one along with 1.6 g of recovered 2-isopropylpyrazolo[1,5-a]pyridine starting material. Compound 1082.

Example 48

Synthesis of (Z)-2-(hydroxyimino)-1-(2-isopropylpyrazolo[1,5-a]pyridin-3-yl)propan-1-one

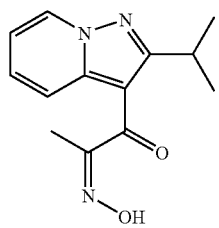

A mixture of 6.4 g (40 mmol) of 2-isopropylpyrazolo[1,5-a]pyridine, 3.7 g (40 mmol) of propionyl chloride and 400 mg of AlCl3 was stirred at RT in 5 ml of CS2 for 3 days. The mixture was quenched with saturated NH4Cl and extracted with EtOAc to provide 5.44 g of crude 1-(2-isopropylpyrazolo[1,5-a]pyridin-3-yl)propan-1-one, which was purified on a silica gel column to yield 700 mg of pure intermediate along with 3.53 g of starting material. 700 mg of 1-(2-isopropylpyrazolo[1,5-a]pyridin-3-yl)propan-1-one was reacted with 600 μl of 1M t-BuOK in t-BuOH at −20° C. for 20 minutes, followed by the addition of 600 μl of isoamylnitrite at 0° C. and stirring at RT overnight. The mixture was quenched with saturated NH4Cl and extracted with EtOAc to provide 1.2 g of crude product, which was purified on a silica gel column to furnish 314 mg of (Z)-2-(hydroxyimino)-1-(2-isopropylpyrazolo[1,5-a]pyridin-3-yl)propan-1-one. Compound 1083.

Example 49

Synthesis of 4-(2-isopropylpyrazolo[1,5-a]pyridin-3-yl)-1H-imidazole-2(3H)-thione

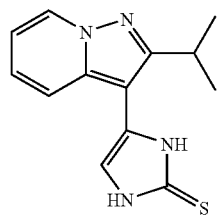

A mixture of 200 mg (0.63 mmol) of 2-chloro-1-(2-isopropylpyrazolo[1,5-a]pyridin-3-yl)ethanone, 100 mg of thiourea and 100 μl of HOAc were stirred in 1.5 ml of dioxane at 60-700 C for 30 minutes. 197 mg of 4-(2-isopropylpyrazolo[1,5-a]pyridin-3-yl)-1H-imidazole-2(3H)-thione was obtained after workup. Compound 1085.

Example 50

Synthesis of 4-(2-isopropylpyrazolo[1,5-a]pyridin-3-yl)thiazol-2(5H)-imine

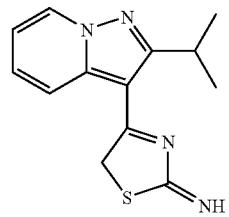

A mixture of 200 mg (0.63 mmol) of 2-chloro-1-(2-isopropylpyrazolo[1,5-a]pyridin-3-yl)ethanone, 100 mg of thiourea and 160 mg of sodium hydride were stirred in 2 ml of dioxane containing 120 μl of H$_2$O at 60-70° C. for 30 minutes. 100 mg of 4-(2-isopropylpyrazolo[1,5-a]pyridin-3-yl)thiazol-2(5H)-imine was obtained after workup. Compound 1087.

Example 51

Synthesis of 1-(2-isopropylpyrazolo[1,5-a]pyridin-3-yl)-1-oxopropan-2-yl acetate

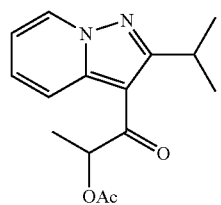

A solution of 2-chloro-1-(2-isopropylpyrazolo[1,5-a]pyridin-3-yl)propan-1-one (1.0 g, 1 equivalent) and potassium acetate (0.6 g, 1.5 equivalents) in 5 mL of DMF was stirred at room temperature for 2 days. The solution was worked up with ethyl acetate and water to give a crude oil. The oil was purified by silica gel flash column chromatography to furnish 1-(2-isopropylpyrazolo[1,5-a]pyridin-3-yl)-1-oxopropan-2-yl acetate (0.95 g, 86% yield) as a paste. Compound 1067.

Example 52

Synthesis of 2-hydroxy-1-(2-isopropylpyrazolo[1,5-a]pyridin-3-yl)propan-1-one

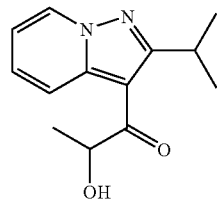

A solution of 1-(2-isopropylpyrazolo[1,5-a]pyridin-3-yl)-1-oxopropan-2-yl acetate (0.33 g, 1 equivalent) and 1M NaOH (1.5 mL, 1.25 equivalents) in 3 mL of THF was stirred at room temperature for 24 hours. The solution was worked up with ethyl acetate and saturated NaHCO3. The crude solid obtained was recrystallized from ethyl acetate and hexane to provide 2-hydroxy-1-(2-isopropylpyrazolo[1,5-a]pyridin-3-yl)propan-1-one (0.27 g, 96% yield) as a white solid. Compound 1068.

Example 53

Synthesis of 1-(2-isopropylpyrazolo[1,5-a]pyridin-3-yl)-2-methoxypropan-1-one

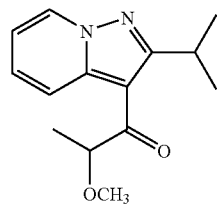

A solution of 2-hydroxy-1-(2-isopropylpyrazolo[1,5-a]pyridin-3-yl)propan-1-one (0.6 g, 1 equivalent), silver oxide (5 g, 8 equivalents), and methyl iodide (2.5 mL, 15 equivalents) in 2 mL of THF was stirred in a sealed tube at room temperature for 26 hours. The mixture was filtered to remove precipitated solids. The filtrate was worked up with ethyl acetate and saturated NaHCO3. The crude oil obtained was purified by silica gel flash column chromatography to give 1-(2-isopropylpyrazolo[1,5-a]pyridin-3-yl)-2-methoxypropan-1-one as an oil. Compound 1069.

Example 54

Synthesis of 2-isopropylpyrazolo[1,5-a]pyridine-3-carbaldehyde

Upon stirring 3 mL of DMF at room temperature, neat phosphorous oxychloride (0.8 mL 1.3 equivalents) was added dropwise. The resulting mixture was stirred at room temperature for 10 minutes, followed by dropwise addition of neat 2-isopropylpyrazolo[1,5-a]pyridine (1 g, 1 equivalent). The solution was stirred at room temperature for 19 hours and poured into 100 mL of ice water. The pH of the aqueous solution was adjusted to 8 using solid NaOH. The precipitate formed was collected by filtration and dried under reduced pressure to furnish 2-isopropylpyrazolo[1,5-a]pyridine-3-carbaldehyde (0.97 g, 82% yield) as a white solid. Compound 1073.

Example 55

Synthesis of (E)-2-((2-isopropylpyrazolo[1,5-a]pyridin-3-yl)methylene)hydrazine-carboxamide

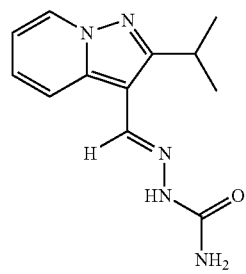

A mixture of 2-isopropylpyrazolo[1,5-a]pyridine-3-carbaldehyde (0.5 g, 1 equivalent), semicarbazide hydrochloride (0.35 g, 1.2 equivalents), and triethylamine (0.4 mL, 1.1 equivalent) in 5 mL of methanol was reflux for 30 minutes. The solution was concentrated and the crude solids produced were extracted with THF, and the mixture was filtered through a 1 inch thick layer of sodium sulfate on top of a thin pad of silica gel to remove the ammonium salt. The filtrate was concentrated and the solid deposited was recrystallized from THF and hexanes to give (E)-2-((2-isopropylpyrazolo[1,5-a]pyridin-3-yl)methylene)hydrazinecarboxamide (0.46 g, 70% yield) as a yellow solid. Compound 1074.

Example 56

Synthesis of S-1-(2-isopropylpyrazolo[1,5-a]pyridin-3-yl)-1-oxopropan-2-yl ethanethioate

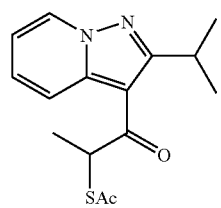

A solution of 2-chloro-1-(2-isopropylpyrazolo[1,5-a]pyridin-3-yl)propan-1-one (0.9 g, 1 equivalent) and potassium thioacetate (0.61 g, 1.5 equivalents) in 4 mL of DMF was stirred at room temperature for 1 hour. The resulting solution was worked up with EtOAc and water. The crude product was purified by silica gel flash column chromatography to give S-1-(2-isopropylpyrazolo[1,5-a]pyridin-3-yl)-1-oxopropan-2-yl ethanethioate (0.58 g, 55% yield) as a yellow solid. Compound 1081.

Example 57

Synthesis of 2-isopropylpyrazolo[1,5-a]pyridine-3-carboxylic acid

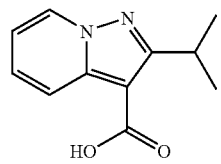

A mixture of 2-isopropylpyrazolo[1,5-a]pyridine-3-carbaldehyde (1.5 g, 1 equivalent) and potassium permanganate (2.9 g, 2.1 equivalents) in 10 mL of THF was stirred at room temperature for 2 days. A solution of potassium hydroxide (2.2 g, 5 equivalents) in 10 mL of water was added and the resulting solution was stirred at room temperature for 2 hours. The mixture was filtered to remove insoluble solids and the filtrate was extracted to remove unreacted aldehyde. The remaining aqueous solution was acidified with concentrated HCl and the precipitates were collected by filtration and dried under reduced pressure to give 2-isopropylpyrazolo[1,5-a]pyridine-3-carboxylic acid (0.98 g, 60% yield) as a solid. Compound 1079.

Example 58

Synthesis of 1-(2-isopropylpyrazolo[1,5-a]pyridin-3-yl)ethanone

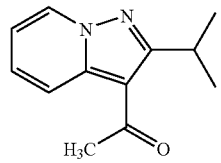

Solid aluminum chloride (0.82 g, 2 equivalents) was added to a solution of acetyl chloride (0.24 mL, 1.1 equivalents) in 1 mL of dichloromethane and the solution was stirred at room temperature for 40 minutes. Neat 2-isopropylpyrazolo[1,5-a]pyridine (0.5 g, 1 equivalent) was added dropwise to this solution at room temperature (exotherm was observed), and the resulting solution was stirred at room temperature for 20 hours and worked up with EtOAc and saturated NaHCO₃. The crude product was purified by silica gel flash column chromatography to give 1-(2-isopropylpyrazolo[1,5-a]pyridin-3-yl)ethanone (0.29 g, 46% yield) as a solid. Compound 1080.

Example 59

Synthesis of 3-(2-Isopropyl-pyrazolo[1,5-a]pyridin-3-yl)-phenylamine

A general synthetic procedure for Suzuki reactions utilized to synthesize compounds 1100-1104 and 1111-1112 is provided below. The particular synthesis shown below is for compound 1100.

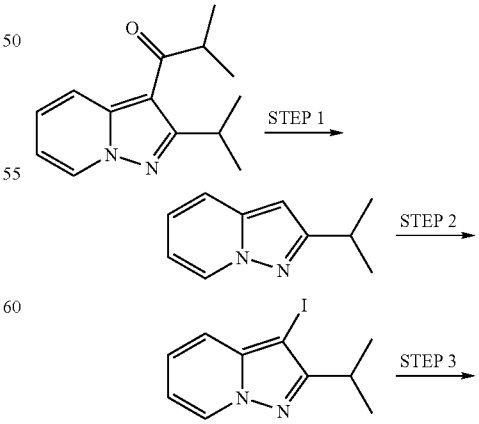

-continued

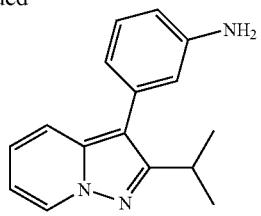

Step 1. 1-(2-Isopropyl-pyrazolo[1,5-a]pyridin-3-yl)-2-methyl-propan-1-one (30.0 g, 115 mmole), water (100 ml), and concentrated sulfuric acid (100 ml) were combined and stirred at 130° C. for 18 hours. The mixture was cooled to room temperature and poured into a solution of ice (400 g) and water (200 ml). The solution was neutralized with sodium hydroxide solution and extracted with chloroform. The organic layer was dried over sodium sulfate, filtered, and concentrated in vacuo. The oil was purified by vacuum distillation to give 14.9 g (81%) of 2-isopropyl-pyrazolo[1,5-a]pyridine. $^1$H-NMR (250 MHz, DMSO-$d_6$) δ 8.37 (d, J=7.3 Hz, 1H), 7.41 (d, J=9.0 Hz, 1H), 7.00 (t, J=7.3 Hz, 1H), 6.66 (t, J=7.5 Hz, 1H), 6.28 (s, 1H), 3.16 (sept, J=7.0 Hz, 1H), 1.35 (d, J=6.8 Hz, 6H).

Step 2. 2-Isopropyl-pyrazolo[1,5-a]pyridine (18.42 g, 115 mmol) and N-iodosuccinimide (28.45 g, 126 mmol) were dissolved in a mixture of 1,2-dichloroethane (300 ml) and tetrahydrofuran (300 ml). The mixture was stirred at reflux for 18 hours. The mixture was cooled and concentrated in vacuo. The crude material was purified by silica gel flash chromatography (0 to 20% ethyl acetate in hexanes) to give 30.9 g (94%) of 3-iodo-2-isopropyl-pyrazolo[1,5-a]pyridine. $^1$H-NMR (250 MHz, CDCl$_3$) δ 8.36 (d, J=7.0 Hz, 1H), 7.36 (d, J=9.0 Hz, 1H), 7.12 (t, J=7.9 Hz, 1H), 6.67 (t, J=7.6 Hz, 1H), 3.20 (sept, J=7.0 Hz, 1H), 1.37 (d, J=6.8 Hz, 6H).

Step 3. To a 20 ml microwave reaction vial was added 3-iodo-2-isopropyl-pyrazolo[1,5-a]pyridine (690 mg, 2.41 mmol), 3-aminophenylboronic acid monohydrate (411 mg, 2.65 mmol), [1,1'-bis(diphenylphosphino)ferrocene]dichloropalladium(II) complex with dichloromethane (197 mg, 0.24 mmol), acetonitrile (8 ml), and 1 M aqueous Na$_2$CO$_3$ solution (5 ml). The mixture was placed in a microwave reactor for 2 hours at 140° C. The reaction mixture was concentrated in vacuo, and the crude material partitioned between dichloromethane and water. The organic layer was separated, dried over sodium sulfate, filtered, and concentrated in vacuo. The crude material was purified by silica gel flash chromatography (0 to 30% ethyl acetate in hexanes) to give 205 mg (34%) of 3-(2-isopropyl-pyrazolo[1,5-a]pyridin-3-yl)-phenylamine. $^1$H-NMR (250 MHz, DMSO-$d_6$) δ 8.40 (d, J=7.0 Hz, 1H), 7.44 (d, J=9.0 Hz, 1H), 7.25-7.18 (m, 1H), 7.03-6.97 (m, 1H), 6.81 (d, J=7.3 Hz, 1H), 6.71 (s, 1H), 6.67-6.62 (m, 2H), 3.65 (broad s, 2H), 3.35 (sept, J=6.9 Hz, 1H), 1.35 (d, J=6.8 Hz, 6H). LC/MS 252.3 m/z (M+H$^+$). Compound 1100.

Example 60

Synthesis of 4-(2-Isopropyl-pyrazolo[1,5-a]pyridin-3-yl)-phenylamine

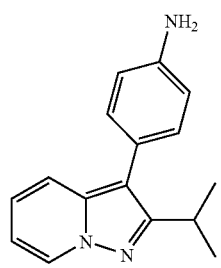

4-(2-Isopropyl-pyrazolo[1,5-a]pyridin-3-yl)-phenylamine was prepared from 3-iodo-2-isopropyl-pyrazolo[1,5-a]pyridine and 4-aminophenylboronic acid monohydrate following the method used in Step 3 of the synthesis of 3-(2-Isopropyl-pyrazolo[1,5-a]pyridin-3-yl)-phenylamine as in Example 59 above (134 mg, 18%). $^1$H-NMR (250 MHz, DMSO-$d_6$) δ 8.58 (d, J=7.0 Hz, 1H), 7.42 (d, J=7.8 Hz, 1H), 7.14-7.04 (m, 3H), 6.77 (t, J=7.0 Hz, 1H), 6.67 (d, J=8.5 Hz, 2H), 5.15 (s, 2H), 3.23 (sept, J=6.8 Hz, 1H), 1.26 (d, J=7.0 Hz, 6H). LC/MS 252.3 m/z (M+H$^+$). Compound 1101.

Example 61

Synthesis of 2-Isopropyl-3-(4-morpholin-4-yl-phenyl)-pyrazolo[1,5-a]pyridine

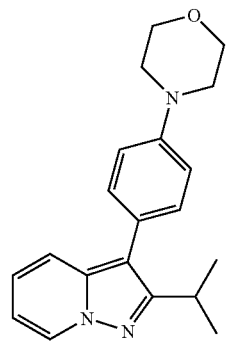

2-Isopropyl-3-(4-morpholin-4-yl-phenyl)-pyrazolo[1,5-a]pyridine was prepared from 3-iodo-2-isopropyl-pyrazolo[1,5-a]pyridine and 4-morpholinophenylboronic acid following the method used in Step 3 of the synthesis of 3-(2-Isopropyl-pyrazolo[1,5-a]pyridin-3-yl)-phenylamine (Example 59) (157 mg, 16%). $^1$H-NMR (250 MHz, DMSO-$d_6$) δ 8.61 (d, J=6.3 Hz, 1H), 7.45 (d, J=9.0 Hz, 1H), 7.30 (d, J=7.0 Hz, 2H), 7.15-7.06 (m, 3H), 6.81 (t, J=6.5 Hz, 1H), 3.79-3.75 (m, 4H), 3.25 (sept, J=6.3 Hz, 1H), 3.22-3.15 (m, 4H), 1.27 (d, J=6.8 Hz, 6H); LC/MS 322.3 m/z (M+H⁺). Compound 1102.

Example 62

Synthesis of 2-Isopropyl-3-pyridin-4-yl-pyrazolo[1,5-a]pyridine

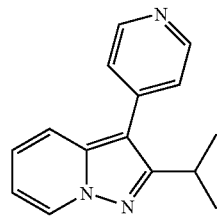

2-Isopropyl-3-pyridin-4-yl-pyrazolo[1,5-a]pyridine was prepared from 3-iodo-2-isopropyl-pyrazolo[1,5-a]pyridine and 4-pyridineboronic acid following the method used in Step 3 of the synthesis of 3-(2-Isopropyl-pyrazolo[1,5-a]pyridin-3-yl)-phenylamine (Example 59) (1584 mg, 34%). ¹H-NMR (250 MHz, DMSO-d₆) δ 8.87-8.82 (m, 3H), 8.09 (d, J=6.5 Hz, 2H), 7.95 (d, J=9.0 Hz, 1H), 7.52 (t, J=8.0 Hz, 1H), 7.11 (t, J=6.8 Hz, 1H), 3.48 (sept, J=6.8 Hz, 1H), 1.34 (d, J=6.8 Hz, 6H); LC/MS 238.3 m/z (M+H⁺). Compound 1103.

Example 63

Synthesis of 2-Isopropyl-3-(1H-pyrazol-4-yl)-pyrazolo[1,5-a]pyridine

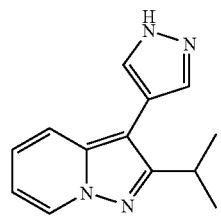

To two 20 ml microwave reaction vials were each added 3-iodo-2-isopropyl-pyrazolo[1,5-a]pyridine (486 mg, 1.69 mmol), tert-butyl 4-(4,4,5,5-tetramethyl-1,3,2-dioxaborolan-2-yl)-1-pyrazolecarboxylate (500 mg, 1.69 mmol), [1,1'-bis(diphenylphosphino)ferrocene]dichloropalladium(II) complex with dichloromethane (139 mg, 0.17 mmol), acetonitrile (8 ml), and 1 M aqueous NaHCO₃ solution (5 ml). The mixture was placed in a microwave reactor for 2 hours at 140° C. The reaction mixture from the two vials were combined and concentrated in vacuo, and the crude material was partitioned between dichloromethane and water. The organic layer was separated, dried over sodium sulfate, filtered, and concentrated in vacuo. The crude material was purified by silica gel flash chromatography (0 to 50% ethyl acetate in hexanes) to give the protected-analog. The protected analog was dissolved in 20% trifluoroacetic acid in dichloromethane (50 ml) and stirred at room temperature. The reaction was monitored by HPLC for completion (2 hours). The mixture was concentrated in vacuo, and the concentrated material was dissolved in 4N hydrochloric acid in dioxane. Ether was added to the acidic solution to precipitate out the desired material. The material was filtered and dried in vacuo under high vacuum to give 235 mg (31%) of 2-isopropyl-3-(1H-pyrazol-4-yl)-pyrazolo[1,5-a]pyridine as the hydrochloric acid salt. ¹H-NMR (250 MHz, DMSO-d₆) δ 8.70 (broad s, 1H), 8.64 (d, J=7.0 Hz, 2H), 8.07 (s, 1H), 7.61 (d, J=9.0 Hz, 1H), 7.19 (dd, J=7.8, 6.8 Hz, 1H), 6.85 (t, J=6.8 Hz, 1H), 3.30 (sept, J=7.0 Hz, 1H), 1.29 (d, J=6.8 Hz, 6H); LC/MS 227.1 m/z (M+H⁺). Compound 1104.

Example 64

Synthesis of 2-Isopropyl-3-pyridin-3-yl-pyrazolo[1,5-a]pyridine

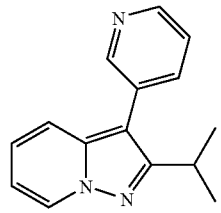

2-Isopropyl-3-pyridin-3-yl-pyrazolo[1,5-a]pyridine was prepared from 3-iodo-2-isopropyl-pyrazolo[1,5-a]pyridine and 3-pyridineboronic acid following the method used in Step 3 of the synthesis of 3-(2-Isopropyl-pyrazolo[1,5-a]pyridin-3-yl)-phenylamine (Example 59) (240 mg, 32%). ¹H-NMR (250 MHz, DMSO-d₆) δ 8.69 (d, J=7.3 Hz, 1H), 8.67 (s, 1H), 8.55 (d, J=4.0 Hz 1H), 7.85 (d, J=7.8 Hz, 2H); 7.56-7.47 (m, 1H), 7.20 (t, J=8.8 Hz, 1H), 6.89 (t, J=6.8 Hz, 1H), 3.24 (sept, J=7.0 Hz, 1H), 1.28 (d, J=6.8 Hz, 6H); LC/MS 237.9 m/z (M+H⁺). Compound 1111.

Example 65

Synthesis of 2-Isopropyl-3 (1-methyl-1H-pyrazol-4-yl)-pyrazolo[1,5-a]pyridine

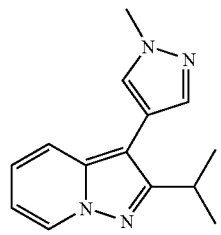

2-Isopropyl-3-(1-methyl-1H-pyrazol-4-yl)-pyrazolo[1,5-a]pyridine was prepared from 3-iodo-2-isopropyl-pyrazolo[1,5-a]pyridine and 1-Methylpyrazole-4-boronic acid pinacol ester following the method used in Step 3 of the synthesis of 3-(2-Isopropyl-pyrazolo[1,5-a]pyridin-3-yl)-phenylamine (Example 59) (138 mg, 13%). ¹H-NMR (250 MHz, DMSO-d₆) δ 8.59 (d, J=6.8 Hz, 1H), 7.93 (s, 1H), 7.64 (s, 1H), 7.58 (d, J=9.0 Hz, 1H), 7.16 (t, J=7.6 Hz, 1H), 6.80 (t, J=6.8 Hz, 1H), 3.91 (s, 3H), 3.29 (sept, J=7.0 Hz, 1H), 1.29 (d, J=6.8 Hz, 6H); LC/MS 241.1 m/z (M+H⁺). Compound 1112.

Example 66

Synthesis of Isopropyl-[4-(2-isopropylpyrazolo[1,5-a]pyridin-3-yl)-pyrimidin-2-yl]-amine A generalized procedure employed to synthesize compounds 1137, 1139, and 1134-1136 is provided below. The scheme below shows the synthesis of compound 1137.

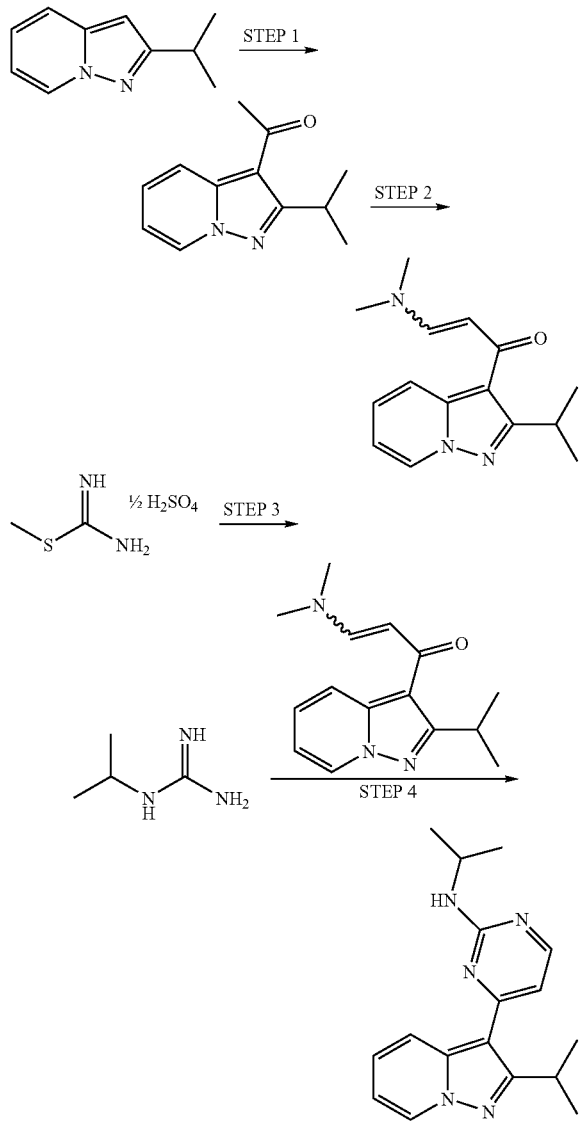

Step 1. 2-Isopropyl-pyrazolo[1,5-a]pyridine (10.00 g, 66.7 mmol), acetic anhydride (100 ml), and concentrated sulfuric acid (10 drops) were combined and stirred for 3 hours at reflux. The reaction mixture was cooled to room temperature and poured into ice water (300 ml). The mixture was quenched with 2 N sodium hydroxide until the pH>10, and the quenched solution was extracted with ethyl acetate. The organic layer was dried over sodium sulfate, filtered, and concentrated in vacuo. The crude material was purified by silica gel flash chromatography (0 to 40% ethyl acetate in hexanes) to give 11.8 g (87%) of 1-(2-isopropyl-pyrazolo[1,5-a]pyridin-3-yl)-ethanone. ¹H-NMR (250 MHz, DMSO-d₆) δ 8.47 (d, J=6.8 Hz, 1H), 8.12 (d, J=9.0 Hz, 1H), 7.38 (t, J=7.3 Hz, 1H), 6.89 (t, J=6.0 Hz, 1H), 3.76 (sept, J=6.9 Hz, 1H), 2.60 (s, 3H), 1.39 (d, J=6.8 Hz, 6H); LC/MS 203.3 m/z (M+H⁺).

Step 2. 1-(2-Isopropyl-pyrazolo[1,5-a]pyridin-3-yl)-ethanone (7.56 g, 3.74 mmol) and N,N-dimethylformamide dimethyl acetal (80 ml) were combined and stirred at reflux for 24 hours. The reaction mixture was concentrated in vacuo, and fresh N,N-dimethylformamide dimethyl acetal (80 ml) was added to the concentrated reaction mixture and stirred at reflux for 24 hours. The reaction mixture was concentrated in vacuo once again, and a third portion of N,N-dimethylformamide dimethyl acetal (80 ml) was added to the concentrated reaction mixture and stirred at reflux for a third 24 hour period. The reaction mixture was concentrated in vacuo, and the crude material was purified by silica gel flash chromatography (0 to 40% acetone in dichloromethane) to give 4.30 g (44%) of a 2:1 mixture of E-3-dimethylamino-1-(2-isopropyl-pyrazolo[1,5-a]pyridin-3-yl)-propenone and Z-3-dimethylamino-1-(2-isopropyl-pyrazolo[1,5-a]pyridin-3-yl)-propenone. ¹H-NMR (250 MHz, CDCl₃) δ 8.37 (d, J=6.8 Hz, 1H), 7.99 (d, J=9.0 Hz, 1H), 7.69 (d, J=12.5 Hz, 1H), 7.17 (t, J=7.0 Hz, 1H), 6.72 (t, J=6.0 Hz, 1H), 5.49 (d, J=12.5 Hz, 1H), 3.70 (sept, J=6.8 Hz, 1H), 2.95 (s, 6H), 1.37 (d, J=7.0 Hz, 6H); LC/MS 258.4 m/z (M+H⁺) for E-3-dimethylamino-1-(2-isopropyl-pyrazolo[1,5-a]pyridin-3-yl)-propenone.

¹H-NMR (250 MHz, CDCl₃) δ 8.39 (d, J=6.8 Hz, 1H), 8.00 (d, J=9.0 Hz, 1H), 7.71 (d, J=12.3 Hz, 1H), 7.17 (t, J=6.8 Hz, 1H), 6.73 (t, J=7.0 Hz, 1H), 5.50 (d, J=12.3 Hz, 1H), 3.72 (sept, J=6.9 Hz, 1H), 2.97 (s, 6H), 1.39 (d, J=7.0 Hz, 6H); LC/MS 258.4 m/z (M+H⁺) for Z-3-dimethylamino-1-(2-isopropyl-pyrazolo[1,5-a]pyridin-3-yl)-propenone.

Step 3. Isopropylamine (9.2 ml, 108.0 mmol), 2-methyl-2-thiopseudourea sulfate (15.00 g, 107.9 mmol), and pyridine (30 ml) were combined and stirred at 30° C. for 18 hours. The mixture was concentrated in vacuo to give N-isopropyl-guanidine. LC/MS 102.1 m/z (M+H⁺).

Step 4. 3-Dimethylamino-1-(2-isopropyl-pyrazolo[1,5-a]pyridin-3-yl)-propenone (2.90 g, 11.3 mmol) and N-isopropyl-guanidine (4.00 g, 39.5 mmol) were dissolved in 2M sodium ethoxide in ethanol (150 ml), and the mixture was stirred at reflux. The reaction mixture was monitored by HPLC for completion (24 hours). The mixture was concentrated and quenched with saturated sodium bicarbonate solution. The quenched mixture was extracted with ethyl acetate. The organic layer was dried over sodium sulfate, filtered, and concentrated in vacuo. The crude material was purified by silica gel flash chromatography (0 to 10% methanol in dichloromethane). A recrystallization in methanol and hexanes gave isopropyl-[4-(2-isopropyl-pyrazolo[1,5-a]pyridin-3-yl)-pyrimidin-2-yl]-amine. The hydrochloride salt was obtained by dissolving the product in 4N hydrogen chloride in dioxane (4 ml), followed by precipitation with ether. The precipitated was dissolved in water, cooled to −78° C., and dried on a lyophilizer to obtain isopropyl-[4-(2-isopropyl-pyrazolo[1,5-a]pyridin-3-yl)-pyrimidin-2-yl]-amine as the hydrochloride salt 798 mg (24%). ¹H-NMR (250 MHz, DMSO-d₆) δ 8.87 (d, J=6.8 Hz, 1H), 8.36-8.22 (m, 2H), 7.66-7.55 (m, 1H), 7.20-7.07 (m, 2H), 4.18 (broad s, 1H), 3.72 (sept, J=6.9 Hz, 1H), 1.37 (d, J=7.0 Hz, 6H), 1.28 (d, J=6.5 Hz, 6H); LC/MS 296.3 m/z (M+H+). Compound 1137.

Example 67

Synthesis of 4-(2-Isopropyl-pyrazolo[1,5-a]pyridin-3-yl)-pyrimidin-2-ylamine

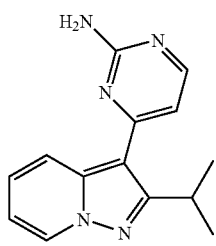

3-Dimethylamino-1-(2-isopropyl-pyrazolo[1,5-a]pyridin-3-yl)-propenone (591 mg, 2.30 mmol), guanidine hydrochloride (878 mg, 9.19 mmol), potassium carbonate (2.54 g, 18.38 mmol), and DMF (60 ml) were combined and stirred for 48 hours at 120° C. The reaction mixture was concentrated in vacuo. The crude material was purified by silica gel flash chromatography (2 to 10% methanol in dichloromethane) to give (210 mg, 36%) of 4-(2-Isopropyl-pyrazolo[1,5-a]pyridin-3-yl)-pyrimidin-2-ylamine. $^1$H-NMR (250 MHz, DMSO-$d_6$) δ 8.71 (d, J=7.3 Hz, 1H), 8.34 (d, J=9.0 Hz, 1H), 8.22 (d, J=5.5 Hz, 1H), 7.36 (dd, J=7.9, 6.8 Hz, 1H), 6.96 (t, J=6.9 Hz, 1H), 6.79 (d, J=5.3 Hz, 1H), 6.55 (s, 2H), 3.71 (sept, J=6.9 Hz, 1H), 1.34 (d, J=7.0 Hz, 6H); LC/MS 254.3 m/z (M+H+). Compound 1139.

Example 68

Synthesis of 3-[4-(2-Isopropyl-pyrazolo[1,5-a]pyridin-3-yl)-pyrimidin-2-ylamino]-propan-1-ol

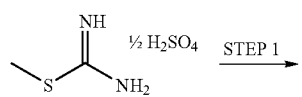

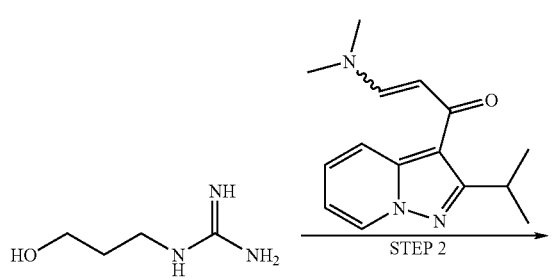

-continued

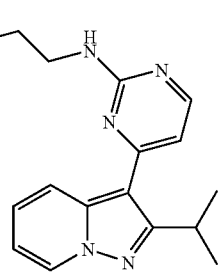

Step 1. N-(3-Hydroxy-propyl)-guanidine was prepared from 3-amino-propan-1-ol and 2-methyl-2-thiopseudourea sulfate following the method used in Step 3 of the synthesis of Isopropyl-[4-(2-isopropylpyrazolo[1,5-a]pyridin-3-yl)-pyrimidin-2-yl]-amine (Example 66). LC/MS 118.2 m/z (M+H+).

Step 2. 3-[4-(2-Isopropyl-pyrazolo[1,5-a]pyridin-3-yl)-pyrimidin-2-ylamino]-propan-1-ol was prepared from 3-dimethylamino-1-(2-isopropyl-pyrazolo[1,5-a]pyridin-3-yl)-propenone and N-(3-hydroxy-propyl)-guanidine following the method used in Step 4 of the synthesis of Isopropyl-[4-(2-isopropylpyrazolo[1,5-a]pyridin-3-yl)-pyrimidin-2-yl]-amine (Example 66), except preparative-HPLC purification was used in the place of recrystallization (166 mg, 18%). $^1$H-NMR (250 MHz, DMSO-$d_6$) δ 8.85 (d, J=7.0 Hz, 1H), 8.44-8.22 (m, 3H), 7.59 (t, J=7.0 Hz, 1H), 7.18-7.05 (m, 2H), 4.07 (broad s, 1H), 3.79 (sept, J=6.9 Hz, 1H), 3.58-3.33 (m, 4H), 1.77 (pent, J=6.6 Hz, 2H), 1.37 (d, J=6.5 Hz, 6H); LC/MS 312.3 m/z (M+H+). Compound 1134.

Example 69

Synthesis of [4-(2-Isopropylpyrazolo[1,5-a]pyridin-3-yl)-pyrimidin-2-yl]-[3-(4-methyl-piperazin-1-yl)-propyl]-amine

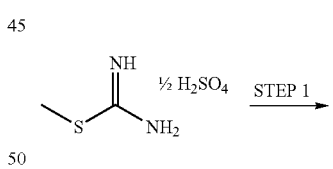

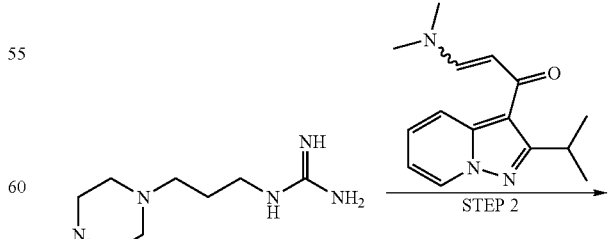

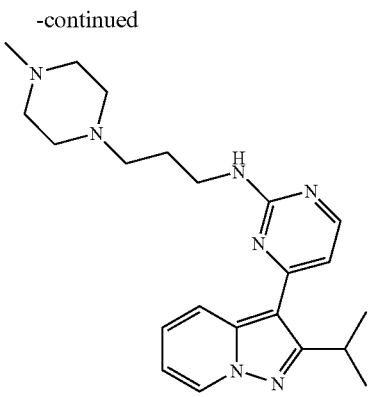

Step 1. N-[3-(4-Methyl-piperazin-1-yl)-propyl]-guanidine was prepared from 3-(4-methyl-piperazin-1-yl)-propylamine and 2-methyl-2-thiopseudourea sulfate following the method used in Step 3 of the synthesis of Isopropyl-[4-(2-isopropylpyrazolo[1,5-a]pyridin-3-yl)-pyrimidin-2-yl]-amine (Example 66). LC/MS 200.2 m/z (M+H⁺).

Step 2. [4-(2-Isopropyl-pyrazolo[1,5-a]pyridin-3-yl)-pyrimidin-2-yl]-[3-(4-methyl-piperazin-1-yl)-propyl]-amine was prepared from 3-dimethylamino-1-(2-isopropyl-pyrazolo[1,5-a]pyridin-3-yl)-propenone and N-[3-(4-methyl-piperazin-1-yl)-propyl]-guanidine following the method used in Step 4 of the synthesis of Isopropyl-[4-(2-isopropylpyrazolo[1,5-a]pyridin-3-yl)-pyrimidin-2-yl]-amine (Example 66), except preparative-HPLC purification was used in the place of recrystallization (162 mg, 19%). $^1$H-NMR (250 MHz, DMSO-$d_6$) δ 8.72 (d, J=6.8 Hz, 1H), 8.28-8.20 (m, 2H), 7.37 (t, J=7.8 Hz, 1H), 7.16-7.10 (m, 1H), 6.99 (t, J=6.6 Hz, 1H), 6.80 (d, J=7.3 Hz, 1H), 3.78 (sept, J=7.3 Hz, 1H), 2.56-2.32 (m, 10H), 2.22 (s, 3H), 2.10-2.06 (m, 2H), 1.73 (pent, J=6.9 Hz, 2H), 1.35 (d, J=6.8 Hz, 6H); LC/MS 394.3 m/z (M+H⁺). Compound 1135.

Example 70

Synthesis of Cyclopropyl-[4-(2-isopropylpyrazolo[1,5-a]pyridin-3-yl)-pyrimidin-2-yl]-amine

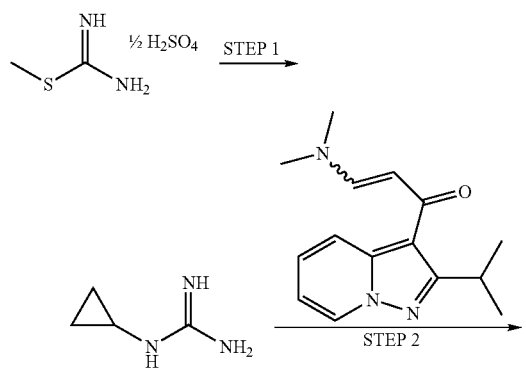

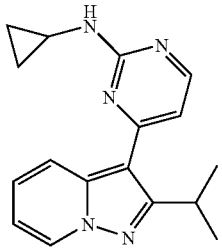

Step 1. N-Cyclopropyl-guanidine was prepared from cyclopropylamine and 2-methyl-2-thiopseudourea sulfate following the method used in Step 3 of the synthesis of Isopropyl-[4-(2-isopropylpyrazolo[1,5-a]pyridin-3-yl)-pyrimidin-2-yl]-amine (Example 66). LC/MS 100.2 m/z (M+H⁺).

Step 2. Cyclopropyl-[4-(2-isopropyl-pyrazolo[1,5-a]pyridin-3-yl)-pyrimidin-2-yl]-amine was prepared from 3-dimethylamino-1-(2-isopropyl-pyrazolo[1,5-a]pyridin-3-yl)-propenone and N-cyclopropyl-guanidine following the method used in Step 4 of the synthesis of Isopropyl-[4-(2-isopropylpyrazolo[1,5-a]pyridin-3-yl)-pyrimidin-2-yl]-amine (Example 66), except preparative-HPLC purification was used in the place of recrystallization (34 mg, 7%). $^1$H-NMR (250 MHz, DMSO-$d_6$) δ 8.86 (d, J=6.8 Hz, 1H), 8.57 (d, J=8.3 Hz, 1H), 8.27 (d, J=6.5 Hz, 1H), 7.59 (t, J=7.9 Hz, 1H), 7.19-7.10 (m, 2H), 4.62 (broad s, 1H), 3.86-3.78 (m, 1H), 2.80-2.72 (m, 1H), 1.38 (d, J=6.5 Hz, 6H), 0.90-0.84 (m, 2H), 0.70-0.64 (m, 2H); LC/MS 294.2 m/z (M+H⁺). Compound 1136.

Example 71

Synthesis of 2-Isopropyl-3-(1H-pyrazol-3-yl)-pyrazolo[1,5-a]pyridine

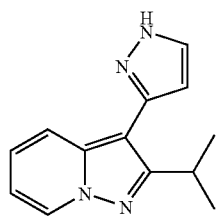

3-Dimethylamino-1-(2-isopropyl-pyrazolo[1,5-a]pyridin-3-yl)-propenone (860 mg, 3.34 mmol), hydrazine (1.0 ml, 31.85 mmol), and 2N sodium ethoxide in ethanol (70 ml) were combined and stirred at reflux for 18 hours. The mixture was cooled to room temperature and concentrated in vacuo. The dried paste was partitioned between saturated sodium bicarbonate solution and ethyl acetate. The organic layer was separated, dried over sodium sulfate, filtered and concentrated. The crude material was purified by silica gel flash chromatography (0 to 15% methanol in dichloromethane). The pure compound was dissolved in 1 N HCl dioxane (2 ml), and precipitated out of solution with ether to give 230 mg (87%) 2-isopropyl-3-(1H-pyrazol-3-yl)-pyrazolo[1,5-a]pyridine as the hydrochloride salt. $^1$H-NMR (250 MHz, DMSO-$d_6$) δ 8.66 (d, J=7.0 Hz, 1H), 7.95 (s, 1H), 7.84 (d, J=8.8 Hz, 1H), 7.26 (t, J=7.8 Hz, 1H), 6.89 (t, J=6.8 Hz, 1H), 6.60 (s, 1H), 6.55 (broad s, 1H), 3.54 (sept, J=6.5 Hz, 1H), 1.30 (d, J=6.8 Hz, 6H); LC/MS 227.1 m/z (M+H⁺). Compound 1141.

Table 1 provides a summary of exemplary compounds in accordance with the invention, including structures for each of $R_2$, $R_3$ and $R_6$, corresponding name, and cross-reference to relevant example describing synthesis or literature reference.

TABLE 1

| R2 | R3 | R6 | Ref. Code | Name | Synthesis Method |
|---|---|---|---|---|---|
|  | 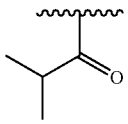 | —H | 411 | 1-(2-isopropylpyrazolo[1,5-a]pyridin-3-yl)-2-methylpropan-1-one | Example 1(b); T. Irikura, et al., U.S. Pat. No. 3,850,941 Nov. 26, 1974 |
|  | 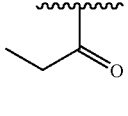 | —H | 1001 | 1-(2-isopropylpyrazolo[1,5-a]pyridin-3-yl)propan-1-one | Example 20; U.S. Pat. No. 4,097,483 |
|  | 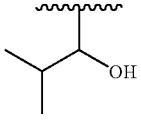 | —H | 1002 | 1-(2-isopropylpyrazolo[1,5-a]pyridin-3-yl)-2-methylpropan-1-ol | Example 21; U.S. Pat. No. 4,578,392 |
| 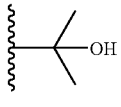 | 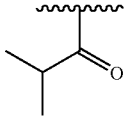 | —H | 1003 | 1-(2-(2-hydroxypropan-2-yl)pyrazolo[1,5-a]pyridin-3-yl)-2-methylpropan-1-one | K. Awano, et al., Chem. Pharm. Bull., 40, 631-38 (1992) |
|  | 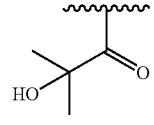 | —H | 1004 | 2-hydroxy-1-(2-isopropylpyrazolo[1,5-a]pyridin-3-yl)-2-methylpropan-1-one | K. Awano, et al., Chem. Pharm. Bull., 40, 631-38 (1992) |
|  | 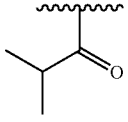 | OCH3 | 1005 | 1-(2-isopropyl-6-methoxypyrazolo[1,5-a]pyridin-3-yl)-2-methylpropan-1-one | K. Awano, et al., Chem. Pharm. Bull., 40, 639-43 (1992) |
|  | 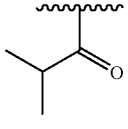 | —OH | 1006 | 1-(6-hydroxy-2-isopropylpyrazolo[1,5-a]pyridin-3-yl)-2-methylpropan-1-one | K. Awano, et al., Chem. Pharm. Bull., 40, 639-43 (1992) |
|  | 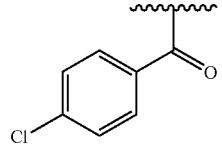 | —H | 1007 | 4-chlorophenyl)(2-isopropylpyrazolo[1,5-a]pyridin-3-yl)methanone | Example 17 |
|  | 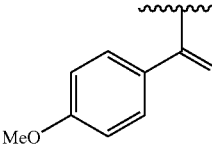 | —H | 1008 | (2-isopropylpyrazolo[1,5-a]pyridin-3-yl)(4-methoxyphenyl)methanone | Example 18 |
| 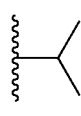 | 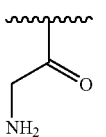 | —H | 1009 | 2-amino-1-(2-isopropylpyrazolo[1,5-a]pyridin-3-yl)ethanone | Example 1(f) |

TABLE 1-continued

| R2 | R3 | R6 | Ref. Code | Name | Synthesis Method |
|---|---|---|---|---|---|
| isopropyl | isobutyl ketoxime (=N-OH) | —H | 1012 | 1-(2-isopropylpyrazolo[1,5-a]pyridin-3-yl)-2-methylpropan-1-one oxime | Example 3 |
| isopropyl | 2-amino propanone (NH2, C=O) | —H | 1013 | 2-amino-1-(2-isopropylpyrazolo[1,5-a]pyridin-3-yl)propan-1-one | Example 2 |
| isopropyl | isobutyl O-carbamoyl oxime | —H | 1014 | 1-(2-isopropylpyrazolo[1,5-a]pyridin-3-yl)-2-methylpropan-1-one O-carbamoyl oxime | Example 4 |
| phenyl | isopropyl ketone | —H | 1015 | 2-methyl-1-(2-phenylpyrazolo[1,5-a]pyridin-3-yl)propan-1-one | Example 5; M. J. Alberti, et al., U.S. patent application publication 2004/0053942 |
| phenyl | isopropyl ketoxime | —H | 1016 | 2-methyl-1-(2-phenylpyrazolo[1,5-a]pyridin-3-yl)propan-1-one oxime | Example 6 |
| phenyl | isopropyl O-carbamoyl oxime | —H | 1017 | 2-methyl-1-(2-phenylpyrazolo[1,5-a]pyridin-3-yl)propan-1-one O-carbamoyl oxime | Example 7 |
| 4-fluorophenyl | isopropyl ketone | —H | 1018 | 1-(2-(4-fluorophenyl)pyrazolo[1,5-a]pyridin-3-yl)-2-methylpropan-1-one | Example 8; M. J. Alberti, et al., U.S. patent application publication 2004/0053942 |
| 4-fluorophenyl | isopropyl ketoxime | —H | 1019 | 1-(2-(4-fluorophenyl)pyrazolo[1,5-a]pyridin-3-yl)-2-methylpropan-1-one oxime | Example 9 |
| 4-fluorophenyl | isopropyl O-carbamoyl oxime | —H | 1020 | 1-(2-(4-fluorophenyl)pyrazolo[1,5-a]pyridin-3-yl)-2-methylpropan-1-one O-carbamoyl oxime | Example 10 |
| 4-methoxyphenyl | isopropyl ketone | —H | 1021 | 1-(2-(4-methoxyphenyl)pyrazolo[1,5-a]pyridin-3-yl)-2-methylpropan-1-one | Example 11; M. J. Alberti, et al., U.S. patent application publication 2004/0053942 |

TABLE 1-continued

| R2 | R3 | R6 | Ref. Code | Name | Synthesis Method |
|---|---|---|---|---|---|
| 4-MeO-phenyl | isopropyl C(=N-OH)- | —H | 1022 | 1-(2-(4-methoxyphenyl)pyrazolo[1,5-a]pyridin-3-yl)-2-methylpropan-1-one oxime | Example 12 |
| 4-MeO-phenyl | isopropyl C(=N-O-C(=O)NH₂)- | —H | 1023 | 1-(2-(4-methoxyphenyl)pyrazolo[1,5-a]pyridin-3-yl)-2-methylpropan-1-one O-carbamoyl oxime | Example 13 |
| 4-Cl-phenyl | isopropyl C(=O)- | —H | 1024 | 1-(2-(4-chlorophenyl)pyrazolo[1,5-a]pyridin-3-yl)-2-methylpropan-1-one | Example 14; M. J. Alberti, et al., U.S. patent application publication 2004/0053942 |
| 4-Cl-phenyl | isopropyl C(=N-OH)- | —H | 1025 | 1-(2-(4-chlorophenyl)pyrazolo[1,5-a]pyridin-3-yl)-2-methylpropan-1-one oxime | Example 15 |
| 4-Cl-phenyl | isopropyl C(=N-O-C(=O)NH₂)- | —H | 1026 | 1-(2-(4-chlorophenyl)pyrazolo[1,5-a]pyridin-3-yl)-2-methylpropan-1-one O-carbamoyl oxime | Example 16 |
| 4-F-phenyl | isopropyl C(=O)- | —CF3 | 1027 | 1-(2-(4-fluorophenyl)-6-(trifluoromethyl)pyrazolo[1,5-a]pyridin-3-yl)-2-methylpropan-1-one | Example 19; M. J. Alberti, et al., U.S. patent application publication 2004/0053942 |
| 4-F-phenyl | isopropyl C(=N-OH)- | —CF3 | 1032 | 1-(2-(4-fluorophenyl)-6-(trifluoromethyl)pyrazolo[1,5-a]pyridin-3-yl)-2-methylpropan-1-one oxime | Example 19(b). |
| 4-F-phenyl | 2-methyl-1-(isobutyryloxy)prop-1-enyl | —CF3 | 1033 | 1-(2-(4-fluorophenyl)-6-(trifluoromethyl)pyrazolo[1,5-a]pyridin-3-yl)-2-methylprop-1-enyl isobutyrate | Example 19(e); M. J. Alberti, et al., U.S. patent application publication 2004/0053942 |
| isopropyl | 1-morpholino-1-oxopropan-2-yl (α-methyl, morpholinyl ketone) | —H | 1034 | 1-(2-isopropylpyrazolo[1,5-a]pyridin-3-yl)-2-morpholinopropan-1-one hydrochloride | Example 23 |

TABLE 1-continued

| R2 | R3 | R6 | Ref. Code | Name | Synthesis Method |
|---|---|---|---|---|---|
| isopropyl | 1-(4-methylpiperazin-1-yl)propan-2-one-1-yl | —H | 1035 | 1-(2-isopropylpyrazolo[1,5-a]pyridin-3-yl)-2-(4-methylpiperazin-1-yl)propan-1-one hydrochloride | Example 24 |
| isopropyl | 1-(piperidin-1-yl)propan-2-one-1-yl | —H | 1036 | 1-(2-isopropylpyrazolo[1,5-a]pyridin-3-yl)-2-(piperidin-1-yl)propan-1-one hydrochloride | Example 25 |
| isopropyl | 1-(piperazin-1-yl)propan-2-one-1-yl | —H | 1037 | 1-(2-isopropylpyrazolo[1,5-a]pyridin-3-yl)-2-(piperazin-1-yl)propan-1-one hydrochloride | Example 26 |
| isopropyl | (3-chloropyridin-2-yl)carbonyl | —H | 1038 | (3-chloropyridin-2-yl)(2-isopropylpyrazolo[1,5-a]pyridin-3-yl)methanone | Example 27 |
| isopropyl | 2-amino-2-phenylacetyl | —H | 1039 | 2-amino-1-(2-isopropylpyrazolo[1,5-a]pyridin-3-yl)-2-phenylethanone | Example 28 |
| ethyl | propanoyl | —H | 1040 | 1-(2-ethylpyrazolo[1,5-a]pyridin-3-yl)propan-1-one | Example 29 |
| isopropyl | 2-(benzyl(methyl)amino)propanoyl | —H | 1041 | 2-(benzyl(methyl)amino)-1-(2-isopropylpyrazolo[1,5-a]pyridin-3-yl)propan-1-one | Example 30 |

TABLE 1-continued

| R2 | R3 | R6 | Ref. Code | Name | Synthesis Method |
|---|---|---|---|---|---|
| isopropyl | CH(CH3)C(O)NHCH3 | —H | 1042 | 1-(2-isopropylpyrazolo[1,5-a]pyridin-3-yl)-2-(methylamino)propan-1-one hydrochloride | Example 31 |
| isopropyl | CH(iPr)NH-cyclopropyl | —H | 1044 | N-(1-(2-isopropylpyrazolo[1,5-a]pyridin-3-yl)-2-methylpropyl)cyclopropanamine | Example 32 |
| isopropyl | C(O)-cyclopropyl | —H | 1046 | cyclopropyl(2-isopropylpyrazolo[1,5-a]pyridin-3-yl)methanone | Example 37 |
| isopropyl | CH(iPr)NHCH2-cyclopropyl | —H | 1048 | N-(cyclopropylmethyl)-1-(2-isopropylpyrazolo[1,5-a]pyridin-3-yl)-2-methylpropan-1-amine hydrochloride | Example 33 |
| isopropyl | CH(iPr)NH2 | —H | 1051 | 1-(2-isopropylpyrazolo[1,5-a]pyridin-3-yl)-2-methylpropan-1-amine hydrochloride | Example 35 |
| 4-fluorophenyl | CH(CH3)C(O)NH2 | —H | 1052 | 2-amino-1-(2-(4-fluorophenyl)pyrazolo[1,5-a]pyridin-3-yl)propan-1-one hydrochloride | Example 36 |
| —OCH3 | CH(CH3)C(O)iPr | —H | 1055 | 1-(2-methoxypyrazolo[1,5-a]pyridin-3-yl)-2-methylpropan-1-one | Example 39 |
| —OCH3 | CH(CH3)C(O)NH2 | —H | 1057 | 2-amino-1-(2-methoxypyrazolo[1,5-a]pyridin-3-yl)propan-1-one | Example 40 |
| isopropyl | CH(Et)C(O)NH2 | —H | 1060 | 2-amino-1-(2-isopropylpyrazolo[1,5-a]pyridin-3-yl)butan-1-one | Example 41 |

TABLE 1-continued

| R2 | R3 | R6 | Ref. Code | Name | Synthesis Method |
|---|---|---|---|---|---|
| isopropyl | 2-amino-4-methylpentanoyl (leucinyl) | —H | 1061 | 2-amino-1-(2-isopropylpyrazolo[1,5-a]pyridin-3-yl)-4-methylpentan-1-one | Example 42 |
| isopropyl | 1-oxopropan-2-yl acetate (OAc) | —H | 1067 | 1-(2-isopropylpyrazolo[1,5-a]pyridin-3-yl)-1-oxopropan-2-yl acetate | Example 51 |
| isopropyl | 2-hydroxypropanoyl (OH) | —H | 1068 | 2-hydroxy-1-(2-isopropylpyrazolo[1,5-a]pyridin-3-yl)propan-1-one | Example 52 |
| isopropyl | 2-methoxypropanoyl (OMe) | —H | 1069 | 1-(2-isopropylpyrazolo[1,5-a]pyridin-3-yl)-2-methoxypropan-1-one | Example 53 |
| 4-fluorophenyl | propanoyl | —H | 1070 | 1-(2-(4-fluorophenyl)pyrazolo[1,5-a]pyridin-3-yl)propan-1-one | Example 43 |
| dimethylamino | isobutyryl | —H | 1072 | 1-(2-(dimethylamino)pyrazolo[1,5-a]pyridin-3-yl)-2-methylpropan-1-one | Example 44 |
| isopropyl | formyl (CHO) | —H | 1073 | 2-isopropylpyrazolo[1,5-a]pyridine-3-carbaldehyde | Example 54 |
| isopropyl | (E)-methylene-semicarbazone | —H | 1074 | (E)-2-((2-isopropylpyrazolo[1,5-a]pyridin-3-yl)methylene)hydrazinecarboxamide | Example 55 |
| dimethylamino | 2-aminopropanoyl (NH2) | —H | 1075 | 2-amino-1-(2-(dimethylamino)pyrazolo[1,5-a]pyridin-3-yl)propan-1-one | Example 45 |

TABLE 1-continued

| R2 | R3 | R6 | Ref. Code | Name | Synthesis Method |
|---|---|---|---|---|---|
| isopropyl | 2-amino-pentyl ketone (NH2 on α-carbon) | —H | 1077 | 2-amino-1-(2-isopropylpyrazolo[1,5-a]pyridin-3-yl)hexan-1-one | Example 46 |
| isopropyl | CO2H | —H | 1079 | 2-isopropylpyrazolo[1,5-a]pyridine-3-carboxylic acid | Example 57 |
| isopropyl | C(O)CH3 | —H | 1080 | 1-(2-isopropylpyrazolo[1,5-a]pyridin-3-yl)ethanone | Example 58 |
| isopropyl | 2-amino-3-methoxypropanoyl | —H | 1082 | 2-amino-1-(2-isopropylpyrazolo[1,5-a]pyridin-3-yl)-3-methoxypropan-1-one | Example 47 |
| isopropyl | C(O)C(=NOH)CH3 | —H | 1083 | (Z)-2-(hydroxyimino)-1-(2-isopropylpyrazolo[1,5-a]pyridin-3-yl)propan-1-one | Example 48 |
| isopropyl | imidazole-2(3H)-thione-4-yl | —H | 1085 | 4-(2-isopropylpyrazolo[1,5-a]pyridin-3-yl)-1H-imidazole-2(3H)-thione | Example 49 |
| isopropyl | 2-imino-thiazol-4-yl | —H | 1087 | 4-(2-isopropylpyrazolo(1,5-a]pyridin-3-yl)thiazol-2(5H)-imine | Example 50 |
| isopropyl | 3-aminophenyl | —H | 1100 | 3-(2-Isopropyl-pyrazolo(1,5-a]pyridin-3-yl)-phenylamine | Example 59 |
| isopropyl | 4-aminophenyl | —H | 1101 | 4-(2-Isopropyl-pyrazolo[1,5-a]pyridin-3-yl)-phenylamine | Example 60 |

TABLE 1-continued

| R2 | R3 | R6 | Ref. Code | Name | Synthesis Method |
|---|---|---|---|---|---|
| 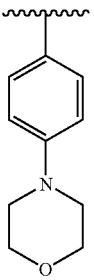 | 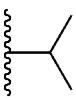 | —H | 1102 | 2-Isopropyl-3-(4-morpholin-4-yl-phenyl)-pyrazolo[1,5-a]pyridine | Example 61 |
| 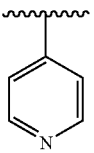 |  | —H | 1103 | 2-Isopropyl-3-pyridin-4-yl-pyrazolo[1,5-a]pyridine | Example 62 |
| 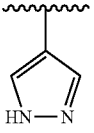 |  | —H | 1104 | 2-Isopropyl-3-(1H-pyrazol-4-yl)-pyrazolo[1,5-a]pyridine | Example 63 |
| 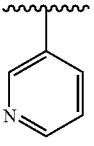 |  | —H | 1111 | 2-Isopropyl-3-pyridin-3-yl-pyrazolo[1,5-a]pyridine | Example 64 |
| 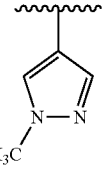 | 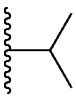 | —H | 1112 | 2-Isopropyl-3-(1-methyl-1H-pyrazol-4-yl)-pyrazolo[1,5-a]pyridine | Example 65 |
| 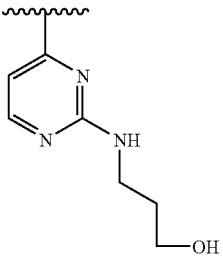 | | —H | 1134 | 3-[4-(2-Isopropyl-pyrazolo[1,5-a]pyridin-3-yl)-pyrimidin-2-ylamino]-propan-1-ol | Example 68 |

TABLE 1-continued

| R2 | R3 | R6 | Ref. Code | Name | Synthesis Method |
|---|---|---|---|---|---|
| isopropyl | 4-(pyrimidin-2-yl)amino with 3-(4-methylpiperazin-1-yl)propyl | —H | 1135 | [4-(2-Isopropylpyrazolo[1,5-a]pyridin-3-yl)-pyrimidin-2-yl]-[3-(4-methyl-piperazin-1-yl)-propyl]-amine | Example 69 |
| isopropyl | 4-(2-isopropylamino-pyrimidin-4-yl) | —H | 1137 | Isopropyl-(4-(2-isopropylpyrazolo[1,5-a]pyridin-3-yl)-pyrimidin-2-yl]-amine | Example 66 |
| isopropyl | 4-(2-aminopyrimidin-4-yl) | —H | 1139 | 4-(2-Isopropyl-pyrazolo[1,5-a]pyridin-3-yl)-pyrimidin-2-ylamine | Example 67 |
| isopropyl | 1H-pyrazol-3-yl | —H | 1141 | Isopropyl-3-(1H-pyrazol-3-yl)-pyrazolo[1,5-a]pyridine | Example 71 |
| isopropyl | 2-(cyclopropylamino)propan-1-one | —H | 1045 | 2-(cyclopropylamino)-1-(2-isopropylpyrazolo[1,5-a]pyridin-3-yl)propan-1-one hydrochloride | Example 34 |
| cyclopropyl | cyclopropylcarbonyl | —H | 1047 | cyclopropyl(2-cyclopropylpyrazolo[1,5-a]pyridin-3-yl)methanone | Example 38 |
| isopropyl | 2-methylprop-1-enyl | —H | 1049 | 2-isopropyl-3-(2-methylprop-1-enyl)pyrazolo[1,5-a]pyridine | Example 79 |
| cyclopropyl | 2-methylpropan-1-one | —H | 1050 | 1-(2-cyclopropylpyrazolo[1,5-a]pyridin-3-yl)-2-methylpropan-1-one | Example 75 |

TABLE 1-continued

| R2 | R3 | R6 | Ref. Code | Name | Synthesis Method |
|---|---|---|---|---|---|
| isopropyl | 2-methyl-3-(piperidin-1-yl)propanoyl | —H | 1063 | 1-(2-isopropylpyrazolo[1,5-a]pyridin-3-yl)-2-methyl-3-(piperidin-1-yl)propan-1-one hydrochloride | Example 78 |
| isopropyl | 3-amino-2-methylpropanoyl | —H | 1065 | 3-amino-1-(2-isopropylpyrazolo[1,5-a]pyridin-3-yl)-2-methylpropan-1-one hydrochloride | Example 77 |
| isopropyl | 3-(benzylamino)-2-methylpropanoyl | —H | 1066 | 3-(benzylamino)-1-(2-isopropylpyrazolo[1,5-a]pyridin-3-yl)-2-methylpropan-1-one hydrochloride | Example 76 |
| isopropyl | 2-(benzylamino)propanoyl | —H | 1071 | 2-(benzylamino)-1-(2-isopropylpyrazolo[1,5-a]pyridin-3-yl)propan-1-one | Example 80 |
| isopropyl | 2-(acetylthio)propanoyl | —H | 1081 | S-1-(2-isopropylpyrazolo[1,5-a]pyridin-3-yl)-1-oxopropan-2-yl ethanethioate | Example 56 |

Example 72

Mechanical Allodynia Measured by Response to Von Frey Fibers for Exemplary Substituted Pyrazolo[1,5-a]pyridine Compounds of the Invention To induce allodynia, male Sprague-Dawley rats underwent chronic constriction injury (CCI) to the sciatic nerve as described by Bennett and Xie, Pain 1988; 33(1):87-107. The plantar surface of the hind paws was stimulated with von Frey filaments (Stoelting) to induce a withdrawal response by blinded personnel. The bending force of fiber required to induce a 50% withdrawal response was calculated following CCI surgery (pre-dosing baseline). N=5-6 allodynic rats received a single intraperitoneal administration of test compound or vehicle. Two hours post-dosing, 50% paw withdrawal threshold was determined again by blinded testers using von Frey filaments. The change in 50% withdrawal threshold relative to pre-dosing baseline is reported in Table 2 for various substituted pyrazolo[1,5-a]pyridine compounds of the invention.

Compounds exhibiting a chronic constriction injury threshold of 1.0 gram or greater are preferred for use in treating neuropathic pain, while compounds exhibiting a chronic constriction injury threshold of 1.5 grams or greater, or even more preferably 2.0 grams or greater are particularly preferred. Thus, compounds 1009, 1012, 1013, 1014, 1019, 1026, 1085, 1103, and 1137 are particularly advantageous for treating allodynia. In summary, the aforementioned compounds are particularly efficacious in treating neuropathic pain, as demonstrated using a mechanical allodynia rat model.

Figure 2:
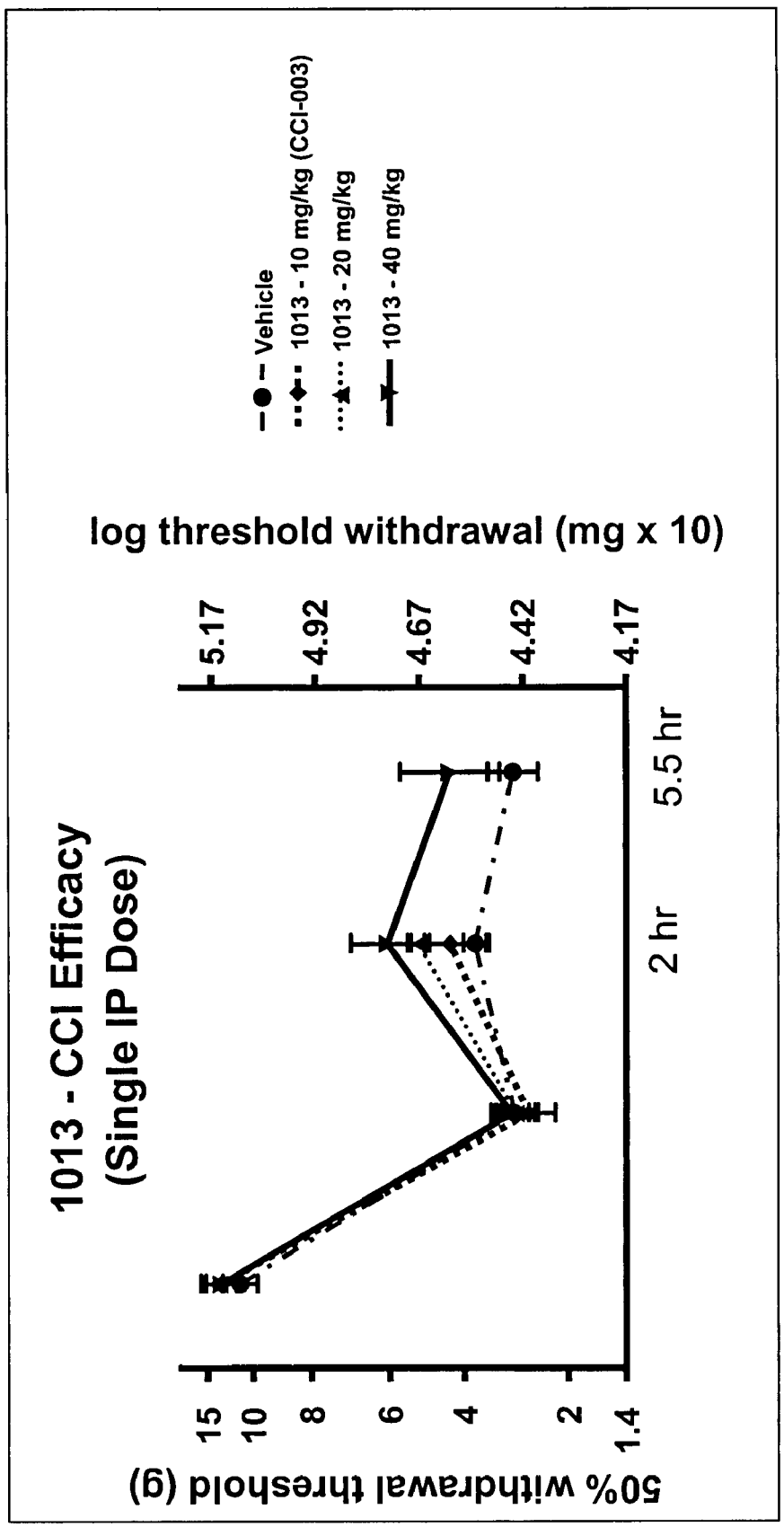
FIG. 2 is a plot similarly demonstrating the results of an illustrative compound of the invention in a rat chronic constriction injury model for assessing efficacy in treatment of neuropathic pain as described in detail in Example 72. The model employed measures mechanical allodynia by response to von Frey Fibers. The plot shows the 50% paw withdrawal threshold in grams for rats administered the vehicle or compound 1013 intraperitoneally at three different doses (10 mg/kg; 20 mg/kg; and 40 mg/kg) at various time points post-administration.

A plot of 50% paw withdrawal threshold in grams for the vehicle and compound 1014 administered intraperitoneally at two different doses at various time points post-administration is provided in FIG. 1. Similarly, FIG. 2 is a plot of 50% withdrawal threshold in grams for the vehicle and compound 1013 administered intraperitoneally at three different doses (10 mg/kg; 20 mg/kg; and 40 mg/kg) at various time points post-administration.

Example 73

Inhibition of PDE for Exemplary Substituted Pyrazolo[1,5-a]pyridine Compounds of the Invention In a 96-well plate, phosphodiesterase (PDE) enzyme (0.5-1 mU/well) derived from bovine brain (Sigma) was combined with 5 uM cAMP substrate (Sigma). Test compounds (0-200 uM) or vehicle (0.5% DMSO) were added to the enzyme/substrate and incubated for 1 hour. Using a PDELight® kit (Cambrex), the amount of AMP produced in the reaction from the hydrolysis of cAMP was quantified using PDELight AMP Detection Reagent which converts the AMP directly to ATP. The assay uses luciferase, which catalyses the formation of light from the newly formed ATP and luciferin. The luminescence was read on a Victor Light 1420 luminometer. $IC_{50}$ calculations were plotted using a nonlinear regression curve fit.

$IC_{50}$ results are reported in Table 2 for various substituted pyrazolo[1,5-a]pyridine compounds of the invention. Compounds exhibiting an $IC_{50}$ of less than about 50 μM, preferably less than about 20 μM, more preferably less than about 15 μM, and even more preferably less than about 10 μM are preferred in terms of their ability to effectively inhibit phosphodiesterase. Thus, in this regard, out of those compounds evaluated, preferred compounds include 1004, 1006, 1008, 1012, 1019, 1022, 1024, 1025, and 1026.

Example 74

Lipopolysaccharide-Stimulation of Peripheral Blood Mononuclear Cells (PBMCs) for Exemplary Substituted Pyrazolo[1,5-a]pyridine Compounds of the Invention $IC_{50}$ values were determined for representative compounds of the invention based upon their ability to inhibit LPS-induced cytokine production in human peripheral blood mononuclear cells. Human PBMCs (peripheral blood mononuclear cells) were isolated over a Ficoll gradient from buffy coats obtained from the local Red Cross. $10^6$ PBMC cells/well were seeded in 24-well tissue culture plates in RPMI 1640 medium supplemented with 10% human serum, hepes buffer and sodium pyruvate. The cells were treated with 0.1% DMSO (vehicle) or test compounds (1, 10, and 100 uM) 30 minutes prior to activation with LPS (lipopolysaccharide) (*E. Coli*) at 10 ng/mL. 6-10 hours post LPS stimulation the culture supernatants were collected and levels of cytokines TNF-α and IL-1β were quantified by ELISA (R&D Systems) and/or Luminex (Linco Diagnostics). $IC_{50}$ calculations were plotted using a nonlinear regression curve fit for exemplary substituted pyrazolo[1,5-a]pyridine compounds of the invention; results are provided in Table 2.

As demonstrated by the results in Table 2, certain compounds of the invention are particularly useful for treating inflammatory conditions, as indicated by their ability to suppress LPS-mediated cytokine release in the above-described assay. In this regard, i.e., for use as an anti-inflammatory agent, preferred compounds are those having an $IC_{50}$ of less than or equal to about 50 μM, preferably less than about 40 μM, and even more preferably, less than about 30 μM. Thus, preferred compounds for use as anti-inflammatory agents include 1001, 1004, 1006, 1007, 1008, 1009, 1013, 1014, 1018, and 1024. Since chronic inflammatory diseases are caused by prolonged production of several proinflammatory cytokines such as TNF-α and IL-1β, the ability of a compound to effectively inhibit LPS-stimulated production of such cytokines provides an indication of its efficacy in treating one or more inflammatory conditions.

TABLE 2

Summary of Assay Results for Substituted Pyrazolo[1,5-α]pyridine Compounds

| Compound Ref. Code | Mechanical Allodynia ΔWT (grams) (note a) | PDE Inhibition, μM ($IC_{50}$) (note b) | TNF-α, μM ($IC_{50}$) (note c) | IL-1β, μM ($IC_{50}$) (note c) |
|---|---|---|---|---|
| 411 | 2.31-3.53 | 10.3 | 5 | 17.9 |
| 1001 | 0 | 58 | 13 | >100 |
| 1002 | 0.79 | >200 | >100 | >100 |
| 1003 | 0 | >100 | | |
| 1004 | 0.48 | 12.6 | 28.8 | >100 |
| 1005 | 0.17 | 59.5 | 76 | |
| 1006 | 0 | 29.6 | 1.3 | 14.7 |
| 1007 | 0.92 | >200 | 13 | 29.7 |
| 1008 | 0.84 | 5.8 | 50 | >100 |
| 1009 | 1.15 | >200 | 25 | 99 |
| 1012 | 1.56 | 40 | >100 | 99 |
| 1013 | 10 mg/kg: 1.04<br>20 mg/kg: 1.33<br>40 mg/kg: 3.16<br>25 mg/kg PO: 1.39 | >200 | 13.6 | >100 |

TABLE 2-continued

Summary of Assay Results for Substituted Pyrazolo[1,5-α]pyridine Compounds

| Compound Ref. Code | Mechanical Allodynia ΔWT (grams) (note a) | PDE Inhibition, μM ($IC_{50}$) (note b) | TNF-α, μM ($IC_{50}$) (note c) | IL-1β, μM ($IC_{50}$) (note c) |
|---|---|---|---|---|
| 1014 | 10 mg/kg: 2.18 | 100 | 1.3 | 1 |
|  | 20 mg/kg: 3.73 |  |  |  |
| 1015 | 0.51 | 80 | >100 | >100 |
| 1016 | 0 | 75 | >100 | >100 |
| 1017 | 0.91 | >200 |  |  |
| 1018 | 0 | >200 | 32.7 | >100 |
| 1019 | 1.4 | 40 | >100 | >100 |
| 1020 |  | >200 |  |  |
| 1021 | 0.45 | >200 |  |  |
| 1022 | 0 | 23.9 |  |  |
| 1023 |  | 156 |  |  |
| 1024 | 0.43 | 18.2 |  |  |
| 1025 | 0.81 | 23.0 |  |  |
| 1026 | 1.14 | 27.7 |  |  |
| 1027 | 0 | >200 |  |  |
| 1034 | 10 mg/kg: 1.71 | 43.3 |  |  |
|  | 20 mg/kg: 0.54 |  |  |  |
| 1035 | 0 | 198 |  |  |
| 1036 | 0 | >200 |  |  |
| 1037 | 0 | >200 |  |  |
| 1038 | 0.32 | 26.4 |  |  |
| 1039 | 0.05 | 8.2 |  |  |
| 1040 | 0.12 | 27.1 |  |  |
| 1041 | 0.22 | 21.5 |  |  |
| 1042 | 10 mg/kg: 0.37 | 31.9 |  |  |
|  | 20 mg/kg: 0.22 |  |  |  |
| 1044 | 0.08 | >200 |  |  |
| 1045 | 0 | 61.1 |  |  |
| 1046 | 0 | 33.3 |  |  |
| 1047 | 0.68 | 15.4 |  |  |
| 1048 | 0 | >200 |  |  |
| 1049 | 0 | 92.5 |  |  |
| 1050 | 0 |  |  |  |
| 1051 | 0.29 |  |  |  |
| 1052 | 10 mg/kg: 0.39 |  |  |  |
|  | 20 mg/kg: 0.31 |  |  |  |
| 1055 | 10 mg/kg: 2.80 |  |  |  |
|  | 20 mg/kg: 0 |  |  |  |
| 1057 | 0.06 |  |  |  |
| 1060 | 10 mg/kg: 1.87 |  |  |  |
|  | 20 mg/kg: 0.74 |  |  |  |
| 1061 | 0 |  |  |  |
| 1063 | 0 |  |  |  |
| 1065 | 0.91 |  |  |  |
| 1066 | 0.1 |  |  |  |
| 1067 | 0.46 |  |  |  |
| 1068 | 0.7 |  |  |  |
| 1069 | 0.13 |  |  |  |
| 1070 | 0 |  |  |  |
| 1071 | 0.57 |  |  |  |
| 1072 | 1.48 lethargy |  |  |  |
| 1073 | 0 |  |  |  |
| 1074 | 3.64 lethargy |  |  |  |
| 1075 | 0.67 |  |  |  |
| 1077 | 0.41 |  |  |  |
| 1080 | 1.14 |  |  |  |
| 1081 | 0.07 |  |  |  |
| 1082 | 0.5 |  |  |  |
| 1083 | 0 |  |  |  |
| 1085 | 1.93 |  |  |  |
| 1100 | 0 |  |  |  |
| 1101 | 0.02 |  |  |  |
| 1102 | 0 |  |  |  |
| 1103 | 1.54 |  |  |  |
| 1104 | 0.86 |  |  |  |
| 1111 | 0 |  |  |  |
| 1112 | 0 |  |  |  |
| 1134 | 0 |  |  |  |
| 1135 | 0 |  |  |  |

TABLE 2-continued

Summary of Assay Results for Substituted Pyrazolo[1,5-α]pyridine Compounds

| Compound Ref. Code | Mechanical Allodynia ΔWT (grams) (note a) | PDE Inhibition, μM ($IC_{50}$) (note b) | TNF-α, μM ($IC_{50}$) (note c) | IL-1β, μM ($IC_{50}$) (note c) |
| --- | --- | --- | --- | --- |
| 1137 | 3.26 | | | |
| 1139 | 0.21 | | | |
| 1141 | 1.04 | | | |

(note a)
Mechanical allodynia measured by response to von Frey fibers at 2 hr post dosing (10 mg/kg, IP, or as indicated); reported as change from pre-dosing withdrawal threshold;
(note b)
PDE obtained from brain extract using cAMP as substrate;
(note c)
Inhibition of LPS-stimulated cytokine release from PBMCs.

Example 75

Synthesis of 1-(2-cyclopropylpyrazolo[1,5-a]pyridin-3-yl)-2-methylpropan-1-one

Step 1. Cyclopropyl(2-cyclopropylpyrazolo[1,5-a]pyridin-3-yl)methanone (1.0 g, 4.42 mmol) was heated in benzene (80 ml) to reflux in a Dean-Stark apparatus, in the presence of TsOH monohydrate (0.8 g, 4.21 mmol, 0.95 eq.), for 10 minutes. Freshly distilled ethylene glycol (2.0 g, 32.24 mmol, 7.3 eq.) was added and the biphasic solution maintained at reflux for a further 12 hours. The reaction was cooled to rt and extracted with a saturated $NaHCO_3$ solution (25 ml×3). The organic phase was dried over $Na_2SO_4$, filtered and concentrated in-vacuo. Purification by column chromatography (4:1 hexane:ethyl acetate) provided 2-cyclopropylpyrazolo[1,5-a]pyridine as a faintly yellow oil (0.61 g, 3.85 mmol, 87%).

IR (film) v=3435, 3081, 2088, 1635, 1523, 1435, 1331, 1254, 1221, 1021 $cm^{-1}$; $^1$H NMR (300 MHz, $CDCl_3$) δ=8.31 (d, J=6.9 Hz, 1H), 7.32 (d, J=9.0 Hz, 1H), 6.96 (t, J=7.8 Hz, 1H), 6.57 (t, J=7.0 Hz, 1H), 6.11 (s, 1H), 2.02-2.14 (m, 1H), 0.96-1.05 (m, 2H), 0.83-0.91 (m, 2H); $^{13}$C NMR (75 MHz, $CDCl_3$) δ=158.2, 140.9, 127.9, 123.0, 116.9, 110.4, 92.5, 9.3, 8.6 MS (EI) m/z (%): 159 (12), 158 (100), 157 (90), 156 (27), 155 (11), 132 (18), 131 (15), 130 (28), 118 (15), 80 (14), 79 (12), 78 (15), 69 (21), 64 (11), 57 (10), 44 (19), 41 (14).

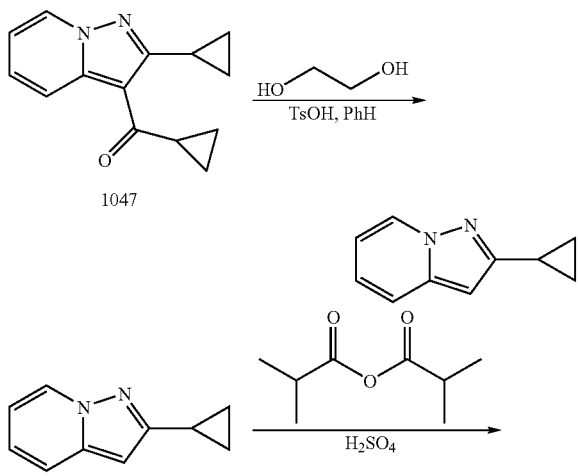

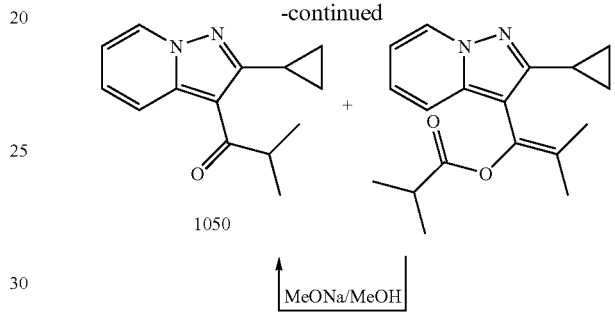

Step 2. 2-cyclopropylpyrazolo[1,5-a]pyridine (0.61 g, 3.85 mmol) was heated to 140° C. in isobutyric anhydride (10.0 ml, 60.24 mmol) for 15 minutes. $H_2SO_4$ (conc., 5 drops) was added to the reaction, and the temperature maintained for a further 12 hours. The reaction was cooled to 50° C., and NaOH (50% aqueous) added until the pH of the solution was ~11. On cooling to rt, the aqueous mixture was extracted with $CHCl_3$ (4×25 ml). The organic phases were combined, dried over $Na_2SO_4$, filtered and concentrated in-vacuo to provide a 1:2 mixture of 1-(2-cyclopropylpyrazolo[1,5-a]pyridin-3-yl)-2-methylpropan-1-one and the enol ester 1-(2-cyclopropylpyrazolo[1,5-a]pyridin-3-yl)-2-methylprop-1-enyl isobutyrate. The crude mixture was treated with freshly prepared MeOH/MeONa (1.0 M, 10 ml) at rt for 8 hours. The reaction was quenched with $NH_4Cl$ (aqueous), extracted with $CHCl_3$ (4×25 ml) and the organic phases combined, dried over $Na_2SO_4$, filtered and concentrated in-vacuo. The title compound, 1-(2-cyclopropylpyrazolo[1,5-a]pyridin-3-yl)-2-methylpropan-1-one, was recovered as a yellow crystalline solid (0.35 g, 1.53 mmol, 39.7%). MP 108-109° C.; IR (film) v=3077, 2972, 2930, 2871, 1638, 1622, 1538, 1499, 1466, 1424, 1360, 1260, 1207, 1145, 1081 $cm^{-1}$; $^1$H NMR (300 MHz, $CDCl_3$) δ=8.35 (d, J=6.8 Hz, 1H), 8.22 (d, J=8.9 Hz, 1H), 7.36 (t, J=7.9 Hz, 1H), 6.88 (t, J=6.5 Hz, 1H), 3.59 (sept, J=6.8 Hz, 1H), 2.42-2.56 (m, 1H), 1.27 (d, J=6.8 Hz, 6H), 1.05-1.18 (m, 4H); $^{13}$C NMR (75 MHz, $CDCl_3$) δ=199.7, 158.3, 142.3, 128.4, 127.6, 119.2, 113.4, 110.4, 38.0, 18.8, 9.5, 8.4; MS (EI) m/z (%): 228 (26), 200 (17), 186 (13), 185 (100), 157 (37), 117 (12), 78 (13), 41 (19); HRMS (EI) calc'd for $C_{14}H_{16}N_2O$: 228.1263. found: 228.1259; Anal. Calc'd for $C_{10}H_{12}N_2$: C, 73.66%; H, 7.06%. Found: C, 73.13%; H, 6.95%. Compound 1050.

Example 76

Synthesis of 3-(benzylamino)-1-(2-isopropylpyrazolo[1,5-a]pyridin-3-yl)-2-methylpropan-1-one hydrochloride To 2-isopropyl-pyrazolo[1,5-a]pyridine (6.80 g, 42.50 mmol) in n-propionic anhydride (15 mL, 97%) at 140° C. was added concentrated $H_2SO_4$ (0.5 ml). The mixture was maintained at 140° C. overnight, cooled to room temperature basified with NaOH (aqueous 50%) until pH>11. The aqueous layer was extracted with chloroform (3×100 mL), dried ($Na_2SO_4$), filtered and concentrated. The crude product was purified by flash column chromatography (100% hexane, 9:1 hexane:ethyl acetate) to afford 1-(2-isopropylpyrazolo[1,5-a]pyridin-3-yl)propan-1-one (4.81 g, 22.27 mmol, 53%) as a yellow oil. 1-(2-isopropylpyrazolo[1,5-a]pyridin-3-yl)propan-1-one (0.500 g, 2.3 mmol), paraformaldehyde (0.069 g, 2.3 mmol), and benzylamine hydrochloride (0.329 g, 2.3 mmol) were added to a 5-mL round bottom flask. To this ethanolic hydrochloride (1 mL, 1.25% concentrated HCl in ethanol) was added and the mixture was heated to reflux for 16 hours. The mixture was then cooled and diluted with $Et_2O$ (5 mL) and 1M NaOH (aq) (10 mL). The aqueous layer was then extracted with $Et_2O$ (4×5 mL). The combined organic layers were washed with brine, dried ($Na_2SO_4$), filtered and concentrated to afford a dark brown oil. This oil was subjected to flash column chromatography (10% gradient of EtOAc/hexane ranging from 0 to 90%) which afforded 0.073 g (9.5% yield) of 3-(benzylamino)-1-(2-isopropylpyrazolo[1,5-a]pyridin-3-yl)-2-methylpropan-1-one as a pale yellow oil.

$^1$H NMR (300 MHz, $CDCl_3$) δ=8.47 (d, J=7.0 Hz, 1H), 8.03 (d, J=8.9 Hz, 1H), 7.37 (dt, J=8.9, 0.9 Hz, 1H), 7.30-7.25 (m, 4H), 7.23-7.18 (m, 1H), 6.89 (dt, J=7.0, 0.9 Hz, 1H), 3.78 (sept, J=6.9 Hz, 1H), 3.78 (s, 2H), 3.54-3.43 (m, 1H), 3.17 (dd, J=11.7, 7.5 Hz, 1H), 2.69 (dd, J=11.7, 5.7 Hz, 1H), 1.40 (d, J=6.9 Hz, 3H), 1.39 (d, J=6.9 Hz, 3H), 1.25 (d, J=6.9 Hz, 3H); $^{13}$C NMR (75 MHz, $CDCl_3$) δ=198.1, 164.4, 141.4, 140.4, 129.2, 128.3, 128.0, 127.7, 126.8, 118.9, 113.1, 109.3, 54.2, 52.3, 44.8, 27.7, 22.4, 22.1, 16.0; MS (EI) m/z 336 (M+1, 0.5), 335 (M$^+$, 1.5), 217 (19.1), 216 (20.7), 188 (13.3), 187 (100.0), 106 (11.2), 91 (66.2); HRMS (EI) calcd for $C_{21}H_{25}N_3O$: 335.1998. found: 335.1995.

To MeOH (2 mL) cooled in an ice bath under argon was added AcCl (0.047 mL) dropwise. This solution was stirred for 10 minutes before adding dropwise to 3-(benzylamino)-1-(2-isopropylpyrazolo[1,5-a]pyridin-3-yl)-2-methylpropan-1-one (0.200 g) in dry $Et_2O$ (5 mL), which was also cooled in an ice bath. The solvent was evaporated and the residue was treated with hexane (1 ml). the solvent was evaporated and a yellow solid was obtained. This solid was stirred in 10 mL of a solution containing MeOH (1%) and $Et_2O$ (99%) for 8 hours. The solid was filtered, washed with $Et_2O$ and dried under reduced pressure to afford 172 mg of 3-(benzylamino)-1-(2-isopropylpyrazolo[1,5-a]pyridin-3-yl)-2-methylpropan-1-one hydrochloride as a pale yellow solid. mp=171-175° C. ($Et_2O$, pentane), IR (KBr) v=3428, 3034, 2965, 2784, 25589, 2425, 1642, 1538, 1507, 1481, 1440, 1360, 1264, 1210, 1188, 972; $^1$H NMR (600 MHz, DMSO-$d_6$) δ=9.60 (bs, 1H), 9.23 (bs, 1H), 8.86 (d, J=6.8 Hz, 1H), 8.09 (d, J=9.1 Hz, 1H), 7.56-7.68 (m, 3H), 7.37-7.47 (m, 3H), 7.15 (tr, J=6.8 Hz, 1H), 4.15-4.23 (m, 2H), 3.87-3.95 (m, 1H), 3.74 (sept, J=6.8 Hz, 1H), 3.34-3.42 (m, 1H), 2.94-3.01 (m, 1H), 1.33 (d, J=6.8 Hz, 3H), 1.28 (d, J=6.8 Hz, 3H), 1.22 (d, J=7.6 Hz, 3H); $^{13}$C NMR (150 MHz, $CDCl_3$) δ=194.8, 164.4, 140.9, 132.3, 130.7, 130.6, 129.6, 129.4, 129.0, 118.7, 114.7, 107.4, 48.2, 41.3, 27.6, 22.9, 22.3, 17.1; MS (FAB) m/z 337 (M+1, 25.5), 336 (M$^+$, 100.0), 218 (16.7), 217 (99.6), 187 (28.1), 173 (17.8), 161 (13.1), 120 (31.9); HRMS (FAB) calcd for $C_{21}H_{26}N_3O$: 336.2076; found: 336.2066. Compound 1066.

Example 77

Synthesis of 3-amino-1-(2-isopropylpyrazolo[1,5-a]pyridin-3-yl)-2-methylpropan-1-one hydrochloride

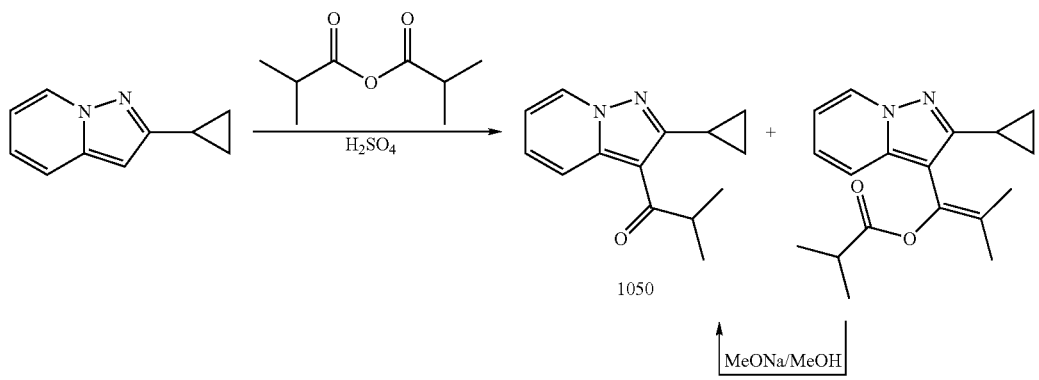

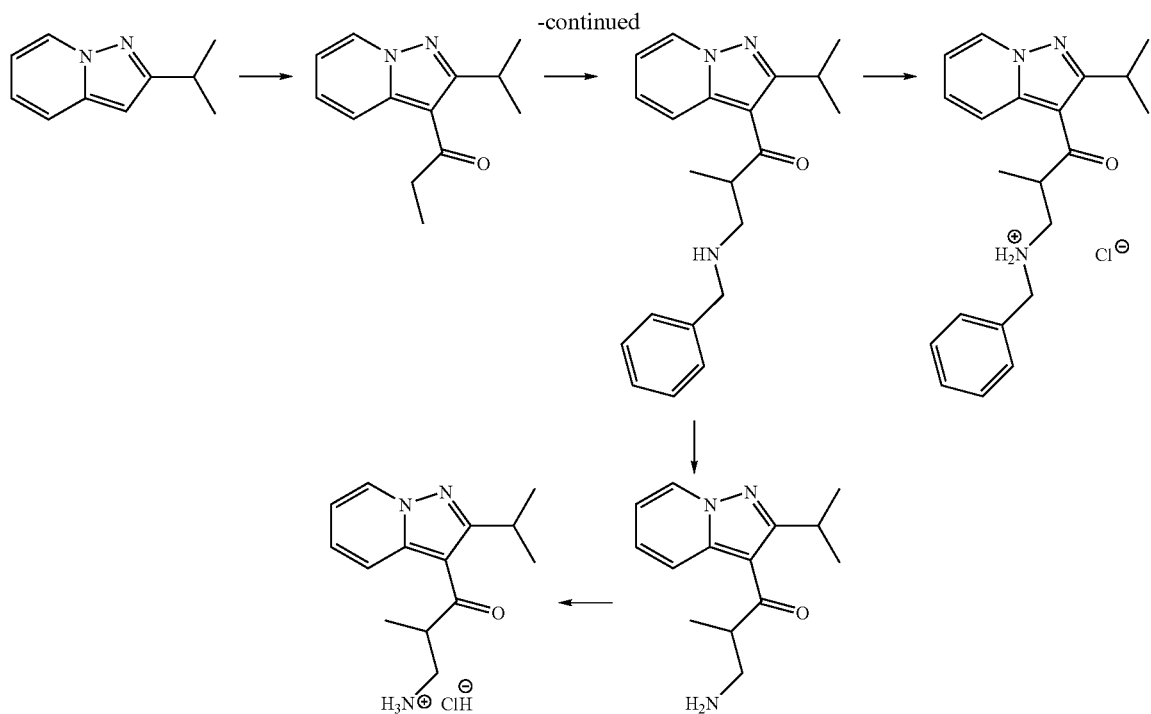

3-(benzylamino)-1-(2-isopropylpyrazolo[1,5-a]pyridin-3-yl)-2-methylpropan-1-one (0.312 g, 0.93 mmol) was dissolved in MeOH (25 mL). The flask was evacuated and flushed with argon (3 cycles). Pd on C (0.312 g, 10 wt %) was added in small portions. The flask was then evacuated and flushed with hydrogen (4 cycles). The heterogeneous mixture was then vigorously stirred for 2 hours before evacuating and flushing with argon (3 cycles). The mixture was then filtered through Celite, washing with MeOH (50 mL), and concentrated. The dark yellow oil was then subjected to flash column chromatography (100% MeOH) while monitoring the fractions with HPLC and $^1$H NMR. The first major fractions contained 0.164 g (53% recovered starting material); which was followed by 0.0379 g (16% yield) of 3-amino-1-(2-isopropylpyrazolo[1,5-a]pyridin-3-yl)-2-methylpropan-1-one as a yellow oil.

$^1$H NMR (300 MHz, CDCl$_3$) δ=8.46 (d, J=6.9 Hz, 1H), 8.04 (d, J=9.0 Hz, 1H), 7.37 (dt, J=9.0, 0.6 Hz, 1H), 6.88 (dt, J=6.9, 0.6 Hz, 1H), 3.77 (sept, J=6.9 Hz, 1H), 3.39-3.28 (m, 1H), 3.22-3.16 (m, 1H), 2.80-2.77 (m, 1H), 1.38 (d, J=6.9 Hz, 3H), 1.37 (d, J=6.9 Hz, 3H), 1.21 (d, J=6.9 Hz, 3H); MS (EI) m/z 246 (M+1, 2.9), 245 (M$^+$, 17.5) 213 (14.0), 188 (14.0), 187 (100.0), 161 (16.1), 160 (27.9), 117 (10.6), 86 (46.7), 84 (72.6), 71 (10.7), 57 (23.5), 55 (10.2), 49 (15.1), 47 (18.8), 44 (11.1), 43 (24.9), 41 (16.7); HRMS (EI) calcd for C$_{14}$H$_{19}$N$_3$O: 245.1528; found: 245.1533.

To MeOH (2 mL) cooled in an ice bath under argon was added AcCl (0.12 mL) dropwise. This solution was stirred for 10 minutes before adding dropwise to 3-amino-1-(2-isopropylpyrazolo[1,5-a]pyridin-3-yl)-2-methylpropan-1-one (0.340 g) in dry Et$_2$O (10 mL), which was also cooled in an ice bath. Precipitate was formed immediately which was filtered, washing with Et$_2$O (4×15 mL) affording 0.390 g of an yellow solid. This solid was stirred in 20 mL of a solution containing MeOH (1%) and pentane (99%) for 8 hours. The solvent was then aspirated to afford 313 mg of 3-amino-1-(2-isopropylpyrazolo[1,5-a]pyridin-3-yl)-2-methylpropan-1-one hydrochloride as a yellow solid.

mp=110-115° C. (MeOH, pentane), $^1$H NMR (600 MHz, CDCl$_3$) δ=8.87 (d, J=7.2 Hz, 1H), 8.08 (d, J=8.4 Hz, 1H), 8.01 (br s, 3H), 7.66 (t, J=8.4 Hz, 1H), 7.16 (t, J=7.2 Hz, 1H), 3.76-3.71 (m, 2H), 3.25-3.23 (m, 1H), 2.91-2.89 (m, 1H), 1.34 (d, J=7.2 Hz, 3H), 1.30 (d, J=6.6 Hz, 3H), 1.21 (d, J=7.2 Hz, 3H); $^{13}$C NMR (150 MHz, CDCl$_3$) δ=195.1, 164.4, 140.9, 130.6, 129.7, 118.7, 114.7, 107.6, 42.0, 40.7, 27.7, 22.9, 22.3, 16.5; IR (KBr) ν=3400, 3369, 2967, 2873, 1630 cm$^{-1}$; MS (FAB+) m/z 247 (M+1, 17.7), 246 (M$^+$, 100.0), 217 (24.2), 187 (21.5), 161 (71.7), 147 (11.6), 136 (10.9), 91 (10.3), 73 (42.4), 43 (10.0), 30 (22.9); HRMS (FAB+) calcd for C$_{14}$H$_{20}$N$_3$O: 246.1606, found 246.1604. Compound 1065.

Example 78

Synthesis of 1-(2-isopropylpyrazolo[1,5-a]pyridin-3-yl)-2-methyl-3-(piperidin-1-yl)propan-1-one hydrochloride

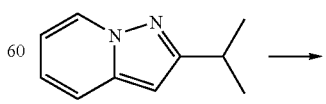

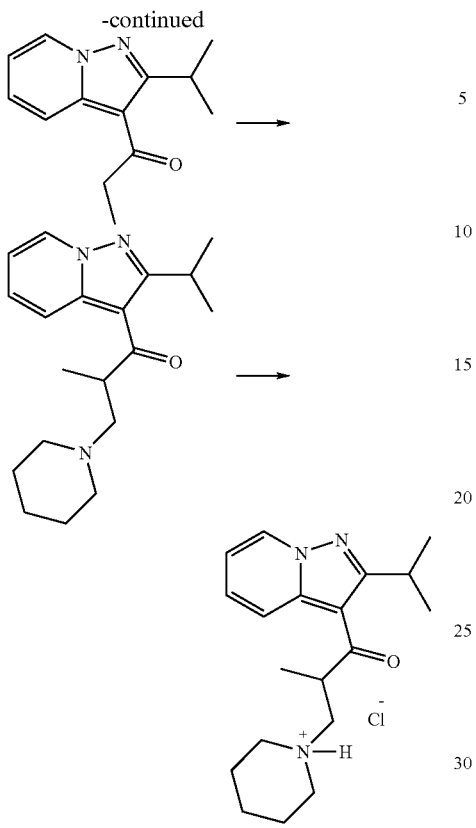

1-(2-isopropylpyrazolo[1,5-a]pyridin-3-yl)propan-1-one (0.500 g, 2.3 mmol) (1.10 g, 5.1 mmol) was dissolved in dry DMF (8.8 mL). To this solution was added piperidine hydrochloride (0.985 g, 8.1 mmol) and paraformaldehyde (0.306 g, 10.2 mmol). The vial was purged with argon, sealed and heated to 85° C. for 16 hours, whereupon all of the starting material had been consumed. The vial was cooled to room temperature and then diluted with Et$_2$O (10 mL) and H$_2$O (5 mL). The layers were separated and the pH of the aqueous layer was adjusted to pH 12 before extracting with Et$_2$O (5×5 mL). The combined organic layers were then washed with H$_2$O (5×5 mL), brine (10 mL), dried (Na$_2$SO$_4$), filtered and concentrated to afford brown oil (1.88 g). This crude oil was subjected to flash column chromatography (40% EtOAc/hexane and then 100% MeOH) to yield 1-(2-isopropylpyrazolo[1,5-a]pyridin-3-yl)-2-methyl-3-(piperidin-1-yl)propan 1-one (1.34 g, 84% yield) as yellow oil.

IR (thin film) v=2965, 2933, 1646, 1630, 1457, 1439; $^1$H NMR (300 MHz, CDCl$_3$) δ=8.46 (d, J=6.9 Hz, 1H), 8.08 (d, J=9.0 Hz, 1H), 7.37 (dt, J=9.0, 1.2 Hz, 1H), 6.88 (dt, J=6.9, 1.2 Hz, 1H), 3.75 (sept, J=6.9 Hz, 1H), 3.57-3.46 (m, 1H), 2.46-2.38 (m, 5H), 1.52-1.45 (m, 4H), 1.40-1.35 (m, 2H), 1.39 (d, J=6.6 Hz, 3H), 1.38 (d, J=6.9 Hz, 3H), 1.22 (d, J=6.9 Hz, 3H); $^{13}$C NMR (75 MHz, CDCl$_3$) δ=198.7, 164.0, 141.4, 129.1, 127.5, 118.9, 11.31, 109.5, 62.0, 54.9, 42.4, 27.7, 25.9, 24.2, 22.4, 22.2, 16.9; MS (EI) m/z 313 (M$^+$, 2.1), 228 (17.9), 213 (14.0), 187 (30.3), 99 (12.3), 98 (100.0), 97 (17.2), 84 (12.9), 41 (13.2); HRMS (EI) calcd for C$_{19}$H$_{27}$N$_3$O: 313.2154. found: 313.2164. To MeOH (1 mL) cooled in an ice bath under argon was added AcCl (0.18 mL) dropwise.

This solution was stirred for 10 minutes before adding dropwise to 1-(2-isopropylpyrazolo[1,5-a]pyridin-3-yl)-2-methyl-3-(piperidin-1-yl)propan-1-one (0.661 g) in dry Et$_2$O (10 mL), which was also cooled in an ice bath. Precipitate was formed immediately which was filtered, washing with Et$_2$O (4×15 mL) affording 0.419 g of an off-white solid. This solid was then stirred in 20 mL of a solution containing MeOH (2%), pentane (60%) and EtOAc (38%) for 3 hours. The solvent was then aspirated to afford 323 mg of 1-(2-isopropylpyrazolo[1,5-a]pyridin-3-yl)-2-methyl-3-(piperidin-1-yl)propan-1-one hydrochloride as a pure white solid.

mp=166-167° C. (MeOH, pentane, EtOAc), IR (KBr) v=3435, 2973, 2953, 2936, 1635, 1503, 1475, 1441, 1185; $^1$H NMR (600 MHz, DMSO) δ=10.41 (s, 1H), 8.86 (d, J=6.0 Hz, 1H), 8.18 (d, J=9.0 Hz, 1H), 7.65-7.62 (m, 1H), 7.16-7.14 (m, 1H), 4.03-3.95 (m, 1H), 3.79-3.74 (m, 1H), 3.70-3.66 (m, 1H), 3.44 (d, J=12.0 Hz, 1H), 3.23 (d, J=12.0 Hz, 1H), 3.06 (dt, J=12.0, 3.6 Hz, 1H), 2.98-2.92 (m, 1H), 2.85-2.76 (m, 1H), 1.84-1.77 (m, 1H), 1.75-1.70 (m, 3H), 1.64-1.61 (m, 1H), 1.39-1.33 (m, 1H), 1.31 (d, J=6.9 Hz, 3H), 1.28 (d, J=6.9 Hz, 3H), 1.22 (d, J=7.3 Hz, 3H); $^{13}$C NMR (150 MHz, DMSO) δ=194.0, 164.3, 140.4, 130.1, 129.3, 118.4, 114.3, 106.7, 57.1, 53.5, 52.1, 39.4, 27.2, 22.2, 22.2, 22.1, 21.7, 21.1, 17.6; MS (FAB+) m/z 315 (M+1, 7.7), 314 (M$^+$, 33.3), 98 (100.0); HRMS (FAB+) calcd for C$_{19}$H$_{28}$N$_3$O: 314.2232. found: 314.2169; Anal. Calcd for C$_{19}$H$_{28}$N$_3$OCl: C, 65.22%; H, 8.07%. Found: C, 65.37%; H, 8.09%. Compound 1063.

Example 79

Synthesis of 2-isopropyl-3-(2-methylprop-1-enyl)pyrazolo[1,5-a]pyridine

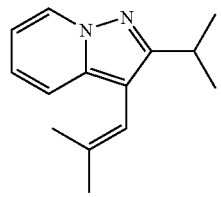

To a solution of 9.2 g of 1-(2-isopropylpyrazolo[1,5-a]pyridin-3-yl)-2-methylpropan-1-one in 25 ml of MeOH was added 1.5 g of NaBH$_4$. The solution was stirred at RT overnight. 10.25 g of oily 1-(2-isopropylpyrazolo[1,5-a]pyridin-3-yl)-2-methylpropan-1-ol was obtained after workup. 1.05 g of 1-(2-isopropylpyrazolo[1,5-a]pyridin-3-yl)-2-methylpropan-1-ol in 10 ml of benzene was treated with 0.92 g of PCl$_5$ and 1 ml of pyridine with stirring for 3 hours at RT. The crude 2-isopropyl-3-(2-methylprop-1-enyl)pyrazolo[1,5-a]pyridine obtained was purified on an Al$_2$O$_3$ column to furnish 255 mg of pure compound. Compound 1049.

Example 80

Synthesis of 2-(benzylamino)-1-(2-isopropylpyrazolo[1,5-a]pyridin-3-yl)propan-1-one

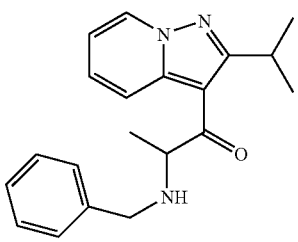

To 2.51 g of 2-chloro-1-(2-isopropylpyrazolo[1,5-a]pyridin-3-yl)propan-1-one and 2.25 ml of benzylamine in 20 ml of MeOH was added 10 mg of NaI and the solution was refluxed for 4 hours, then stirred at RT overnight. Crude 2-(benzylamino)-1-(2-isopropylpyrazolo[1,5-a]pyridin-3-yl)propan-1-one was purified on an Al$_2$O$_3$ column to yield 2.51 g of pure compound. Compound 1071.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed herein, as such are presented by way of example. The intent of the foregoing detailed description, although discussing exemplary embodiments, is to be construed to cover all modifications, alternatives, and equivalents of the embodiments as may fall within the spirit and scope of the invention as defined by the additional disclosure. Although specific terms are employed herein, they are used in a generic and descriptive sense only and not for purposes of limitation.

A number of publications and patents have been cited hereinabove. Each of the cited publications and patents are hereby incorporated by reference in their entireties.

What is claimed is:

1. A 2,3-disubstituted pyrazolo[1,5-a]pyridine compound having the following structure:

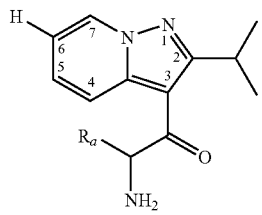

where R$_a$ is —H or lower alkyl.

2. The compound of claim 1, where R$_a$ is a lower alkyl group selected from methyl, ethyl, butyl, and isobutyl.

3. The compound of claim 2, where R$_a$ is methyl.

4. A pharmaceutical composition comprising a 2,3-disubstituted pyrazolo[1,5-a]pyridine compound of claim 1 and a pharmaceutically acceptable excipient.

5. The compound of claim 1, where R$_a$ is hydrogen.

6. The pharmaceutical composition of claim 4, wherein the 2,3-disubstituted pyrazolo[1,5-a]pyridine compound is 2-amino-1-(2-isopropylpyrazolo[1,5-a]pyridin-3-yl)propan-1-one.

7. The pharmaceutical composition of claim 4, wherein the 2,3-disubstituted pyrazolo[1,5-a]pyridine compound is 2-amino-1-(2-isopropylpyrazolo[1,5-a]pyridin-3-yl)ethanone.

8. The pharmaceutical composition of claim 4 in a form suitable for oral administration.

9. The pharmaceutical composition of claim 4 in combination with one or more active ingredients effective for inhibiting or relieving neuropathic pain.

* * * * *